US007974788B2

(12) United States Patent
Rzhetsky et al.

(10) Patent No.: US 7,974,788 B2
(45) Date of Patent: *Jul. 5, 2011

(54) GENE DISCOVERY THROUGH COMPARISONS OF NETWORKS OF STRUCTURAL AND FUNCTIONAL RELATIONSHIPS AMONG KNOWN GENES AND PROTEINS

(76) Inventors: Andrey Rzhetsky, New York, NY (US); Sergey Kalachikov, New York, NY (US); Michael O. Krauthammer, New York, NY (US); Carol Friedman, Larchmont, NY (US); Pauline Kra, Forest Hills, NY (US)

( * ) Notice: Subject to any disclaimer, the term of this patent is extended or adjusted under 35 U.S.C. 154(b) by 6 days.

This patent is subject to a terminal disclaimer.

(21) Appl. No.: 12/492,992

(22) Filed: Jun. 26, 2009

(65) Prior Publication Data

US 2010/0004874 A1 Jan. 7, 2010

Related U.S. Application Data

(60) Continuation of application No. 10/921,286, filed on Aug. 18, 2004, now abandoned, which is a division of application No. 09/549,827, filed on Apr. 14, 2000, now Pat. No. 6,950,753, which is a continuation-in-part of application No. 09/327,983, filed on Jun. 8, 1999, now Pat. No. 6,633,819.

(60) Provisional application No. 60/129,469, filed on Apr. 15, 1999.

(51) Int. Cl.
*G01N 33/48* (2006.01)
*G06G 7/58* (2006.01)
*G06F 17/00* (2006.01)
*G06F 7/00* (2006.01)

(52) U.S. Cl. ............... 702/19; 702/20; 703/11; 700/90; 707/708

(58) Field of Classification Search ................. None
See application file for complete search history.

(56) References Cited

U.S. PATENT DOCUMENTS 6,182,029 B1 1/2001 Friedman
6,915,254 B1 7/2005 Heinze et al.

OTHER PUBLICATIONS

Dictionary definition for "regularize," Merriam-Webster's Online Dictionary, <http://www.merriamwebster.com/dictionary/regularize>, printed on Mar. 28, 2010.*
Altschul et al., 1990, "Basic local alignment search tool," J. Mol. Biol. 215:403-410.
Altschul et al., 1997, "Gapped BLAST and PSI-BLAST: a new generation of protein database search programs," Nucleic Acids Research 25:3389-3402.
Attwood TK et al., 1997, "The PRINTS database of protein fingerprints:a novel information resource for computational molecular biology," J. Chem. Inf. Comput. Sci. 37:417-424.
Bailey et al., 1995, "The value of prior knowledge in discovering motifs," Proc. Int Conf Intell Syst Biol. 3:21-29.
Bailey et al., "Analysis of EST-driven gene annotation in human genomic sequence," Genome Research 8:362-376, 1998.
Ballinger, CA et al., "Identification of CHIP, a novel tetratricopeptide repeat-containing protein that interacts with heat shock proteins and negatively regulates chaperone functions," Mol. Cell. Biol. 19:4535-4545., 1999.
Barabasi and Albert, "Emergence of scaling in random networks," Science 286:509-512, 1999.
Baud et al., 1992, "Natual language processing and semantical representation of medical texts," Meth. Info. Med., 31:117-125.
Boldin et al., 1995, "A novel protein that interacts with the death domain of Fas./AP01 contains a sequence motif related to the death domain," J Biol Chem, 270:7795-8.
Bono et al., "Reconstruction of amino acid biosynthesis pathways from the complete genome sequence," Genome Res. 8:203-210, 1998.
Boskovic J et al., 1996, Transcription Factor GRF10, Accession A25872 (gi|82888).
Bucher et al., 1996, "A flexible motif search technique based on generalized profiles," Comput. Chem., 20:3-23.
Churcher C, 1994, Dihydrolipoamide Dehydrogenase Precursor, Accession A30151 (gi|82983).
Claverie, 1994, "Some useful statistical properties of position-weight matrices," Comput. Chem., 18:287-94.
Contreras R et al., 1994, Hypothetical Protein YBL067C, Accession S45803 (gi|626480).
Cserzo M et al., 1997, "Prediction of transmembrane a-helices in prokaryotic membrane proteins:the dense alignment surface method," Protein Engineering 10:673-676.
Enright, AJ et al., 1999, "Protein interaction maps for complete genomes based on gene fusion events," Nature 402:86-90.
Entian KD et al., 1994, Omnipotent Suppressor Protein SUP45, Accession S46014 (gi|626763).
Felsenstein J, 1978, "Cases in which parsimony or compatibility methods will be positively misleading," Syst. Zool., 27:401-410.
Felsenstein J, 1996, "Inferring phylogenies from protein sequence by parsimony, distance, and likelihood means," Methods in Enzymology 266:418-427.
Fitch WM, 1970, "Distinguishing homologous from analogous proteins," Syst. Zool., 19:99-113.
Fitch WM, 1974, "Evolutionary trees with minimum nucleotide replacements from amino acid sequences," J. Mol. Evol. 3:263-278.
Friedman et al., 1995, "Natural language processing in an operational clinical information system," Natural Language Engineering, 1:83-108.
Friedman C et al., "Evaluating natural language processing," Methods of Information in Medicine 37:334-44, 1998.
Gaillon L et al., 1994, Transcription Factor BAS1, Accession A40083 (gi|101447).
Gilks WR et al., eds., 1996, Markov Chain Monte Carlo Practice, Chapman & Hall/CRC, New York.

(Continued)

*Primary Examiner* — Shubo (Joe) Zhou
(74) *Attorney, Agent, or Firm* — Baker Botts LLP

(57) ABSTRACT

The present invention also relates to natural language processing and extraction of relational information associated with genes and proteins that are found in genomics journal articles. To enable access to information in textual form, the natural language processing system of the present invention provides systems and methods for extracting and structuring information found in the literature in a form appropriate for subsequent applications.

11 Claims, 27 Drawing Sheets

OTHER PUBLICATIONS

Goldman N, 1990,"Maximum likelihood inference of phylogenetic trees, with special references to a poisson process model of DNA substitution and to parsimony analyses," Syst. Zoo. 39:345-361.

Goto et al., 1997, "Organizing and computing metabolic pathway data in terms of binary relations," Pac. Symp. Biocomput. 2:175-186.

Goto S et al., "Ligand:chemical database for enzymes reactions," Nucleic Acid Research 14:591-599, 1998.

Green PJ, 1995, "Reversible Markov chain Monte Carlo computation and Bayesian model determination," Biometrika 82:711-732.

Grundy, "Homology detection via family pairwise search," J. Computational Biology 5:479-491, 1998.

Grundy et al., 1997, "Hidden Markov model analysis of motifs in steroid dehydrogenases and their homologs," Biochem Biophys. Res. Commun. 231(3):760-766.

Grundy WN et al., 1997, "Meta-MEME: motif-based hidden Markov models of protein families," CABIOS 13:397-406.

Gustafsson C et al., 1996, "Identification of new RNA modifying enzymes by iterative genome search using known modifying enzymes as probes," Nucleic Acids Research 24:3756-3762.

Hamlyn N. et al., 1994, Oxoglutarate Dehydrogenase Precursor, Accession DEBY (gi|1070439).

Hastings, 1970, "Monte Carlo sampling methods using Markov chains and their applications," Biometrika 57:97-109.

Haug et al., 1990, "Computerized extraction of coded findings from free-text radiologic reports," Radiology, 174:543-548.

Hirst et al., 1991, "Prediction of ATP-binding motifs:a comparison of a perceptron-type neural network and a consensus sequence method," Prot Eng, 4:615-623.

Hofmann et al., 1995, "The death domain motif found in Fas(Apo-1) and TNF receptor is present in proteins involved in apoptosis and axonal guidance," FEBS Lett, 371:321-3.

Hripcsak G et al., "Unlocking clinical data from narrative reports: a study of natural language processing," 1995, Ann. Intern Med. 122:681-688.

Hu et al., "WD-40 repeat region regulates Apaf-1 self-association and procaspase-9 activation," J. Biol. Chem. 273:33489-33494, 1998.

Hurlin PJ., 1995, "Mad3 and Mad4:novel Max-interacting transcriptional repressors that suppress c-myc dependent transformation and are expressed during neural and epidermal differentiation," EMBO 14:5646-59.

Jain NL et al., 1996, "Identification of suspected tuberculosis patients based on natural language processing of chest radiograph reports," Proc. AMIA Annu Fall Symp 542-546.

James CM et al., 1996, Cell Division Control Protein CDC43, Accession RGBY43 (gi|2144611).

Karlin S et al., 1990, "Methods for assessing the statistical significance of the molecular sequences features by using general scoring schemes," Proc. Natl. Acad. Sci. USA 87:2264-2268.

Kazic, 1994, "Representation of biochemistry for modeling organisms," In: Molecular Modeling: From Virtual Tools to Real Problems, Kumosinski, T. and Liebman, M.N. (Eds.), American Chemical Society, Washington, D.C. pp. 486-494.

Kazic, 1994, "Biochemical databases:Challenges and opportunities," In: New Data Challenges in Our Information Age Glaesar, P.S. and Millward, M.T.L. (Eds.). Proceedings of the Thirteenth International CODATA Secretariat, Paris pp. C133-C140.

Kim, K. H., "Comparative Molecular Field Analysis (CoMFA)", In: Molecular Similarity in Drug Design, Edited by Dean, P.M., 1995.

Koonin EV et al., 1996, "Protein sequence comparison at sequence scale," Methods in Enzymology 266:295-323.

Krogh et al., 1994, "Hidden Markov Models in computational biology, applications to protein modeling," J. Mol. Biol. 235:1501-1531.

Lenert et al., 1994, "Automated linkage of free-text description of patients with a practice guideline," AMIA, 274-278.

Mathews S et al., 1996,"The phytochrome family in grasses (Poaceae): A phlogeny and evidence that grasses have a subset of the loci found in dicot angiosperms," Mol. Biol. Evol., 13:1141-1150.

Marcotte, EM et al., "Detecting protein function and protein-protein interactions from genome sequences," Science 285:751-753, 1999.

Miklos GLG, et al., 1996, "The role of the genome project in determining gene function:insights from model organisms," Cell 86:521-529.

Murphy L et al., 1994, Suppressor 2 Protein, Accession EFBY52 (gi|72877).

Mushegian AR et al., 1997, "Positionally cloned human disease genes:patterns of evolutionary conservation and functional motifs,"Proc. Natl. Acad Sci. USA 94:5831-5836.

Neuwald AF et al., 1995,"Gibbs motif sampling:detection of bacterial outer membrane protein repeats," Protein Sci. 4:1618-1632.

Neuwald, 1997, "Extracting protein alignment models from the sequence database," Nucleic Acids Research 25:1665-1677.

Orengo et al., 1993, "A local alignment method for protein structure motifs," J Mol Biol 233(3):488-497.

Pamilo P. et al., 1988, "Relationship between gene tree and species trees," Mol. Biol. Evol. 5:568-583.

Pearson, 1997, "Identifying distantly related protein sequences," CABIOS, 13:325-332.

Peitgen HO, Juregens H, Saupe D, 1992, Chaos and Fractals: New Frontiers of Science, Springer Verlag, New York.

Pena et al., 1997, "Stress-induced apoptosis and the sphingomyelin pathway," Biochem Pharmacol., 53:615-621.

Purnelle B et al., 1995, Pre-mRNA Splicing Factor PRP2I, Accession S23553 (gi|280467).

Rieger M, 1994, Protein Farnesyltransferase Chain RAM2, Accession P29703 (gi|266880).

Rogers MA et al., 1997, "Sequences and differential expression of the three novel human type II hair keratins," Differentiation 61:187-194.

Ruecknagel, KP et al., "Dihydrolipoamide S-Succinyltransferase Precursor, Accession XUBYSD" (gi|2144399), 1999.

Saitou N, 1987, "The neighbor-joining method: A new method for reconstructing phylogenetic trees," Mol. Biol. Evol. 4:406-425.

Selkov et al., 1996, "The metabolic pathway collection from EMP: the enzymes and metabolic pathways database," Nucleic Acids Research 24:26-28.

Selkov, E et al., 1997, "The metabolic pathway collection: an update," Nucleic Acids Research 25:37-38.

Sharkey et al., 1997, "Hox genes in evolution: protein surfaces and paralog groups," TIG 13:145-151.

Sonnhammer, Ell et al., "Pfam:multiple sequence alignments and HMM profiles of protein domains," Nucleic Acids Research 26(1):320-322, 1998.

Sonnhammer Ell et al., 1997, Pfam:A comprehensive database of protein domains families based on seed alignments, Proteins Structure Function and Genetics 28:405-420.

Skvorak AB et al., 1997, An ancient conserved gene expressed in the human inner ear: identification, expression analysis, and chromosome mapping of human and mouse antiquitin (ATQ1), Genomics 46:191-199.

Tatusov RL et al., 1994, "Detection of conserved segments in proteins: Iterative scanning of sequence databases with alignment blocks," Proc. Natl Acad. Sci. USA 91:12091-12095.

Tatusov RL et al., 1997, "A genomic perspective on protein families," Science 278:631-637.

Ullrich O et al., 1993, "Rab GDP dissociation inhibitor as a general regulator for the membrane association of Rab proteins," J. Biol. Chem. 268:18143-18150.

Venezia, 1993, "Rapid motif compliance scoring with match weight sets," Comput Appl Biosci, 9:65-9.

Wu CH et al., 1996, "Motif identification neural design for rapid and sensitive protein family search," Comput. Appl. Biosci 12:109-118.

Wu SK et al., 1998, "Molecular role for the Rab binding platform of guanine nucleotide dissociation inhibitor in endoplasmic reticulum to golgi transport," J. Biol. Chem. 273:26931-26938.

Yang Z et al., 1995, "Maximum likelihood trees from DNA sequences: A peculiar statistical estimation problem," Syst. Biol. 44:384-399.

Yuan et al., 1998, "Towards detection of orthologues in sequence databases," Bioinformatics 14:285-289.

Zweigenbaum et al., 1995, "A multi-lingual architecture for building a normalised conceptual representation from medical language," AMIA, 357-361.

U.S. Appl. No. 09/327,983, May 9, 2002 Non-Final Office Action.

U.S. Appl. No. 09/327,983, Nov. 20, 2000 Response to Non-Final Office Action.

U.S. Appl. No. 09/327,983, Mar. 6, 2001 Final Office Action.

U.S. Appl. No. 09/327,983, Aug. 27, 2001 Continuing Prosecution Application—Continuation (ACPA).
U.S. Appl. No. 09/327,983, Oct. 24, 2001 Express Abandonment.
U.S. Appl. No. 09/327,983, Dec. 19, 2001 Supplemental Response.
U.S. Appl. No. 09/327,983, Dec. 31, 2001 Non-Final Office Action.
U.S. Appl. No. 09/327,983, Jul. 8, 2002 Response to Non-Final Office Action.
U.S. Appl. No. 09/327,983, Oct. 2, 2002 Non-Final Office Action.
U.S. Appl. No. 09/327,983, Jan. 6, 2003 Response to Non-Final Office Action.
U.S. Appl. No. 09/327,983, Mar. 6, 2003 Notice of Allowance.
U.S. Appl. No. 09/327,983, Jun. 11, 2008 Certificate of Correction.
U.S. Appl. No. 09/549,827, Jul. 13, 2000 Preliminary Amendment.
U.S. Appl. No. 09/549,827, Jan. 2, 2001 Requirement for Restriction / Election.
U.S. Appl. No. 09/549,827, Oct. 9, 2001 Response to Non-Final Office Action.
U.S. Appl. No. 09/549,827, Dec. 28, 2001 Non-Final Office Action.
U.S. Appl. No. 09/549,827, Jul. 8, 2002 Response to Non-Final Office Action.
U.S. Appl. No. 09/549,827, Sep. 30, 2002 Non-Final Office Action.
U.S. Appl. No. 09/549,827, Feb. 3, 2003 Response to Non-Final Office Action.
U.S. Appl. No. 09/549,827, Apr. 15, 2003 Final Office Action.
U.S. Appl. No. 09/549,827, Oct. 20, 2003 Response to Final Office Action.
U.S. Appl. No. 09/549,827, Nov. 3, 2003 Examiner Interview Summary Record.
U.S. Appl. No. 09/549,827, Jan. 27, 2004 Final Office Action.
U.S. Appl. No. 09/549,827, Mar. 31, 2004 Response to Final Office Action.
U.S. Appl. No. 09/549,827, Apr. 21, 2004 Terminal Disclaimer Accepted.
U.S. Appl. No. 09/549,827, May 6, 2004 Notice of Allowance.
U.S. Appl. No. 09/549,827, Aug. 2, 2004 Amendment after Notice of Allowance.
U.S. Appl. No. 09/549,827, Dec. 16, 2004 Response to Amendmend under Rule 312.
U.S. Appl. No. 10/921,286, Aug. 18, 2004 Preliminary Amendment.
U.S. Appl. No. 10/921,286, Jan. 4, 2007 Requirement for Restriction / Election.
U.S. Appl. No. 10/921,286, Mar. 29, 2007 Response to Restriction / Election.
U.S. Appl. No. 10/921,286, Jul. 2, 2007 Non-Final Office Action.
U.S. Appl. No. 10/921,286, Dec. 3, 2007 Response to Non-Final Office Action.
U.S. Appl. No. 10/921,286, Mar. 13, 2008 Response to Non-Final Office Action.
U.S. Appl. No. 10/921,286, Jul. 3, 2008 Examiner Interview Summary.
U.S. Appl. No. 10/921,286, Jul. 11, 2008 Response to Non-Final Office Action.
U.S. Appl. No. 10/921,286, Nov. 4, 2008 Final Office Action.
U.S. Appl. No. 10/921,286, May 13, 2009 Abandonment for Failure to Respond to Office Action.
U.S. Appl. No. 10/921,286, Aug. 26, 2009 Petition to Revive Application Granted.
U.S. Appl. No. 10/921,286, Sep. 8, 2009 Express Abandonment.

* cited by examiner bcl-xL / bcl / bcl-xS / ced-9 / Bax / Blk / Bak / p21 / NGFI-B / N10 /Nak1 / Nur77 / Nurr 1 / Nor-1 / Noi-1 / RXR/ galectin-1 / N-glycan / CNTF / lck / fyn / ZAP-70 / raf / ras / MAP / protein kinase C / PKC / phosphatase calcineurin / NF-AT / AP1 / 14.3-3 / Raf-1 / Bcl-2 / interleukin / IL-1 / IL-3 / cytokine / IGF-1 / CD95 / Apo-1 / RIP / FAF1 / FADD / FAP-1 / TNFR / TRAF / TRAP1 / TRAP2 / TRADD / HIAP1 / HIAP2 / CD40 / CD30 / XIAP / CD2 / CD3 / TCR / Bcl-w / Mci-1 / NR-13 / BHRF1 / HMW5-HL / E1B19K / Nbk / Mch2 / CPP32 / ICE / FLICE / Nedd-2 / TX / Mch3 / Mch4 / ICB-1s / nor-1 / DNAseI / caspase / MACH1 / Mch5 / apopain / Yama / ICH / CMH / ced-3 / ced-4 / ced-9 / p53 / MKK3 / MKK2 / MKK4 / BAG-1 / Src / FAST/ p38 / p42 / ERK1 / p44 / ERK2 / SAPK / JNK / MEK / C-JUN / MEF2D / ATF2 / calcineurin / ELK-1 / protein phosphatase 2A / raf-1 / IL-1 beta / TNF / PTK / Apaf / p35 / ETS / C-Myc / IL-2 / IL-2 receptor / NF-kappa B / TNFR-1 / TRAIL / APO-2L / DR4 / death receptor / DR3 / DR2 / DR5 / DR1 / bod / BMPR / BMP-x / TGF / grim / bid / FAN / perforin / Fas-L / Fas / DcR1 / decoy receptor / wxi-1 / NGF receptor / growth factor / RAR

FIG. 4

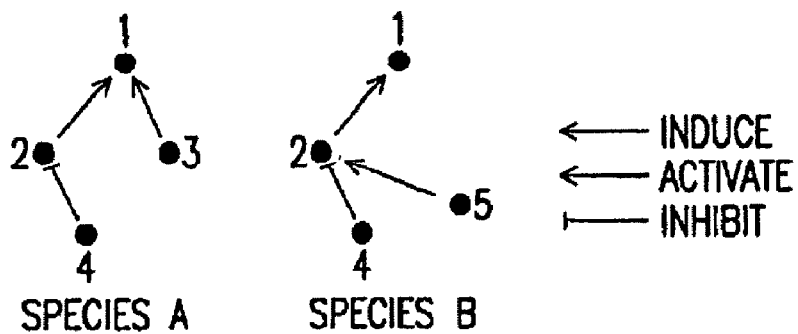
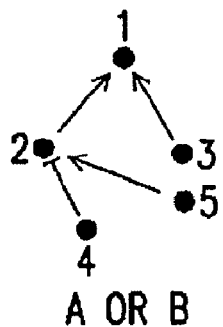
FIG. 9B
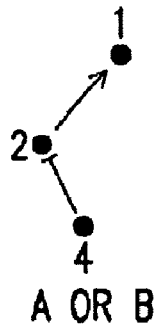
FIG. 9C
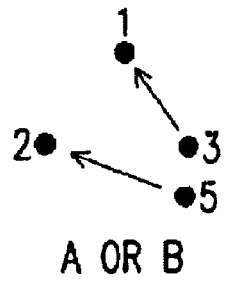
FIG. 9D
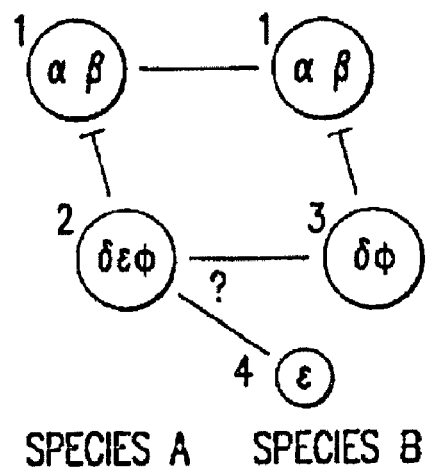
FIG. 10

LEGEND FOR FIGS. 13A, 13B AND 13C

☆ POZ/BTB DOMAIN
○ KELCH REPEAT
⊖ RING FINGER DOMAIN
▢ FIBRONECTIN III DOMAIN
◇ CYCLIN REPEAT
△ EGF-LIKE DOMAIN
▭ CUB DOMAIN
▲ LAMININ EGF-LIKE DOMAIN

⇨ TRANSMEMBRANE HELIX
○ BP-BIPARTITE NUCLEAR LOCALIZATION SIGNAL
▭ TRANSFERASE DOMAIN
⬭ NEW A-DOMAIN
▢ NEW POZ-LINKER DOMAIN
◯ NEW B-DOMAIN
⬯ NEW SPOP DOMAIN

▯ NEW (?) TN (TUMOR NECROSIS) DOMAIN
○ FOS/JUN DNA-BINDING DOMAIN
▯ gi|1707204-DOMAIN
⊕ NEW HAT DOMAIN (HEMAGGLUTININ, ALPHA TOXIN, TUMOR NECROSIS-FACTOR-ALPHA-INDUCED PROTEIN)
⊗ DEATH DOMAIN
◇ KINASE DOMAIN

⇧ HEAT REPEAT
⊙ Zn-FINGER $C_2H_2$
▯ PROLINE-RICH REGION
◆ PKC-C1 DOMAIN, GAG/PE-BINDING
◇ PKC-C2 DOMAIN
◯ PROTEIN KINASE DOMAIN

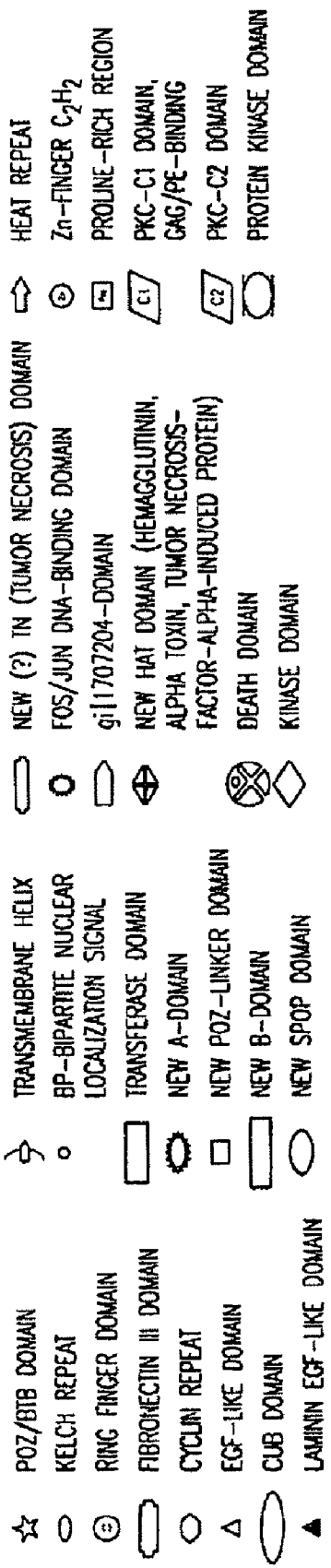

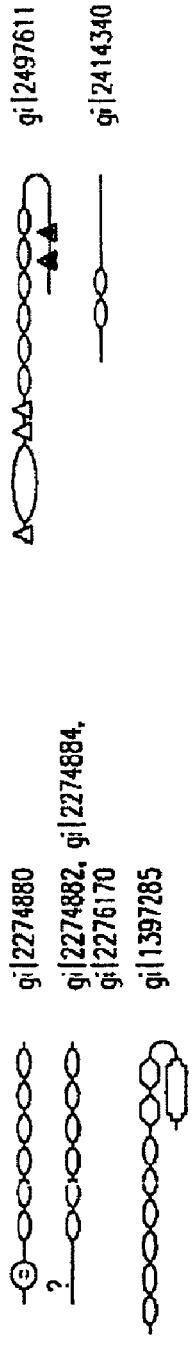

FIG. 13A

>gi|2210766|gb|AA481214|AA481214 aa34e02.r1 NCI_CGAP_GCB1 Homo sapiens cDNA clone
IMAGE:815162 5' similar to WP:W07A12.4 CE03795 :, mRNA sequence [Homo sapiens]
CATGGCTTCCTGGACACCAGACCAACCCTGCCATCCGGGAGCAGAGACGGTCAAGTCCATGCTGCTCCTGGCCCCAA
AGCTGAACGAGGCCAACCTCAACACCACAGTCTCAATGTGGAGCTGATGAAGCACTTTGCACGGCTACAAGGCCAAGGATGAACA
GGGCCCCATCCGCTGCAACACCACAGTCTGCCTTGAGCCGACCACTAGGGACCGTTTGCACGGTCCCGGGTTGCGGGTG
CACAGGGTCCTTCCTCTGCCTTGCCACCCACAACCTCTACTCAATGAACGACTGTGCCCAGAAGATCCTGCCTGTGCT
TCCTGGGCTTTGCTGCCGGTCTCACTGTAGATCCTGAGAAATCCGTGCGAGACCAGGCCTTCAAGGCA
CTGCCGGTCTCACTGTAGATCCTGAGAAATCCGTGCGAGACCAGGCCTTCAAGGCA

ID8

>gi|1349211|gb|W51957|W51957 zc45f01.r1 Soares_senescent_fibroblasts_NbHSF Homo
sapiens cDNA clone IMAGE:325273 5', mRNA sequence [Homo sapiens]
CCTTGCAGTTCGGCAATGCTGGGGCCGTTGTCCTCACGCCCCTCTTCAAGGTGGGCAAGTTCCTGAGCGC
TGAGGAGTATCAGCAGCAGATCATCCCTGTGGTGGTCCAGTTCATCAGATGTTCTCATCCACTGACCAGTTCCTGAGCGC
ATCCGNCTCCTGCAGCAGCAGATGGAGCAGTTCATCAGTGAGCAGTTCCTTGACGAGCCAACAGTCAACACCCAGATCT
TCCCCCACGTCGTACATGGCTTCCTGGACACCAGGAGCCAACCCTGCCATCCGGAGCTGATGAAGCACTTTGCACGGCTACAG
GCTCCTGGCCCCAAAGCTGAACGAGGCCCAACCTCAACAGGCAGCCAACCTCGGCTGCCTGCAACACCACAGTCTGCCTGCAACACCACAGTCTGCCTTTGCACGGCTACAG
GCCAAGGATGAACAGGGCCCCATCCGCTGCAACACCACAGTCTGCCTGCAACACCACAGTCTGCCTTTGCACGGCTACAG
GTGCTAGCACCAGAGACACCAGGGTCCTTACCTCTG

BASE COUNT   405 a      545 c      493 g      278 t        6 others
ORIGIN
    1 cagccgaagc amgcaaaaat tcttccagga gctgagcaag agcctggacg cattccctga
   61 ggayttctgt cggcacaagg tgctgcccca gctgctgacc gccttcgagt tcggcaatgc
  121 tggggccgtt gtcctcacgc ccctcttcaa ggtgggcaag ttcctgagcg ctgaggagta
  181 tcagcagaag atcatccctg tggtggtcaa gatgttctca tccactgacc gggccatgcg
  241 catccgcctc ctgcagcaga tggagcagtt catccagtac cttgacgagc aacagtcaa
  301 cacccagatc ttccccacg tcgtacatgg cttcctggac accaaccctg ccatccggga
  361 gcagacggtc aagtccatgc tgctcctggc cccaaagctg aacgaggcca acctcaatgt
  421 ggagctgatg aagcactttg cacggctaca ggccaaggat gaacagggcc ccatccgctg
  481 caacaccaca gtctgcctgg gcaaaatcgg ctcctacctc agtgctagca ccagacacag
  541 ggtccttacc tctgccttca gccgagccac tagggacccg tttgcaccgt cccgggttgc
  601 gggtgtcctg ggctttgctg ccacccacaa cctctactca atgaacgact gtgcccagaa
  661 gatcctgcct gtgctctgcg gtctcactgt agatcctgag aaatccgtgc gagaccaggc
  721 cttcaaggcm wttcggagct tcctgtccaa attggagtct gtgtcggagg acccgaccca
  781 gctggaggaa gtggagaagg atgtccatgc agcctccagc cctggcatgg gaggagccgc
  841 agctagctgg gcaggctggg cgtgaccggg gtctcctcac tcacctccaa gctgatccgt
  901 tcgcacccaa ccactgcccc aacagaaacc aacattcccc aaagacccac gcctgaagga
  961 gttcctgccc cagcccccac cctgttcct gccacccta caacctcagg ccactgggag
 1021 acgcaggagg aggacaagga cacagcagag gacagcagca ctgctgacag atgggacgac
 1081 gaagactggg gcagcctgga gcaggaggcc gagtctgtgc tggcccagca ggacgactgg
 1141 agcaccgggg gccaagtgag ccgtgctagt caggtcagca actccgacca caaatcctcc
 1201 aaatccccag agtccgactg gagcagctgg gaarctgagg gctcctggga acagggctgg
 1261 caggagccaa gctcccagga gccacctyct gacggtacac ggctggccag cgagtataac
 1321 tggggtggcc cagagtccag cgacaagggc gacccttcg ctaccctgtc tgcacgtccc
 1381 agcacccagc cgaggccaga ctcttggggt gaggacaact gggagggcct cgagactgac
 1441 agtcgacagg tcaaggctga gctggcccgg aagaagcgcg aggagcggcg gcgggagatg
 1501 gaggccaaac gcgccgagag gaaggtgcca agggccccat gaagctggga gcccggaagc
 1561 tggactgaac cgtggcggtg gcccttcccg gctgcggaga gcccgcccca cagatgtatt
 1621 tattgtacaa accatgtgag cccggccgcc cagccaggcc atctcacgtg tacataatca
 1681 gagccacaat aaattctatt tcacaaaaaa aaaaaaaaaa aaaaaa
//

>sp|P15533|RPT1_MOUSE DOWN REGULATORY PROTEIN OF INTERLEUKIN 2 RECEPTOR
(J03776) rpt-1r [Mus musculus] Length = 353

Score = 92.0 bits (237), Expect = 6e-20

```
Query 194  VMELLEEDLTCPICCSLFDDPRVLPCSHNFCKKCLEGILEGSVRNSMWRPAPFKCPTCRK  373
           V+E+++E++TCPIC  L +P   C+H+FC+ C+    E S RN+       CP CR
Sbjct   5  VLEMIKEEVTCPICLELLKEPVSADCNHSFCRACITLNYE-SNRNT---DGKGNCPVCRV  60

Query 374  ETSATGINSLQVNYSLKGIVEKYNKIKISP----KMPVCKGHMGQPLNIFCLTDMQLICG  541
                 +L+ N + IVE+    K P   K+ +C  H G+ L +FC  DM +IC
Sbjct  61  PYP---FGNLRPNLHVANIVERLKGFKSIPEEEQKVNICAQH-GEKLRLFCRKDMMVICW  116

Query 542  ICATRGEHTKHVFCSIEDAYAQERDAFESLFQSF------ETWRRGDALSRLDTMETSK  700
           +C   EH  H   IE+  + ++  +             + W+    L R+D
Sbjct 117  LCERSQEHRGHQTALIEEVDQEYKEKLQGALWKLMKKAKICDEWQDDLQLQRVDW----  171

Query 701  RKSLQLMTKDSDKVKEFFEKLQHTLDQKKNEILSDFETMKLAVMQAYDPEINKL  862
           +Q+  + + V+  F+ L+  LD K+NE  L  + K  VM+ +   N+L
Sbjct 172  ENQIQI---NVENVQRQFKGLRDLLDSKENEELQKLKKEKKEVMEKLEESENEL  222
```

Homology covers ring finger, B-box and the beginning of coiled coil domain in the CLL ring finger protein

FIG. 15

ACTIVATED CD4+ T-CELLS

WHEN rpt1 IS KNOCKED OUT:

TBLASTN 2.0.8 [Jan-05-1999]

Reference:
Altschul, Stephen F., Thomas L. Madden, Alejandro A. Schaffer,
Jinghui Zhang, Zheng Zhang, Webb Miller, and David L. Lipman (1997),
"Gapped BLAST and PSI-BLAST: a new generation of protein database search
programs", Nucleic Acids Res. 25:3389-3402.

Query= gi |2137498|Mad3m
       (205 letters)

gb|AA278224|AA2278224 zs77e05.r1 NCI_CGAP_GCB1 Homo sapiens cDNA clone IMAGE:703520 5'
     similar to TR:G1184157 G1184157 MAX-INTERACTING
     TRANSCRIPTIONAL REPRESSOR. ;
     Length = 430

Score = 209 bits (526), Expect = 1e-53
 Identities = 104/124 (83%), Positives = 116/124 (92%), Gaps = 1/124 (0%)
 Frame = +2

Query: 1    MEPVASNIQVLLQAAEFLERREREAEHGYASLCPHHSPGTVCRRRKPPLQAPGALNSGRS  60     ID14
            MEP+ASNIQVLLQAAEFLERREREAEHGYASLCPH SPG + RR+K P QAPGA +SGRS        ID15
Sbjct: 56   MEPLASNIQVLLQAAEFLERREREAEHGYASLCPHRSPGPIHRRKKRPPQAPGAQDSGRS  235    ID16

Query: 61   VHNELEKRRRAQLKRCLEQLRQQMPLGVDCTRYTTLSLL-RARVHIQKLEEQEQQARRLK  119
            VHNELEKRRRAQLKRCLE+L+QQMPLG DC RYTTLSLL RAR+HIQKLE+QEQ+AR+LK
Sbjct: 236  VHNELEKRRRAQLKRCLERLKQQMPLGGDCARYTTLSLLRRARMHIQKLEDQEQRARQLK  415

Query: 120  EKLRS  124
            E+LR+
Sbjct: 416  ERLRT  430 dbj|C02407|C02407 HUMGS0012279, Human Gene Signature, 3'-directed cDNA sequence.
     Length = 348

Score = 97.5 bits (239), Expect = 6e-20
 Identities = 51/63 (80%), Positives = 56/63 (87%)
 Frame = +3

Query: 125  KQQSLQQQLEQLQGLPGARERERLRADSLDSSGLSSERSDSDQEDLEVDVENLVFGTETE  184    ID17
            KQQSLQ+   QL+GL GA ERERLRADSLDSSGLSSERSDSDQE+LEVDVE+LVFG E E         ID18
Sbjct: 45   KQQSLQRXWMQLRGLAGAAERERLRADSLDSSGLSSERSDSDQEELEVDVESLVFGGEAE  224    ID19

Query: 185  LLQ  187
            LL+
Sbjct: 225  LLR  233

FIG. 17A

BASE COUNT 130 a    234 c    258 g    106 t    5 others
ORIGIN
  1 cagccgcttg ctccggccgg caccctaggc cgcagtccgc caggctgtcg ccgacatgga
 61 acccttggcc agcaacatcc aggtcctgct gcaggcggcc gagttcctgg agcgccgtga
121 gagagaggcc gagcatggtt atgcgtccct gtgcccgcat cgcagtccag gccccatcca
181 caggaggaag aagcgacccc cccaggctcc tggcgcgcag gacagcgggc ggtcagtgca
241 caatgaactg gagaagcgca ggagggccca gttgaagcgg tgcctggagc ggctgaagca
301 gcagatgccc ctgggcggcg actgtgcccg gtacaccacg ctgagcctgc tgcgccgtgc
361 caggatgcac atccagaagc tggaggatca ggagcagcgg gcccgacagc tcaaggagag
421 gctgcgcaca aagcagcaga gcctgcagcg gcantggatg cagctccggg ggctggcagg
481 ngcggccgag cgggagcgnc tgcggcgga cagtctggac tcctcaggcc tctcctctga
541 gcgctcagac tcagaccaag aggagctgga ggtggatgtg gagagcctgg tgtttggggg
601 tgaggccgag ctgctgcggg gcttcgtcgc cggccaggag cacagctact cgcacgtcgg
661 cggcgcctgg ctatgatgtt cctcacccan ggcgggcctc tgccctctta ctcgttgccc
721 aagcccactt tnc

FIG.17B

```
>Mad3b(Putative)
MEPLASNIQVLLQAAEFLERREREAEHGYASLCPHRSPGPTHRRKKRPPQAPGAQDSGRSVHNELEKRRAQLK
RCLERLKQQMPLGGDCARYTTLSLLRRARMHIQKLEDQERARQLKERLRTKQQSLQRXWMQLRGLAGAAERER      ID27
LRADSLDSSGGLSSERSDSDQEELEVDVESLVFGGEAELLRGFVAGQEHSYSHVGGAWL
```

FIG. 17C

|  | | |
|---|---|---|
| gi\|2506888\|MAD4e | MATAVGHNIQLLLEAADYLERREREAEHGYASMLPYS-KQADAFKRRNKPKKNST---SSRSTHNEMEKNRRAHLRLCLEKLKLGLVPLGPESSRHTTLSLL | ID21 |
| gi\|7299781\|MAD4h | MAAAYRNNIQMLLEAADYLERREREAEHGYASMLPYNNKQRDALKRRNKSKKWNS--SSRSTHNEMEKNRRAHLRLCLEKLLGLVPLGPESSRHTTLSLL | 22 |
| gi\|2792362\|Mad4h | ---MELNSLITLEAAEYLERRDREAEHGYASVLPFDGDFAREKTKAAGLVRKAP--NNRSSHNELEKHRRAKLRLYLEQLKQLVPLGPDSTRHTTLSLL | 23 |
| gi\|2137499\|Mad4m | ---MELNSLLLLLEAAEYLERRDREAEHGYASMLPFDGDFARKKTKTAGLVRKGP--NNRSSHNELEKHRRAKLRLYLEQLKQLGPLGPDSTRHTTLSLL | 24 |
| gi\|2137498\|Mad3m | -MEPVASNIQVLLQAAEFLERREREAEHGYASLCPHSPGTVCRRRKPPLQAPGALNSGRSVHNELEKRRAQLKRCLEQLRQQMPLGVDCTRYTTLSLL | 25 |
| Mad3h Putative | -MEPLASNIQVLLQAAEFLRRREREAEHGYASLCPHRSPGPTHRRKKRPPQAPGAQDSGRSVHNELEKRRAQLKRCLERLKQQMPLGGDCARYTTLSLL | 26 |

| gi\|2506888\|MAD4e | TKAKLHIKKLEDCDRKAVHQIDQLQEQRHLKRRLEKLGAERTR--------MDSVG-SVVSSERSDSDREELDVDVDVDVDVEGTDYLPGDLGWSSS- |
| gi\|7299781\|MAD4h | TKAKLHIKKLEDCDRKAVHQIDQLQEQRHLKRRLEKLGIERIR--------MDSIG-STVSSERSDSDRE--------EIDVDVESTDYLTGDLDWSSSS |
| gi\|2792362\|Mad4h | KRAKVHIKKLEEQQRRALSIKEQLQQEHRFLKRRLEQLSVQSVER----VRTDSTG-SAVSTD--DSEQE-----------VDIEGMEFGPGELDSVGS- |
| gi\|2137499\|Mad4m | K-AKMHIKKLEEQQRRALSIKEQLQREHRFLKRRLEQLSVQSVR-----VRTDSTG-SAVSTD--DSEQE-----------VDIEGMEFGPGELDSAGS- |
| gi\|2137498\|Mad3m | R-ARVHIQKLEEQQARRLKEKLRSKQQSLQQQLEQLQGLPGARERPRLRADSLRADSLDSSGLSSERSDSDQE-----------DLSVDVENLVFG-TETELLQSF |
| Mad3h Putative | RRARMHIQKLEDQEQRARQLKERLRTKQQSLQRXWMQLRGLAGAAERERLRADSLRADSLDSSGLSSERSDSDQE-----------ELEVDVESLVFG-GEAELLRGF |

| gi\|2506888\|MAD4e | VSDSDERGSMQSLG-SDEGYSSATVKRAKLQQGHKAGLGL |
| gi\|7299781\|MAD4h | VSDSDERGSMQSLG-SDEGYSSTSIKRIKLQQSHKACLGL |
| gi\|2792362\|Mad4h | SSDADDHYSLQSSGTGGDSGFGPHCRRLGRPALS------ |
| gi\|2137499\|Mad4m | SSDADDHYSLQSSGCSDSSYGHPCRRPGCPGLS------- |
| gi\|2137498\|Mad3m | SAGREHSYSHSTCAWL------------------------ |
| Mad3h Putative | VAGQEHSYSHVGGAWL------------------------ |

FIG. 17D

GENE DISCOVERY THROUGH COMPARISONS OF NETWORKS OF STRUCTURAL AND FUNCTIONAL RELATIONSHIPS AMONG KNOWN GENES AND PROTEINS

CROSS REFERENCE TO RELATED APPLICATIONS

The present application is a continuation application of U.S. application Ser. No. 10/921,286, filed Aug. 18, 2004, now abandoned, which is a divisional application of U.S. application Ser. No. 09/549,827, filed Apr. 14, 2000, now U.S. Pat. No. 6,950,753, which is a continuation-in-part application of U.S. application Ser. No. 09/327,983, filed Jun. 8, 1999, now U.S. Pat. No. 6,633,819, which claims priority to U.S. Provisional Application No. 60/129,469, filed Apr. 15, 1999, the disclosure of all of which is incorporated herein in their entirety.

STATEMENT REGARDING FEDERALLY FUNDED RESEARCH

This invention was made with government support under grant numbers LM06274 and LM05627 awarded by the National Library of Medicine. The government has certain rights in the invention.

COMPUTER SOURCE CODE AND SEQUENCE LISTING

An appendix containing source code listing utilized in practicing an exemplary embodiment of the invention is included as part of the Specification. The Specification also incorporates by reference a Sequence Listing submitted via EFS. Pursuant to 37 C.F.R. §1.52(e)(5), the Sequence Listing text file, identified as 0700503823seqlist.txt, is 29,017 bytes and was created on Jun. 30, 2010. The Sequence Listing does not extend beyond the scope of the specification and thus does not contain new matter.

1. INTRODUCTION

The present invention relates to methods for identifying novel genes comprising: (i) generating one or more specialized databases containing information on gene/protein structure, function and/or regulatory interactions; and (ii) searching the specialized databases for homology or for a particular motif and thereby identifying a putative novel gene of interest. The invention may further comprise performing simulation and hypothesis testing to identify or confirm that the putative gene is a novel gene of interest.

The present invention relates to natural language processing and extraction of relational information associated with genes and proteins that are found in genomics journal articles. To enable access to information in textual form, the natural language processing system of the present invention provides a method for extracting and structuring information found in the literature in a form appropriate for subsequent applications. Specifically, the present invention provides for the generation of specialized databases containing information on gene/protein structure, function and regulatory interactions based on the retrieval of such information from research articles and databases, and computer representation of such information in a manner that allows efficient access to the extracted information.

The invention further provides for the use of the specialized databases for identifying novel genes based on detection of sequence similarities and domain/motif matches between genes/proteins, computation and interpretation of phylogenetic trees for multigene families, and analysis of homologous regulatory networks. The methods of the invention are based on the observation that functionally similar regulatory systems are generated during evolution by genetic duplication of ancestral genes. Thus, a comparison of homologous/similar networks within the same organism and between different species will allow the identification of genes absent in one of the systems under comparison. In this way genes that contribute to the phenotype of a specific disease associated with a particular biological system under analysis may be identified.

2. BACKGROUND OF THE INVENTION

2.1. Natural Language Processing

Researchers working in molecular biology must constantly consider the information present in the literature relating to their regulatory systems of interest and the genes and proteins that operate within those systems. Unfortunately, to remain up-to-date on the relevant literature, the researcher is required to perform laborious reading and manual integration of research articles, each of which may address a narrow subject. Therefore, technology that enables rapid retrieval of information from literature and manipulation of derived functional data should have a dramatic effect on the access of the researcher to important facts and ultimately should facilitate the discovery of novel human genes.

Natural language processing is an automated system that provides for a complex of programs for automatic retrieval of information from text analysis and for the computer representation of that information in a form that allows efficient access and extraction of that information. MedLee (Medical Language Extraction and Encoding System) has recently been successfully used for processing different types of medical texts as described in co-pending U.S. patent application Ser. No. 09/370,329, incorporated herein in its entirety by reference (see also, Friedman et al., 1994, J. Amer. Med. Inf. Assoc. 1:161-174; Hripcsak et al. 1995, Ann. Intern. Med. 122:681-688; Hripcsak et al., 1998, Meth. Inform. Med.; Jain et al., 1996, Proc. AMIA Annu. Fall Symp. 542-546; Knirsch et al., 1998). When tested, MedLEE was on average as successful in retrieving reports associated with specified clinical connections as twelve medical experts invited for evaluation of the system.

Another text analysis technique has recently been developed that combines finite-state machines with statistical machine learning approaches. These models extract detailed semantic information from texts (e.g., see Hatzivassiloglou 1996, In Klavens, J. L., and Resnick, P. S. (eds) *The Balancing Act: Combining Symbolic and Statistical Approaches to Language*, MIT Press, Cambridge, Mass.) when extensive prior knowledge about the domain is not available. The techniques have been subsequently applied to the tasks of (i) automatically identifying medical terms for the automated summarization of research articles reporting on clinical studies and (ii) sanitizing sensitive information in patient records so that they can be widely disseminated for research purposes.

A number of projects have also been developed as statistical information extraction tools that operate with limited or no prior knowledge about the application domain. These earlier efforts include XTRACT, a tool that recovers collocational restrictions between words that has been licensed to more than thirty sites worldwide (Smadja, F., 1993, J. Comp. Ling. 19:143-177), CHAMPOLLION, a system that retrieves bilingual mappings between words and phrases in parallel texts from different languages (Smadja, F. et al. 1996, J. Computational Linguistics 22:1-38), and a system that automatically aligns noisy, semi-parallel texts from different languages (Fung, P. and McKeown, K. R., 1997, Machine Translation 11:23-29).

2.2. Identification of Novel Genes

A variety of different methods are currently utilized for the identification and characterization of novel genes. Perhaps the most widely used method for generating large quantities of sequence information is via high throughput nucleotide sequencing of random DNA fragments. A disadvantage associated with this gene discovery technique is that in most instances when genes are identified their function is unknown.

For identification of specific disease genes, positional cloning is currently the most widely used method. The positional cloning approach combines methods of formal genetics, physical mapping and mutation analysis and usually starts with a precise description of the disease phenotype and a tracing of the disease through families of affected individuals. Genetic linkage data obtained from the analysis of affected families frequently allows the determination of an approximate genomic localization of the candidate disease gene with a precision of several millions of nucleotides. Once localized, the genetically defined chromosomal region is then recovered from genomic libraries as a contiguous set of genomic fragments. Genes residing in the disease-related region are determined by analysis of transcripts that are transcribed from the genomic fragment. From this analysis an initial set of candidate genes for a particular disease are identified based on the presence of the gene product in the biological system affected by disease and a correlation between its expression pattern and the pattern of disease progression.

Important information for selection of candidate genes also comes from analysis of their homology with genes known to be part of the same or related biological system. Finally, the ultimate proof of association between a gene and a genetic disorder comes from mutational analysis of a gene in patients affected by the disorder and from demonstration of a statistical correlation between occurrence of mutation and the disease phenotype.

Although positional cloning is a powerful method for gene discovery, the experimental method is extremely tedious and expensive. Moreover, disease genes implicated in genetically complex disorders, i.e., those controlled by multiple loci, can hardly be found using this strategy because of the complications associated with multiple loci linkage analysis.

Specialized databases for homology searches have also been utilized in disease gene discovery projects. In recent years a number of efficient sequence comparison tools have been developed such as the BLAST (Basic Local Alignment Search Tool) family of programs designed for comparison of a single "search sequence" with a database (see Altschul et al., 1990, J. Mol. Biol. 215:403-410; Altschul et al., 1997, Nucleic Acids Res. 25:3389-3402), the family of Hidden Markov Model methods for comparison of a set of aligned sequences that usually represent a protein motif or domain with a database (e.g., Krogh et al., 1994, J. Mol. Biol. 235: 1501-1531; Grundy et al., 1997, Biochem Biophys. Res. Commun. 231:760-6) and various other comparison tools (Wu et al., 1996, Comput. Appl. Biosci 12:109-118; Neuwald et al., 1995, Protein Sci. 4:1618-1632; Neuwald, 1997, Nucleic Acids Res. 25:1665-1677).

When used in disease gene discovery projects, homology searches can be enhanced by creating specialized databases that utilize statistical analysis for evaluating significance of sequence similarities in comparison of new sequences with a database of known sequence. Such databases are fine-tuned to the size of the database used (Altschul et al., 1990, J. Mol. Biol. 215:403-410; Altschul et al., 1997, Nucleic Acids Res. 25:3389-3402), so that the same level of homology between a search sequence and a database sequence can be determined to be highly significant if the search sequence is compared with a smaller database, or insignificant and thus undetectable, if the search sequence is compared with a larger database.

In alternatives to standard homology searches, in projects oriented towards gene discovery, researchers usually have some a priori knowledge about the set of genes/proteins that might display important similarity to the unknown new gene. Therefore, selecting an a priori defined set of genes/proteins for comparison with new experimental sequences is a feasible and useful strategy. This strategy was successfully applied to search for homologs of disease genes in yeast and nematode genomes by Mushegian et al. (1997, Proc. Natl. Acad. Sci USA 94:5831-5836).

Two homologous genes taken from different species that originate from the nearest common ancestor by speciation are referred to as orthologs, while any two genes that originate from a common ancestor via a series of events involving intragenomic duplications are called paralogs. Tatusov et al. (1994, Proc. Natl., Acad. Sci USA 91:12091-12095) describe comparisons of proteins encoded by the genomes of different phylogenetic lineages and elucidation of consistent patterns of sequence similarities permitting the delineation of clusters of orthologous groups (COGs). Each COG consists of individual orthologous genes or orthologous groups of paralogs from different phylogenetic lineages. Since orthologs typically have the same function, the classification of known genes and proteins into clusters of orthologous groups permits the assignment of a function to a newly discovered gene or protein by merely classifying it into a COG. Although Tatusov describes a method for assigning a function to a newly discovered gene, he does not describe a method for predicting the existence of undiscovered genes. In addition, Yuan, et al. attempted simultaneous reconstruction of a species tree and identification of paralogous groups of sequences and detection of orthologs in sequence databases (Yuan et al., 1998, *Bioinformatics* 143:285-289).

Other groups have aimed at capturing interactions among molecules through the use of programs designed to compare structures and functions of proteins (Kazic 1994, In: *Molecular Modeling: From Virtual Tools to Real Problems*, Kumosinski, T. and Liebman, M. N. (Eds.), American Chemical Society, Washington, D.C. pp. 486-494; Kazic, 1994, In: *New Data Challenges in Our Information Age* Glaesar, P. S. and Millward, M. T. L. (Eds.). Proceedings of the Thirteenth International CODATA Secretariat, Paris pp. C133-C140; Goto et al., 1997, Pac. Symp. Biocomput. p. 175-186; Bono et al., 1998, Genome Res. 8:203-210; Selkov et al., 1996, Nucleic Acids Res. 24:26-28). These projects are significantly different from the inventive methods described herein because they do not describe methods for deducing the existence of as yet unknown genes based on comparisons of regulatory pathways and gene structure between one or more species. The present invention provides a method for increasing the sensitivity of analysis methods through the generation of specialized databases.

3. SUMMARY OF THE INVENTION

In accordance with the present invention there is provided methods for identification of novel genes comprising (i) generating one or more specialized databases containing information on gene/protein structure, function and/or regulatory interactions; and (ii) searching the specialized databases for homology or for a particular motif and thereby identifying a putative novel gene of interest. The invention may further comprise performing simulation and hypothesis testing to identify or confirm that the putative gene is a novel gene of interest.

The invention is based, in part, on the observation that functionally similar regulatory systems are generated during evolution by genetic duplication of ancestral genes. Thus, by comparing phylogenetic trees or regulatory networks and identifying genes and/or proteins absent in one system under comparison, the existence of as yet unidentified genes and/or proteins can be predicted. To make meaningful comparisons of phylogenetic trees it is necessary to distinguish between orthologs and paralogs. The present invention provides a method useful for discriminating between orthologs and paralogs and inferring the existence of as yet unidentified genes and/or proteins.

The present invention relates to natural language processing and extraction of relational information associated with genes and proteins that are found in genomics journal articles. Specifically, the natural language processing system of the invention is used to parse the articles published in biological journals focusing on structure and interactions among genes and proteins followed by computer representation of such interactions.

In accordance with the present invention, specialized databases are developed that contain information on gene/protein structure and interactions based on information derived from preexisting databases and/or research articles including information on interactions among genes and proteins, their domain/motif structure and their subcellular and tissue expression/distribution patterns.

The invention relates to a sequence analysis program which utilizes the specialized database for comparison of a single sequence, processing the output into a sequence alignment, computing phylogenetic trees, and analyzing these trees to predict undiscovered genes. This program also includes a set of tools for generating motif/domain models from multiple sequence alignments of known genes and for using these models for extraction of structurally and/or functionally homologous sequences from databases which contain raw sequence data.

The invention further provides for a simulation and hypothesis testing program which relies on the specialized databases of gene/protein interactions for identifying potentially undiscovered members of multigene families through comparisons of regulatory networks for different species and testing hypotheses with regard to regulatory cascades. A comparison of homologous regulatory networks within the same organism and between different species of organisms will allow the identification of genes absent in one of the systems under comparison, thus providing a set of candidate genes. In this way, genes that contribute to the phenotype of a specific disease associated with a particular biological system under analysis may be identified, mapped and subjected to mutational analysis and functional studies.

4. BRIEF DESCRIPTION OF THE DRAWINGS

FIG. 4 shows a set of keywords defining proteins involved in apoptosis pathways, these keywords having been utilized for generating a specialized sequence database Apoptosis 3, this list having been compiled manually for testing the concept of specialized databases;

Figure 5:
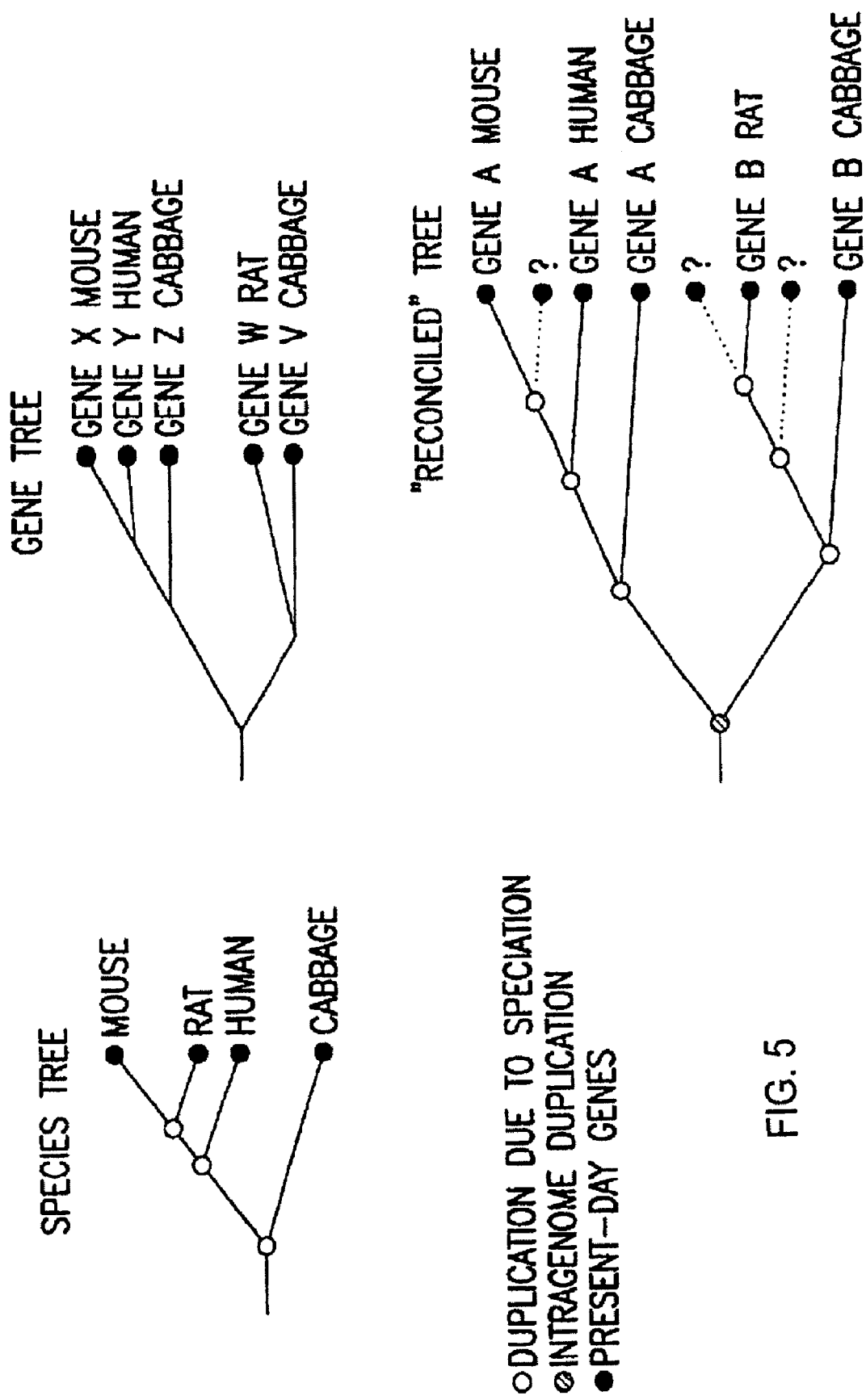
Figure 6A:
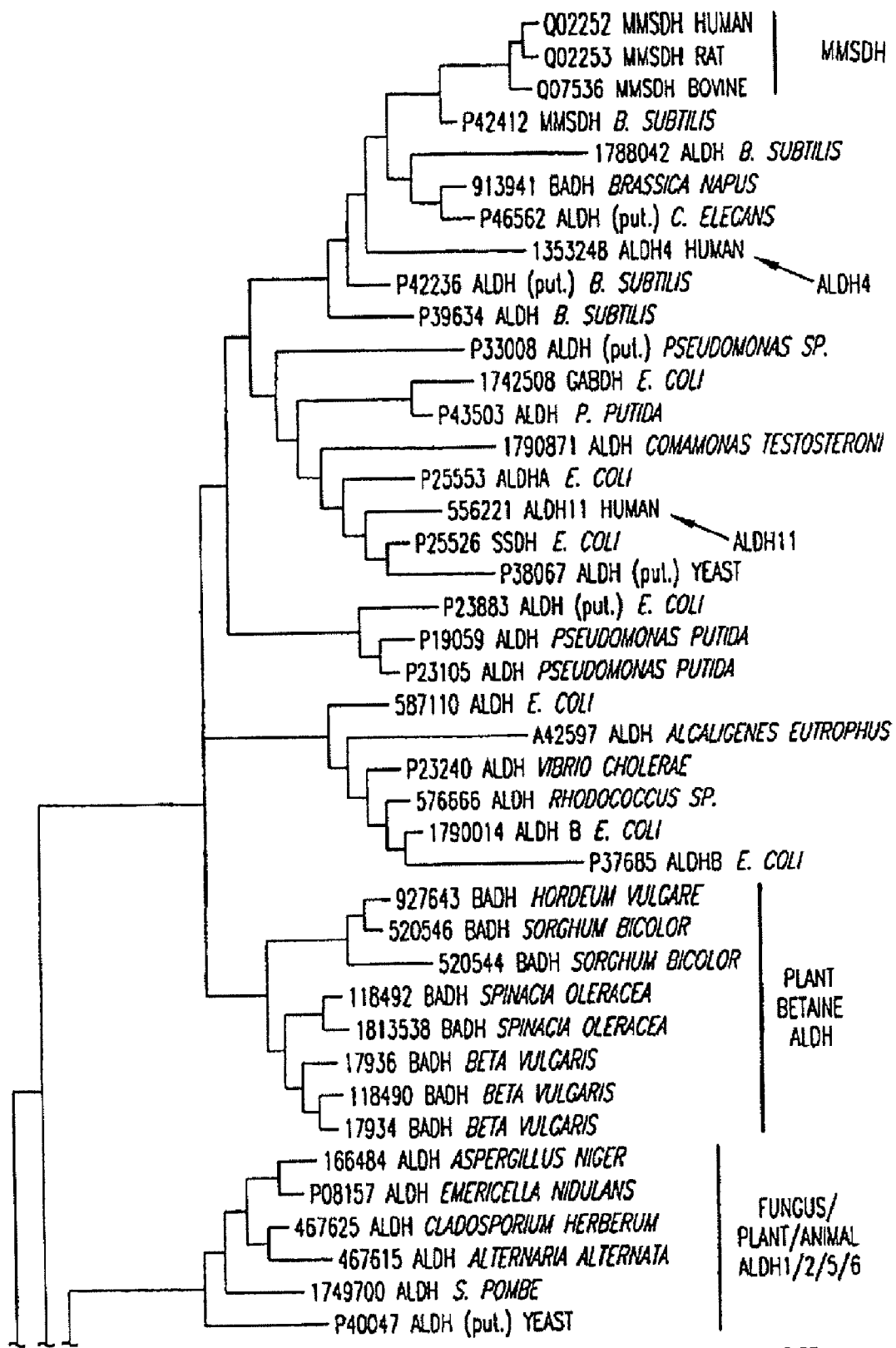
Figure 6B:
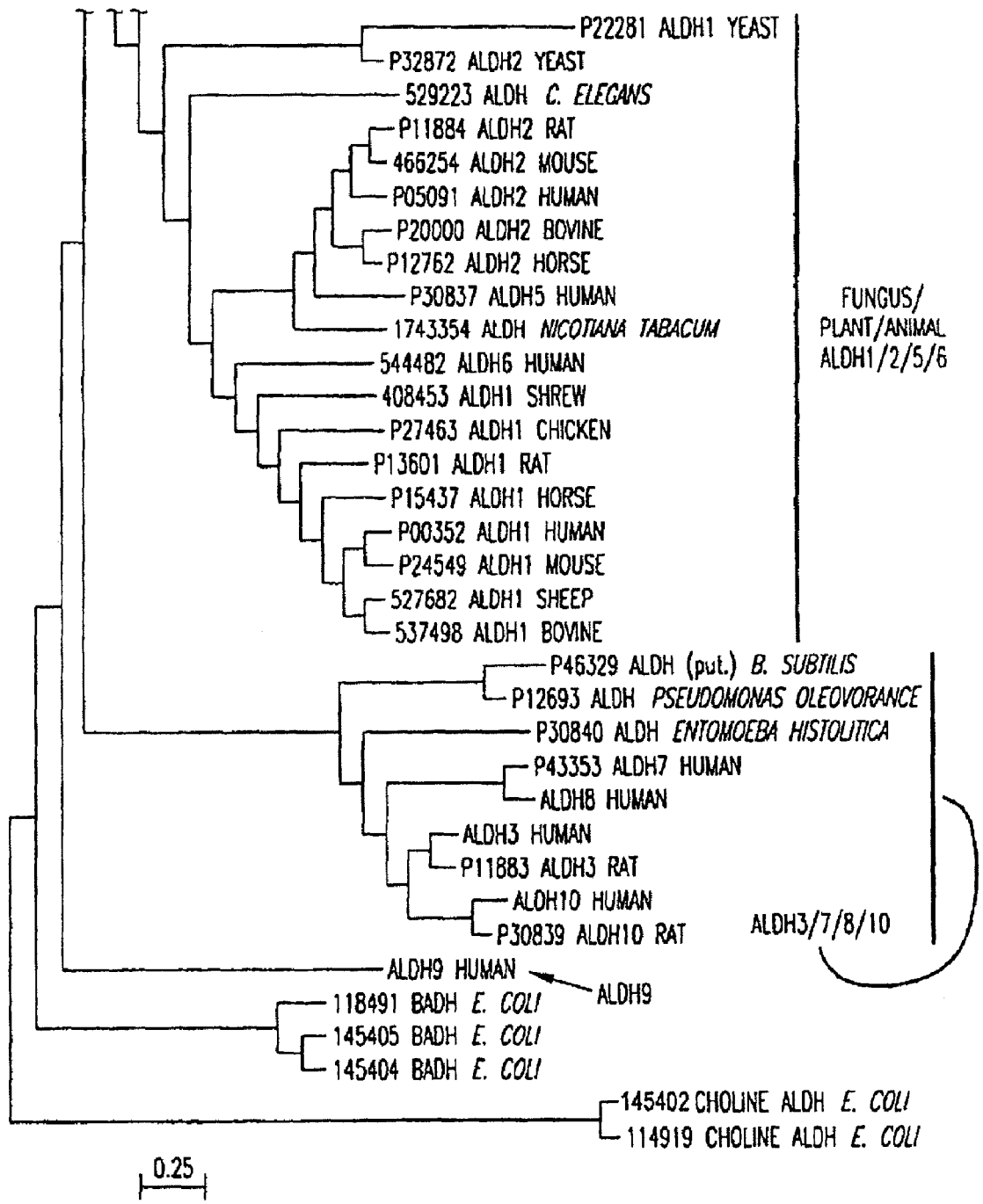
Figure 7A:
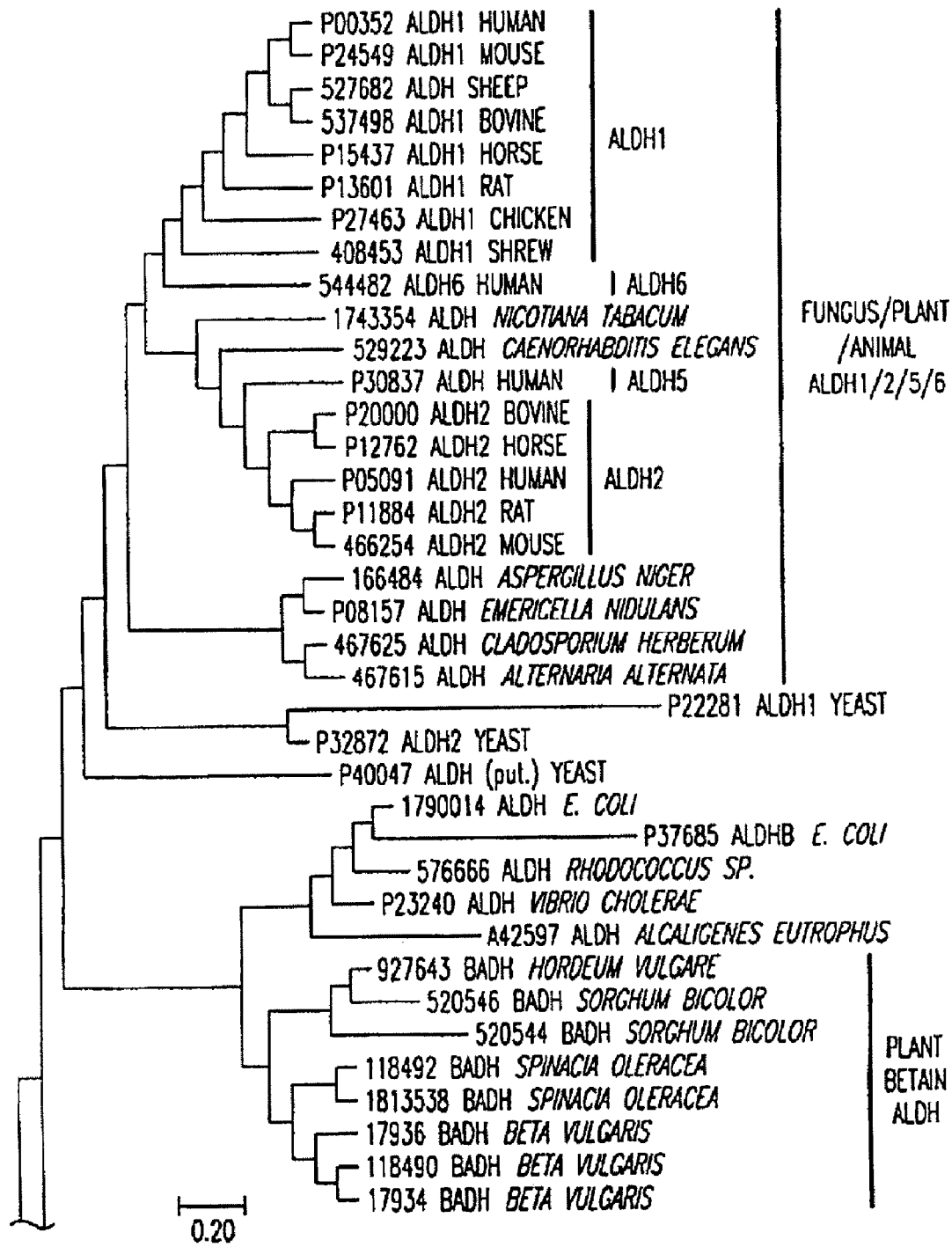
Figure 7B:
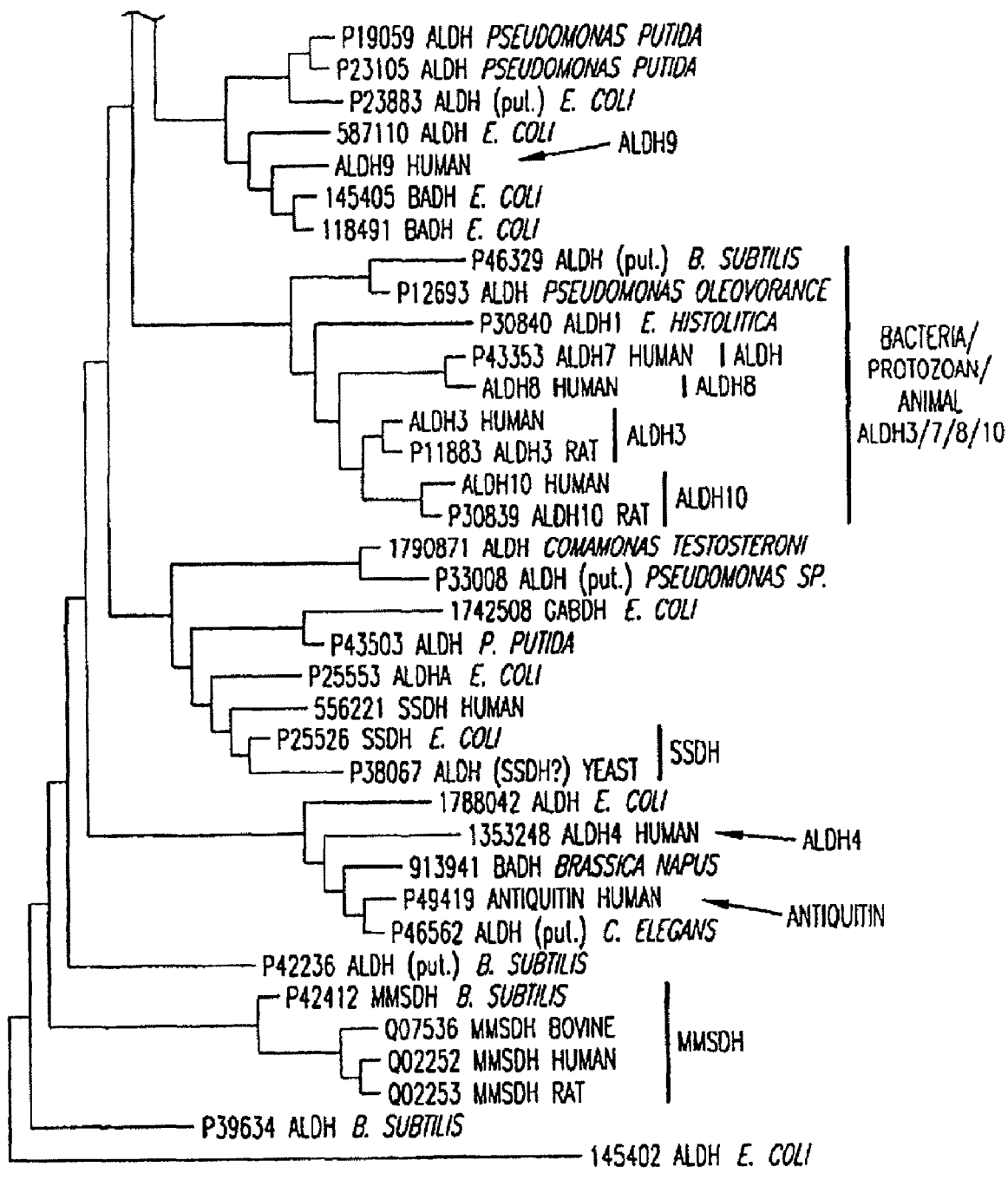
Figure 8:
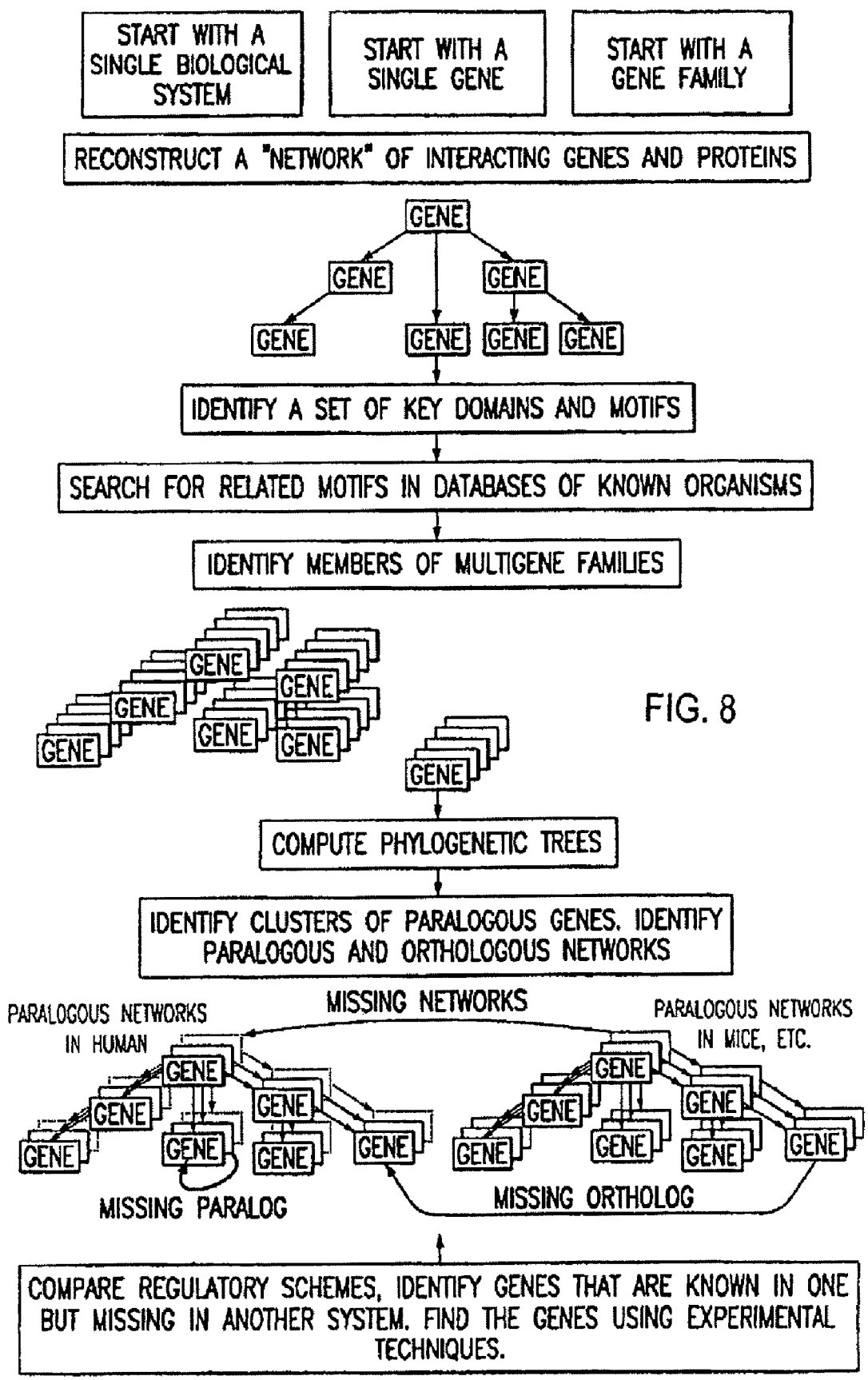
Figure 11A:
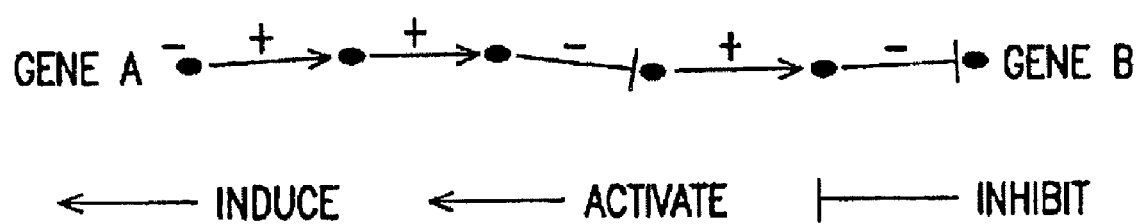
Figure 11B:
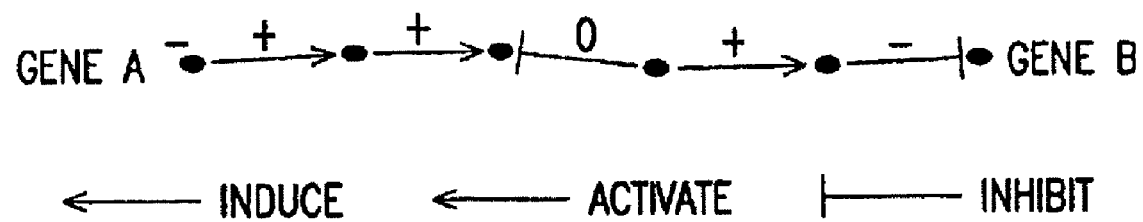
Figure 12:
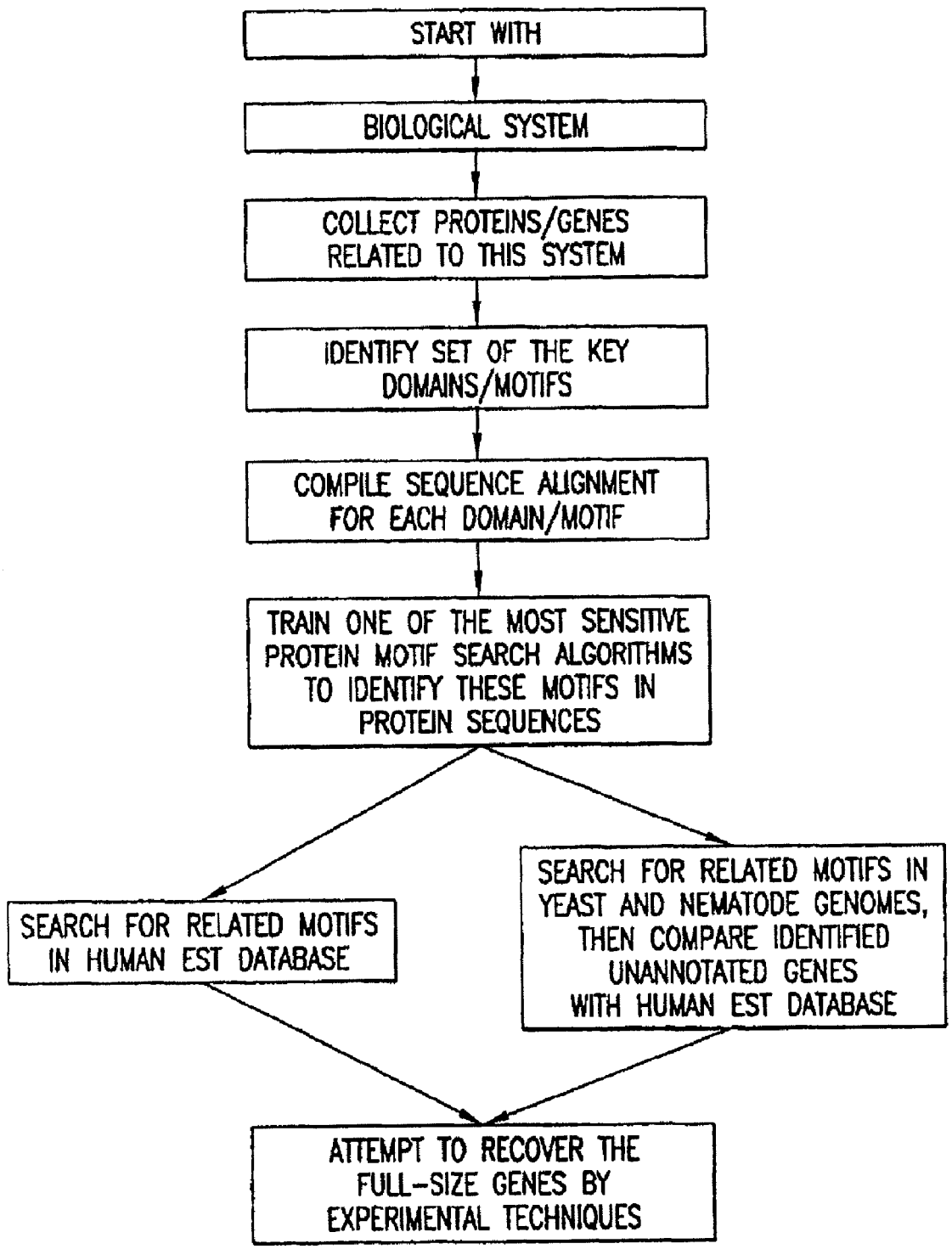
Figure 13B:
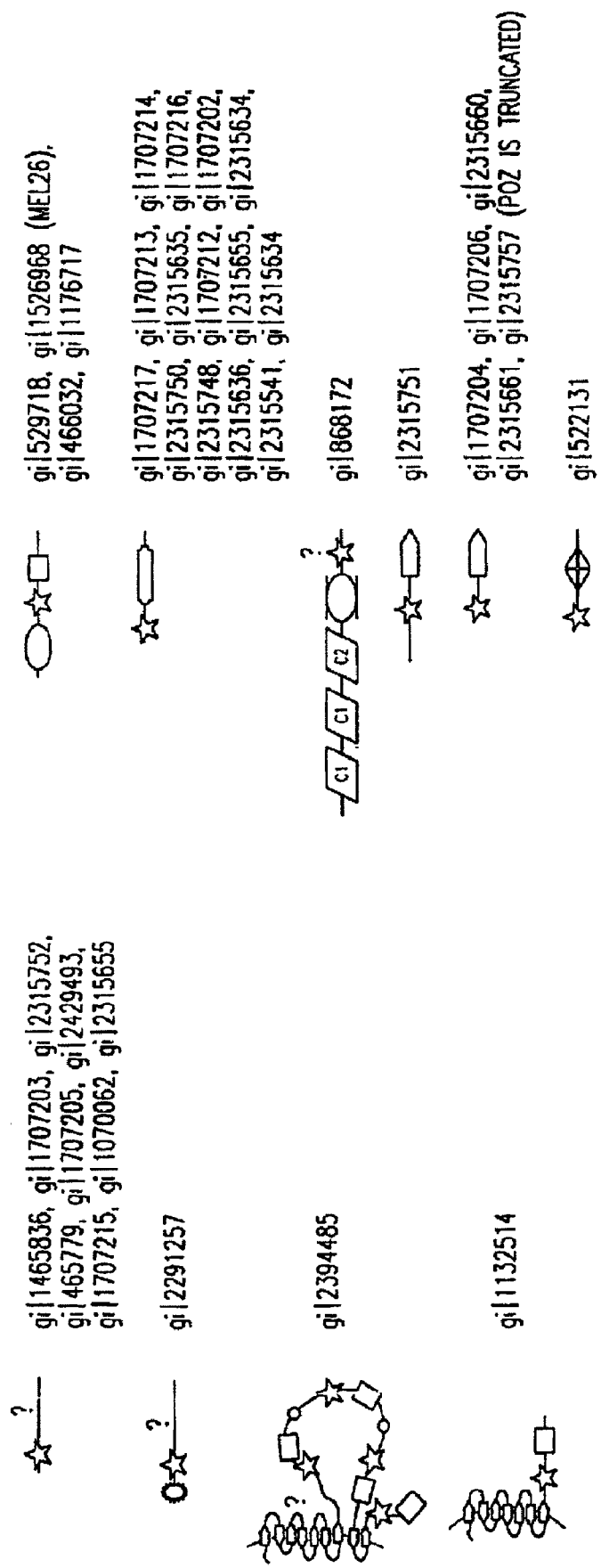
Figure 13C:
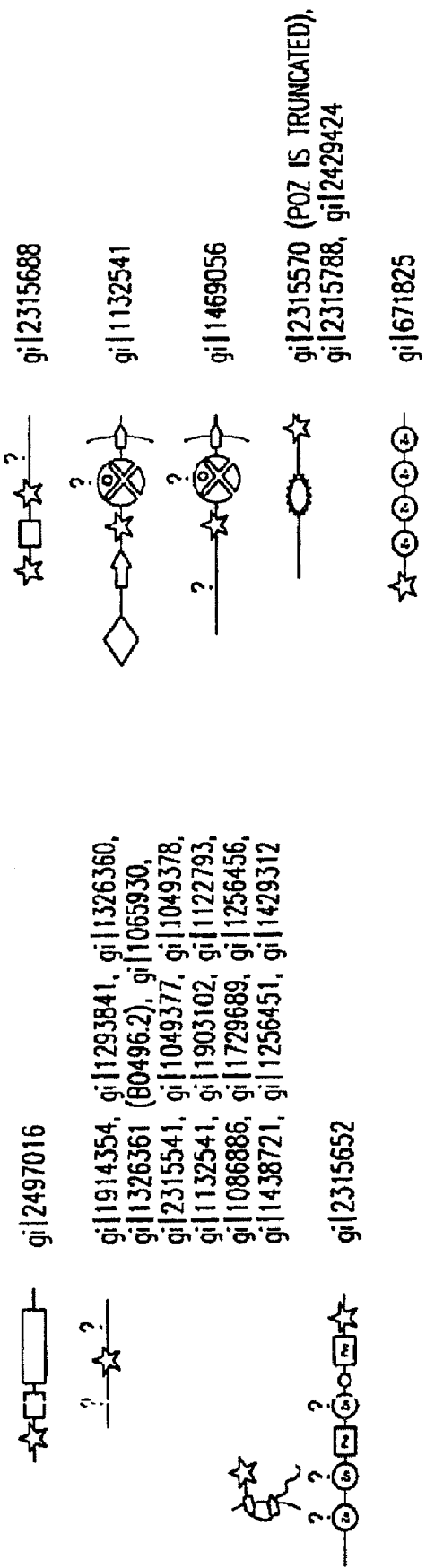

FIG. 5 shows a "species tree," which is a graph depicting the correct order of speciation events leading to a set of present day species; a "gene tree," which is a graph depicting a history of a few genes from the same species, where each species can be represented by multiple paralogous genes (because the set of known genes is incomplete for most genomes, and there are often multiple representations of the same gene family in the same genome, the gene tree can be drastically different from the corresponding species tree); and a "reconciled tree", which is the gene tree that would be obtained if gene deletions were completely forbidden and all genes were known for all species under analysis;

FIGS. 6A and 6B show the original tree of ALDH sequences, indicating sequence clusters where bacterial, plant, fungal and nematode orthologous genes are present, but a human ortholog was not yet known;

FIGS. 7A and 7B show the same phylogenetic tree as in FIGS. 6A and 6B with an additional human protein, referred to as antiquitin which was discovered by the method of the invention;

FIG. 8 is a schematic diagram illustrating functional network-based gene discovery in accordance with the present invention;

FIG. 9A presents diagrams depicting the regulatory relationships among hypothetical proteins (denoted with Arabic numerals) of hypothetical species A and B. Proteins in different species denoted with the same numeral are considered orthologous. The diagrams show that regulatory relationships between a pair of proteins can be of three different kinds;

FIG. 9B, 9C, and 9D are diagrams representing Boolean operations OR, AND, and XOR, on arcs of the two oriented graphs of FIG. 9A, the same operations being applicable to the set of vertices of the two oriented graphs;

FIG. 10 is a diagram representing a hypothetical example of defining homologous protein networks in two different species using protein motifs, the diagram showing only two hypothetical proteins (1 and 2) for species A and three hypothetical proteins (1, 3, and 4) for species B. Protein 1 in both species has motifs $\alpha$ and $\beta$, protein 2 has motifs $\delta$, $\epsilon$, and $\zeta$, and proteins 3 and 4 have motifs $\delta$ and $\zeta$, and $\epsilon$, respectively. The motif analysis can indicate that proteins 3 and 4 in species B may collectively perform the same function as protein 2 in species A;

FIG. 11A and 11B are diagrams respectively representing hypothetical examples of evaluating the impact of a "knockout" of hypothetical gene A on the expression of a hypothetical gene B. The effect of knock-out of gene A calculated by multiplication along the shortest pathway connecting genes A and B is inhibition of gene B, the resulting effect being zero if the orientation of only one arc in the same pathway is reversed;

FIG. 12 is a flow chart representing the scheme of gene discovery analysis involving motif/domain analysis in accordance with the present invention; and FIGS. 13A-C show the identification of genes in *C. elegans* containing either POZ or kelch domains. The protein excession numbers are indicated adjacent to the different protein domains. The protein corresponding to accession number gi/1132541 contains a POZ domain, death domain, kinase domain and heat repeat.

FIG. 14A. Two human sequences with the closest homology to the *C. elegans* sequence gi/1132541 (SEQ ID NO:5, SEQ ID NO:6).

Figure 14B:
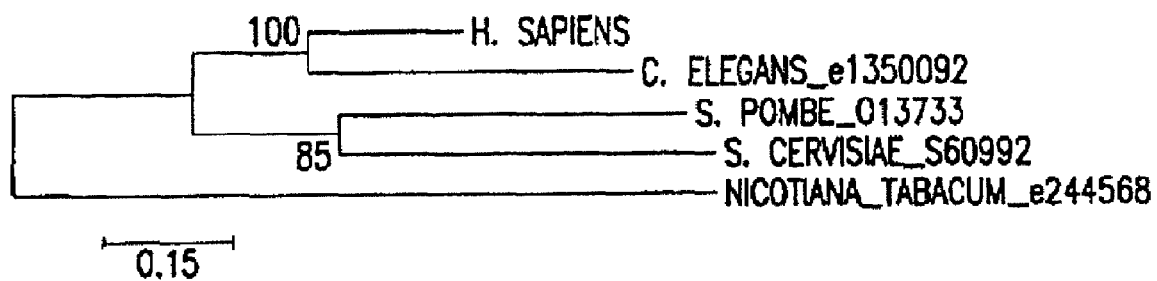

FIG. 14B. Computed gene tree indicating that the identified human gene represents an ortholog of the *C. elegans* gene gi/1132541.

FIG. 14C. Nucleotide sequence of the death domain gene (SEQ ID NO:7).

FIG. 14D. Deduced amino acid sequence of the death domain protein (SEQ ID NO:8).

FIG. 15. Identification of candidate gene implicated in the etiology of Chronic Lymphocytic Leukemia (CLL). Sequence homology between a CLL region open reading frame and mouse Rpt1 (sp/P15533/RPT1) is presented (SEQ ID NO:9; SEQ ID NO:10).

Figure 16A:
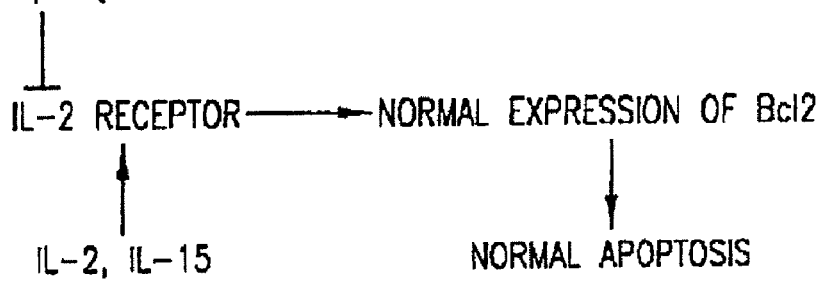
Figure 16B:
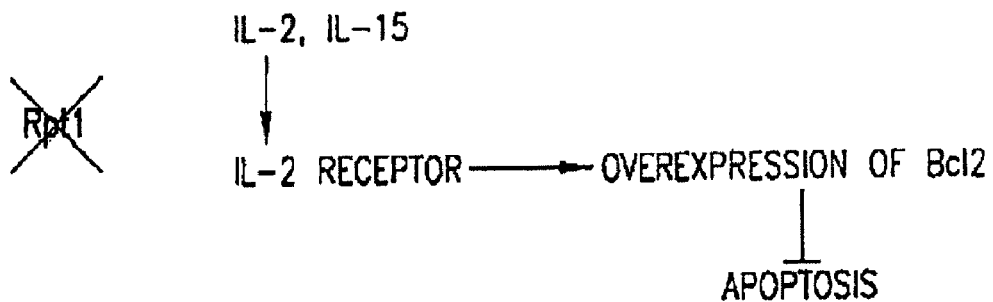

FIG. 16A-B. Model of regulatory functions of Rpt1. FIG. 16A indicates that in mouse T lymphocytes Rpt1 serves as a repressor of the gene for interleukin 2 receptor (IL-2R). FIG. 16B demonstrates that when Rpt1 is knocked out, the regulatory effect is manifested as a block of the apoptotic pathway for T-lymphocytes resulting in accumulation of T-lymphocytes in blood.

FIG. 17A. Two EST sequences identified by searching a protein dbEST using the mouse Mad3 protein as a query (SEQ ID NO:11; SEQ ID NO:12; SEQ ID NO:13; SEQ ID NO:14).

FIG. 17B. Nucleotide sequence of the human Mad3 gene (SEQ ID NO:15).

FIG. 17C. Complete sequence of the human Mad3 protein (SEQ ID NO:16). A search was conducted to identify overlapping sequences. The complete sequence of the gene was assembled and the amino acid sequence deduced. The translated human Mad3 sequence consists of 206 amino acid residues 81% of which are identical to the mouse Mad3 protein.

FIG. 17D. Multiple alignment of the human Mad3 amino acid sequence with known Mad proteins (SEQ ID NOS:17-22).

Figure 18A:
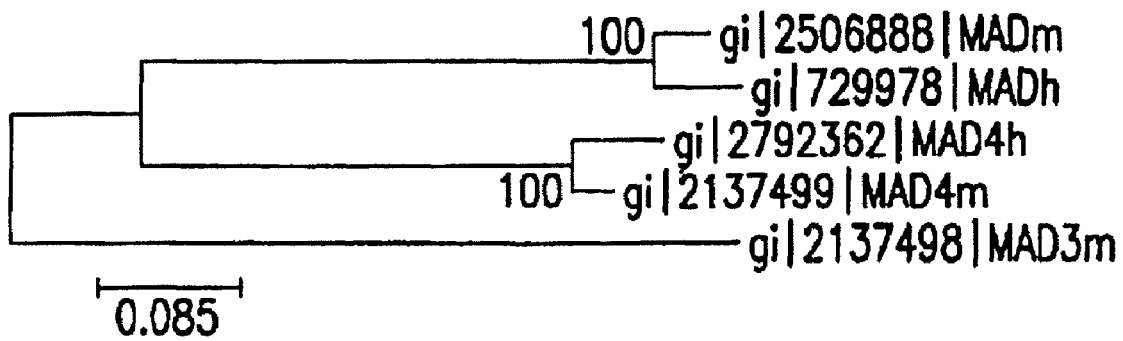

FIG. 18A. Phylogenetic tree indicating relationship between three known mouse Mad genes and their two human homologs.

Figure 18B:
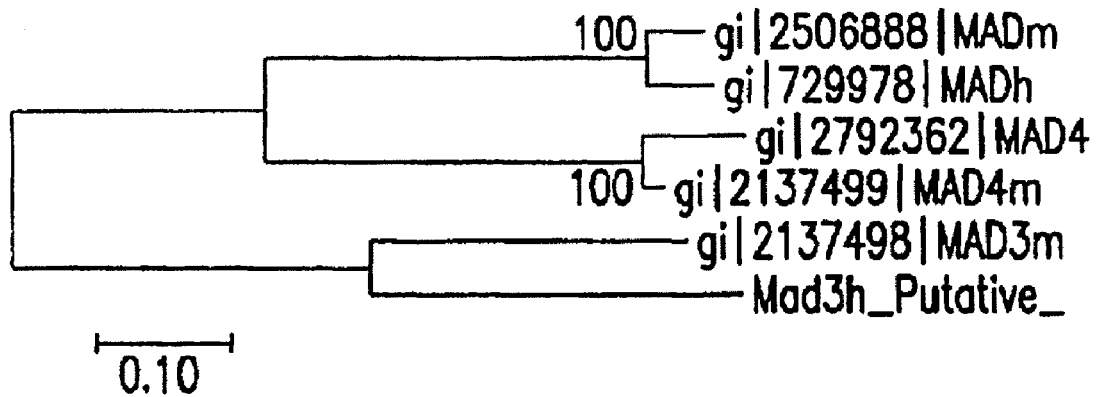

FIG. 18B. Phylogenetic tree including new human Mad3 sequence. The phylogenetic tree indicates that the new human gene belongs to the family of Mad proteins and is an ortholog of mouse Mad3.

5. DETAILED DESCRIPTION OF THE INVENTION

The present invention provides methods for identification of novel genes comprising: (i) generating specialized databases containing information on gene/protein structure, function and regulatory interactions and, (ii) sequence analysis which includes homology searches and motif analysis thereby identifying a putative novel gene of interest. The invention may further comprise performing simulation and hypothesis testing to identify or confirm that the putative gene is a novel gene of interest.

The specialized databases are constructed utilizing information concerning gene/protein structure or function derived from unpublished data, research articles and/or existing databases. The specialized databases can be used to identify novel genes by: (i) searching for motif/domain combinations characteristic for a putative gene of interest; (ii) phylogenetic tree analysis of homologous genes for predicting the existence of yet undiscovered genes; (iii) comparing members of interactive gene/protein networks from different species for predicting the existence of yet undiscovered genes; and (iv) testing a hypothesis with regard to known interactions of homologs from other species in regulatory pathways.

5.1. The Natural Language Processing

The present invention relates to a natural language processing system that is designed to parse the electronic versions of articles published in journals that report on structural interactions among genes and proteins. The system provides a method for extracting information on interactions among genes and proteins, their domain/motif structure, and/or their sub-cellular and tissue expression/distribution patterns, followed by computer representation of such information.

Figure 1:
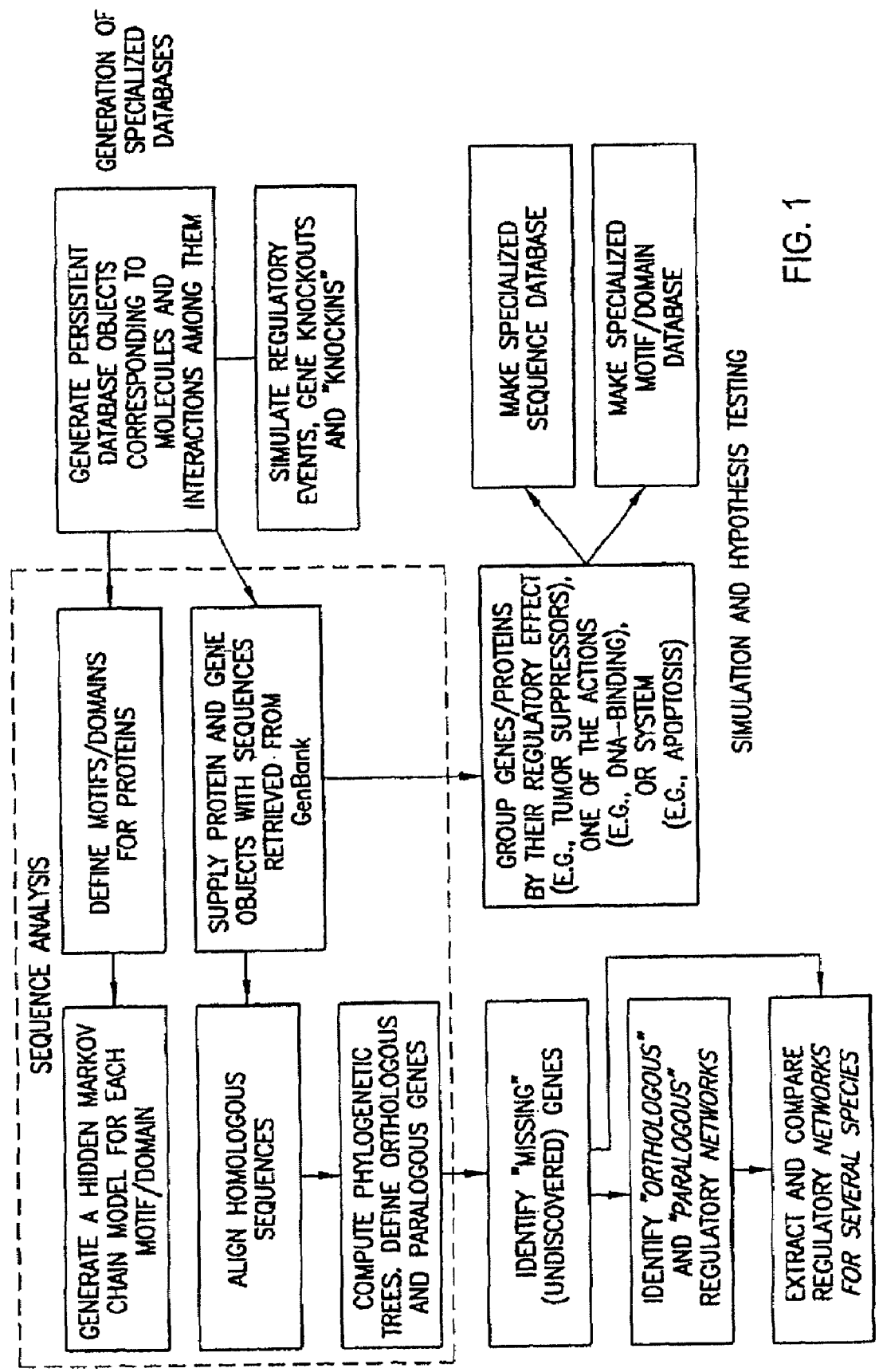
FIG. 1 is a block diagram illustrating the three major programs of the method according to the present invention: (i) the generation of specialized databases based on information on gene/protein structure, function and regulatory interactions derived from research papers and databases; (ii) sequence analysis; and (iii) simulation and hypothesis testing.
Figure 2:
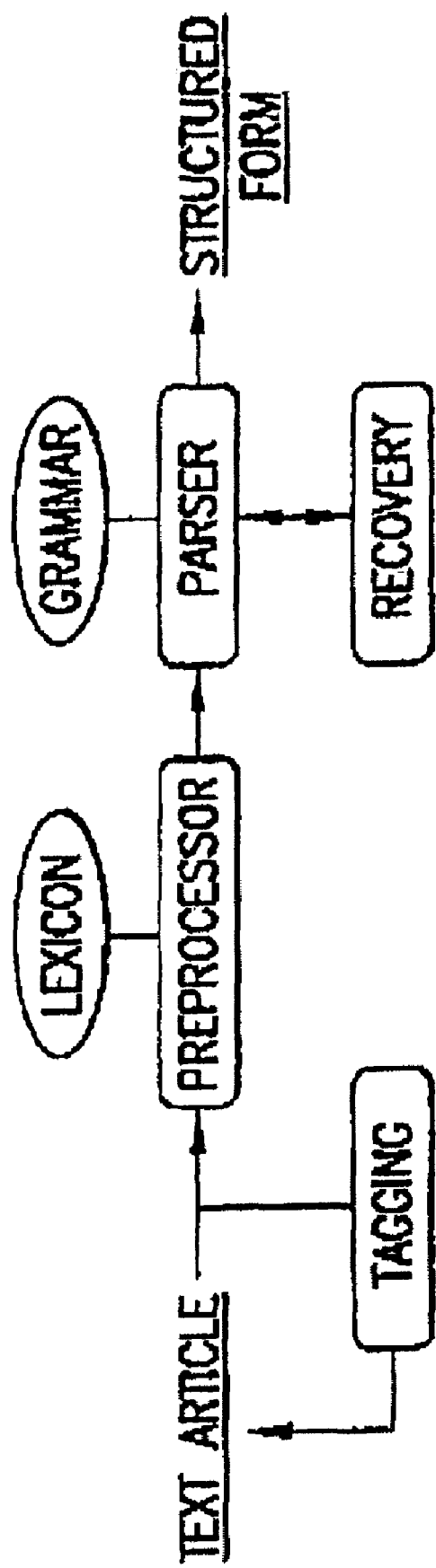
FIG. 2 is a block diagram of an information extraction system in accordance with a preferred embodiment of the present invention.

The general natural language-processing system of the invention is schematically depicted in FIG. 2. The collection phase automatically collects articles from appropriate literature, and selects articles that contain relevant information using Keyword search techniques. In the next phase, the preprocessor standardizes the selected articles so that they consist of tagged ASCII text where the tags delineate critical components of the article. The next phase, termed the extraction phase, retrieves and classifies biological entities, i.e., as names of proteins, genes and small molecules. In addition, the relationship extraction phase recovers structural relationships between the entities. This phase is followed by a phase which performs an analysis of the sequence of events.

The final phase of the system processes the output extracted from an article to remove redundancies, inconsistencies and to incorporate implicit information before adding the extracted knowledge consisting of biological entities, their attributes, conditional constraints, and relationships between them, for subsequent use in analysis and hypothesis testing. The information extraction system as depicted in FIG. 2, referred to herein as "GENIE," is designed for use as a general processor within the domain of genomics literature although the system may also be used in other specialized domains. GENIE is an adaptation of MedLEE developed for the medical domain. GENIE uses the same source code as MedLEE but the Lexicons and grammar were adapted for genomics literature.

The information extraction system of the present invention is described below, by way of example, with reference to the genomics domain uses of GENIE. It is written in Quintus Prolog and uses the Unix or Windows operating systems, as described in detail below.

A natural-language phrase included in text document is understood as a delimited string comprising natural-language terms or words. The string is computer readable as obtained, e.g., from a pre-existing database, a keyboard input, optical scanning of typed or handwritten text, or processed voice input. The delimiter may be a period, a semicolon, an end-of-message signal, a new-paragraph signal, or any other suitable symbol recognizable for this purpose. Within the phrase, the terms may be separated by another type of delimiter such as a blank or another suitable symbol.

As a result of phrase parsing, terms in a natural-language phrase are classified, (e.g., as referring to a gene, a protein, or their interactions) and the relationships between the interactions are established and represented in a standard form. For example, in the sentence "Rap inhibited fyn", the structured form would be:

[action,inactivate, [protein,rap], [protein,fyn]].

In such an example, the interaction is "inactivate", the agent is "Rap" and the target is "fyn." More complex sentences consisting of nested relationships, such as "The activation of BAD was suppressed by the phosphorylation of JNK" can also be parsed and represented appropriately. The structured output form for this sentence would be: [action,inactivate, [action,phosphorylate,x,[protein,jnk],[action,activate,x, [protein,bad]] In the first example, the primary interaction is "inactivate"; in the second example, an interaction "phosphorylate" is the agent where the protein "jnk" is its target (the agent of "phosyphorylate" in not specified and thus is represented as "x"). In this example, the target of "inactivate" is also an interaction "activate" where the target is the protein "bad" and the agent is unknown.

While parsing is based on both syntactic and semantic grammatical patterns, the substances in a domain are normally only semantic categories such as "protein", "gene", and "small molecule." There are no corresponding syntactic categories needed for these substances because they are normally all nouns. However, each action can be categorized both semantically and syntactically. An action, which is a semantic category, can generally occur syntactically as a verb "inactivate" or as a noun "inactivation." Therefore there are two sets of lexical entries for the actions: syntactic and semantic. The syntactic lexicon for actions specifies the main syntactic category such as "v" for verb, "ving" for progressive form of verb, and "activation" for noun. The semantic entries for actions not only categorize the actions, but also specify features for each action. For example, one feature provides the number of arguments that are expected for the action, i.e., some actions are associated with two arguments because they have an agent and a target as "inactivate", and others just have an agent "mutate." The lexicon of substances and structures appears as Appendix A; the syntactic lexicon for actions appears as Appendix B; and the semantic lexicon of actions appears as Appendix C.

A second feature specifies whether or not the arguments should be reversed when obtaining the target form. For example the arguments of "attributable to" should be reversed, i.e., in "the phosphorylation of jnk is attributable to the activation of bad", the underlying action is "cause" (from "attributable to", the agent is the "activation of bad" and the target is "the phoshorylation of jnk"), whereas the arguments of "activates" is not (i.e. in "jnk activates bad", the agent is "jnk" and the target is "bad").

FIG. 2 shows a preprocessor module of GENIE by which natural-language input text is received. The preprocessor thus performs lexical lookup to identify and categorize multi-word and single word phases within each sentence. The output of this component consists of a list of word elements where each element is associated with a word or multi-word phrase in the report. For example, assuming that the sentence "bad functions as a negative regulator of the activation of jnk" is at the beginning of the report, it would be represented as a list of elements where each element is a word or phrase. For example, element 1 is associated with "bad", element 2 with the multi-word phrase "functions as a negative regulator of", element 8 with "the", and element 9 with "activation". The remainder of the list of word positions would be associated with the remaining words in the report. Some of the phrases may not need lexical lookup because they already have been tagged by a previous component. Such a tagging system is described below in Section 5.2.

The second component of the GENIE system is the parser. It utilizes the grammar and categories assigned to the phrases of a sentence to recognize well-formed syntactic and semantic patterns in the sentence and to generate structured output forms. The parser proceeds by starting at the beginning of the sentence element list and following the grammar rules. When a semantic or syntactic category is reached in the grammar, the lexical item corresponding to the next available unmatched element is obtained and its corresponding lexical definition is checked to see whether or not it matches the grammar category. If it does match, the word or phrase is removed from the unmatched sentence list, and the parsing proceeds. If a match is not obtained, an alternative grammar rule is tried. If no analysis can be obtained, an error recovery procedure is followed so that a partial analysis is attempted. The actual grammar used for GENIE appears as Appendix D.

The parser module of GENIE uses the lexicon, and a grammar module to generate target forms. Thus, in addition to parsing of complete phrases, subphrase parsing can be used to an advantage where highest accuracy is not required. In case a phrase cannot be parsed in its entirety, one or several attempts can be made to parse a portion of the phrase for obtaining useful information in spite of a possible loss of information.

Conveniently, each module is software-implemented and stored in random-access memory of a suitable computer, e.g., a work-station computer. The software can be in the form of executable object code, obtained, e.g., by compiling from source code. Source code interpretation is not precluded. Source code can be in the form of sequence-controlled instructions as in Fortran, Pascal or "C", for example. Alternatively, a rule-based system can be used such a Prolog, where suitable sequencing is chosen by the system at run-time.

An illustrative portion of the GENIE system is shown in the Appendix D in the form of a Prolog source listing with comments. The following is further to the comments.

Process_sents with get_inputsents, process_sects and outputresults reads in an input stream, processes sections of the input stream according to parameter settings, and produces output according to the settings, respectively. Among parameters supplied to Process_sents are the following: Mode (specifying the parsing mode) and Protocol (html or plain). Process_sents is called by another predicate, after user-specified parameters have been processed.

The parsing modes are selected by GENIE so as to parse a sentence or phrase structure using a grammar that includes one or more patterns of semantic and syntactic categories that are well-formed. For example, for the phrase "bad inactivates jnk", a legitimate pattern can be substance1 action substance2, wherein substance1=protein bad, action="inactivates" and substance2="jnk." However, if parsing fails, various error recovery modes are utilized in order to achieve robustness. The error recovery techniques use methods such as segmenting the sentence, processing large chunks of the sentence, and processing local phrases. Each recovery technique is likely to increase sensitivity but decrease specificity and precision. Sensitivity is the performance measure equal to the true positive rate of the natural language processing, i.e., the ratio of information extracted by the natural language processing system that should have been extracted. Specificity is the performance measure equal to the true negative information rate of the system, i.e., the ratio of information not extracted by the NLP system that should not have been extracted. Precision is the reliability of the system, i.e., the ratio of information extracted correctly compared to all the information that was extracted. In processing a report, the most specific mode is attempted first, and successive less specific modes are used only if needed.

In accordance with the preferred embodiments of the present invention, the parser of FIG. 2 includes five parsing modes, Modes 1 through 5, for parsing sentences or phrases. Nominally, the parser is configured to first select Mode 1. If Mode 1 is not possible, the program continues with Mode 2 and so forth until parsing is complete. With Mode 1, the initial segment is the entire sentence and all words in the segment must be defined. This mode requires a well-formed pattern for the complete segment.

Mode 2 requires that the sentence or phrase be segmented at certain types of words or phrases, e.g., "is attributable to." Here, an attempt is made to recognize each segment independently, i.e., a first segment ending with the word "is" and a second segment beginning with the word after "to." The segmenting process is repeated until an analysis of each segment is obtained or until segmenting is no longer possible.

Mode 3 requires a well-formed pattern for the "largest" prefix of the segment, i.e., usually at the beginning of the segment. This occurs when a sentence contains a pattern at the end which is not in the grammar but a beginning portion that is included. For example, in "bad inactivates jnk at this time", the beginning of the sentence "bad inactivates jnk" will be parsed and the remainder will be skipped.

Mode 4 requires that undefined words be skipped and an analysis be attempted in accordance with Mode 1. Mode 4 is useful where there are typographical errors and unknown words. For example, in the phrase "abc bad inactivates jnk", the word abc is unknown to the system and will be ignored but the remainder of the phrase will be parsed.

Mode 5 first requires that the first word or phrase in the segment associated with an action be found. Next, an attempt is made to recognize the phrase starting with the leftmost recognizable argument. For example, in "during bad inactivates jnk on the fifth day," the phrase "bad inactivates jnk" will be parsed and the remaining words will not be. If no analysis is found, recognition is retried at the next possible argument to the right. This process continues until an analysis is found.

Process_sects with get_section and parse_sentences gets each section and generates intermediate output for the sentences in each section.

Write produces the output as a list consisting of relations and interactions

Setargs sets arguments or parameter values based on user input or by default.

The structured output generated by the GENIE program uses a frame-based representation. Each frame specifies the informational type, the value, and arguments or modifier slots which are also frames. Consider the text data input "bad inactivates the phosphorylation of jnk." A corresponding output, as shown below, is a frame denoting an action, which has the value inactivate; in addition, there are two arguments. The first argument is a protein bad and the second argument is an action with the value phosphorylate, which has two arguments. The first argument is x signifying that the agent has not been specified; the second argument is a protein with the value jnk. The second argument is the target:

[action,inactive, [protein,bad], [action,phosphorylate,x, [protein,jnk

In summary, a computer system has been disclosed that generates structured information concerning protein and gene interactions and relationships.

5.2. Use of BLAST for Finding Gene and Protein Names in Journal Articles

In a specific embodiment of the invention, an exhaustive list of gene and protein names, extracted from GeneBank, is translated into a different alphabet system by substituting each character in the name with a predetermined unique nucleotide combination. The encoded names are then imported into the BLAST database using the FASTA format. The scientific journals are translated, using the same nucleotide combinations, into a continuous string of nucleotides. A query is then used to match the translated journals against the nucleotide representation of gene and protein names in the BLAST database. Significant alignments associated with gene and protein names are listed in the BLAST output file, which is subsequently processed using Perl-scripts. The final result consists of the original journal article with XML tags surrounding the gene and protein names.

To adapt the problem to BLAST's statistical foundation, different measures were undertaken to limit the output to the most relevant gene and protein names. In addition, in order to fine-tune the matching process, different BLAST parameters were adjusted, such as the word size (which sets the size of the high scoring words, thus influencing the sensitivity of finding HSPs) and mismatch penalty (exact vs approximate matching).

In a specific embodiment of the invention, gene and protein names are extracted from GeneBank's gene symbol index file. The following is an excerpt of the file after discarding entries that are either composed of only numbers or of less than two alphabetic letters:

gfap gamma
hox a10
hox a1
wac 3'-end
pit-1/ghf-1 variant
[Y]

This list of gene and protein names is translated into a different alphabet system by substituting each character in the name with a predetermined unique nucleotide combination. The conversion chart is listed in Appendix E. The encoded names are then imported into the BLAST database using the FASTA format. For example, the first entry in the list above is "gfap gamma." After translation using the conversion chart, the same name appears as follows:

(SEQ ID NO: 1)
AGCAACTAAACACCCATCCAAGCAAACACACACACAAAC

Thus, the complete FASTA entry looks like this:

>gi|1 species,gp,gfap gamma
(SEQ ID NO: 2)
AAGCAACTAAACACCCATCCAAGCAAACACACACACAAAC In FASTA, the definition line (marked with '>') contains information about the database entry. This line can contain any kind of information. The information important for this particular example is the third entry in the definition line, 'gp', that specifies that the name can represent a gene or a protein. If the name is unambigous, then the definition line states that the name is only associated with a gene ('g') or protein ('p'). The fourth entry in the definition line is the name of the protein or gene, "gfap gamma" in this case.

The second line in the FASTA format normally contains the actual sequence of the protein/gene. In the example presented, the second line contains the translated protein or gene name.

All gene and protein names are translated into the nucleotide representation and converted into the FASTA format. Then, the database containing these FASTA entries are specially compiled for use in BLAST queries using a program that is included in the BLAST package called "formatdb".

Thus, the scientific journals are translated, using the same nucleotide combinations, into a continuous string of nucleotides. For example, the sentence "In the absence of costimulation, T cells activated through their antigen Y" is translated into "AAGTACAGATCCACGGAAGGAACGATCCAAACAAAGACGCAACGACAGAA ATAACGATCCACATAACTATCCAAATACATACGCACGGAAGTACACACGTAA TTAAACACGGAAGTACATACAGATCCATCCACGGATCCAAATAACGAATTAA TTACGCATCCAAACAAATACGGAAGTACTCAAACACGGAACGAACCATCCAC GGAAGGACCTACATACGTAAGCAAGGATCCACGGAAGGAACGAAGTACCTA TCCAAACACAGACGGAAGTAAGCAACGACAGATCC" (SEQ ID NO:3).

A query is then used to match the translated journals against the nucleotide representation of gene and protein names in the BLAST database. The query is executed using the blastall program that is included in the BLAST package. The query line looks like:

blastall -p blastn -d FASTA.dat -i query.txt

The flag 'p' denotes the sub-program (blastn is a sub-program of blastall that performs nucleotide matches), 'd' denotes the file that contains the FASTA entries and 'i' denotes the translated query text.

Significant alignments associated with gene and protein names are listed in the BLAST output file. This is an excerpt from a BLAST output file:

gi|63624 species,gp,ner
Length=12
Score=24.4 bits (12), Expect=3e-05
Identities=12/12 (100%)
Strand=Plus/Plus
Query: 729 acagaacgacct 740
Sbjct: 1 acagaacgacct 12

The first line denotes the database entry. The second line denotes the database sequence length, followed by the alignment score and the E-value. The next line indicates paired matches, mismatches and gapped alignment (the latter two are not shown in this example). The lines 'Query' and 'Sbjct' show the actual alignment between the query and database sequence. This output file is subsequently processed using a Perl-script (see Appendix F). The script shown in Appendix G scans the output file, which is sometimes several megabytes long, for any segments that start at position 1 of the database sequence (thus disregarding any segments that are only part of the sequence). In addition, the script allows for 10% mismatches between the aligned sequences for long sequences (as shown in the script of Appendix E), or 0% mismatches for short sequences. After scanning the output file, an intermediary file that lists the candidate sequences is created:

tran|365|381|gp|18493
tran|1|17|gp|18493
peci|549|565|gp|58106
il-2|621|637|gp|82396
il-2|325|341|gp|82396
gati|193|209|gp|92088
prod|641|657|gp|52292
rap1|105|121|gp|49898
spec|545|561|gp|33 183
crip|385|401|gp|18905
crip|21|37|gp|118905
as|161|177|gp|133961
her|65|77|gp|88411

The intermediary file lists the name of the sequence, followed by the starting and end point in the query sequence (corresponds to where the two sequences matched), the semantic class of the name (protein, gene or protein/gene). The last number is not considered.

The intermediary file is then scanned by another Perl program (Appendix G). This program compares the starting end points with the actual text, making sure that the matched name is an 'autonomous' entity in the query text. For example, while "per" in "per gene" should be recognized as a gene name, "per" in "personal" should not be recognized as a gene name. The program recognizes other characters than the space character delimiting an 'autonomous' gene or protein name. In addition, the script looks for plurals of words. For example, "interleukins" should be recognized as a protein name, although only the singular form, "interleukin", is in the database.

The final result consists of the original journal article with XML tags surrounding the gene and protein names. This is done using the same script as in Appendix G:

blocked <phr sem="gp">T cell antigen receptor</phr> (TCR)- and <phr sem="gp">CD28</phr>-mediated <phr sem="gp">IL-2</phr> gene transcription. Therefore, <phr sem="gp">Rap1</phr> functions as a negative regulator of Y To adapt the problem to BLAST's statistical foundation, different measures were undertaken to limit the output to the most relevant gene and protein names.

BLAST is sensitive to the search space the program works in. Thus, given a long query sequence and a large sequence database, matches have a lower statistical significance because the chances are higher that the matches could have occurred by chance alone. In addition, matches with few letters have a lower statistical significance than matches with many letters. In order to find all true matches with any significance level, some measures were undertaken to address this problem. For example, (i) the query sequence was divided into 10 equal length parts, i.e., the journal article was divided into 10 parts and 10 different queries are run on each part separately; (ii) the sequence database (with the gene and protein names) is separated into 5 databases, each containing protein/gene names of different length; (iii) gene and protein names with less than 3 letters in the database were 'expanded', i.e., spaces were added at the beginning and the end of the name. Doing so, the statistical significance of a match containing a short name was higher. A space does not only include an empty character. For example, a gene name "k4" could occur in a journal article as "kinin 4 (k4)". It was therefore important to define several characters as substitutes for a space character. The alphabet in Appendix E defines the nucleotide combination ATCC as such a substitute.

Working with nucleotides implies that errors involving reading frames must be addressed. For example, working with a code of four letters, the nucleotide combination ATCTGTCACG (SEQ ID NO:4) could mean ATCT/GTCA or TCTG/TCAC or CTGT/CACG. Since the text is translated into a nucleotide combination, only one of these possibilities is correct. But BLAST can not distinguish between these solutions, i.e., BLAST would potentially match a database sequence to a wrong reading frame in the query sequence, producing many nonsense results that could compromise the significance of true results.

The solution to this problem is a comma-free code. A comma free code knows only one correct reading frame. BLAST therefore does not produce any nonsense results. A comma-free code consists of only one permutation of a nucleotide combination. For example, given the nucleotide combination ATCC and its permutations CATC, CCAT and TCCA, only ONE of these permutations would be included in a comma-free code. The code in Appendix E does represent a comma free code. Comma-free codes were discussed in the early days of DNA research (Crick et al., Proc. Natl. Acad. Sci. 43:416-421).

In order to fine-tune the matching process, different BLAST parameters must be adjusted, for example: word size (which sets the size of the high scoring words, thus influencing the sensitivity of finding HSPs); mismatch penalty (exact vs approximate matching); numbers of alignments to show (true matches of low significance can sometimes be at the very end of the BLAST output, therefore many alignments have to be shown); and expectation value (which sets the significance value for matches in the output file).

5.3. Generation of Specialized Databases

In accordance with the present invention, specialized databases may be developed that contain information derived from unpublished data, publications such as research articles, theses, posters, abstracts, etc. and/or databases concerning interactions among genes and proteins, their domain/motif structure, and their biological functions.

For example, but not by way of limitation, a specialized database may be prepared as follows. Protein and gene sequences may be provided, for example, by the Java program PsiRetrieve which allows for quick retrieval of protein or nucleotide sequences from binary BLAST databases by sequence accession number, keyword or groups of keywords, or species name. In addition, using the program PsiRetriever, sequences encoding the proteins of interest may be retrieved from the non-redundant (NCBI) database of protein sequences and stored as a FASTA file. The FASTA file is then converted into a binary blast database using the program FORMATDB from the BLAST suit of programs.

Known motifs/domains for proteins may also be collected using the flat file versions of major protein databases, such as SWISS-PROT and the non-redundant database of NCBI. The databases can be downloaded and searched for the keywords "motif" and "domain" in the feature tables of proteins. In addition, existing databases of motifs and domains, such as BLOCKS and pfam, can be downloaded (Henikoff et al., 1991, NAR 19:6565-6572). Still farther, it is understood that any publically available database containing gene/protein sequences may be utilized to generate the specialized databases for use in the practice of the present invention.

Homologous sequences may be aligned using, for example, the CLUSTALW program (Higgins, et al. 1996 Methods in Enzymology 266: 383-402). A protein's sequence corresponding to each domain/motif can be identified, saved and used for building a Hidden Markov Model (HMM) of the domain/motif using a HMMER and HMMER2 packages (see, Durbin, R. et al. 1998 in Biological Sequence Analysis: Probablistic Models of Proteins and Nucleic Acids). HMMER and HMMER2 packages are useful for (i) building HMMs from sets of aligned protein or nucleotide sequences, and (ii) comparing the HMMs with sequence databases aimed at identifying significant similarities of HMMs with database sequences. Both nucleotide and protein databases can be used for this purpose. Alternatives to the Hidden Markov Model method for building domain/motif models include neural network motif analysis (Wu, C. H. et al., 1996, Comput Appl Biosci 12, 109-18; Hirst, J. D., 1991, Protein Eng 4:615-23) and positional weight matrix analysis (Claverie, J. M., 1994, Comput Chem 18:287-94; Venezia, D., 1993, Comput Appl Biosci 9:65-9; Bucher, P. 1996, Comput Chem, 20:3-23; Tatusov, R. L., 1994, Proc Natl Acad Sci USA 91:12091-5).

Once a comprehensive collection of motifs/domains is created, each particular protein may be compared against a complete database of HMMs to identify known motifs and domains. The Hidden Markov Model (HMM) is built using the following steps:

A1. Start with a motif/domain name and a single amino acid sequence representing a domain or motif.
A2. Do PSI-BLAST (BLASTPGP) search with the motif/domain sequence against a protein non-redundant database.
A3. Retrieve the sequences identified in the database search from the protein sequence database. Exclude low-complexity sequences, short or incomplete sequences and sequences with similarity score above a selected threshold of PPD value <0.001
A4. Align the set of sequences with CLUSTALW (or other multiple sequence alignment program).
A5. Use the set of aligned sequences for building HMM with the programs provided with HMMER and HMMER2 packages (see Hughey and Krogh 1996, J. Mol. Biol. 235:1501-1531).
A6. Do a new database search comparing new HMM with the non-redundant protein database.
A7. Continue steps A3-A6 until the convergence of the Markov model i.e., until no new sequences are identified, or the maximum allowed number of iterations as defined by the user is reached. (Hugh R. and Krogh A., 1996, Comput. Appl. Biosci. 12: 95-107).

Figure 3A:
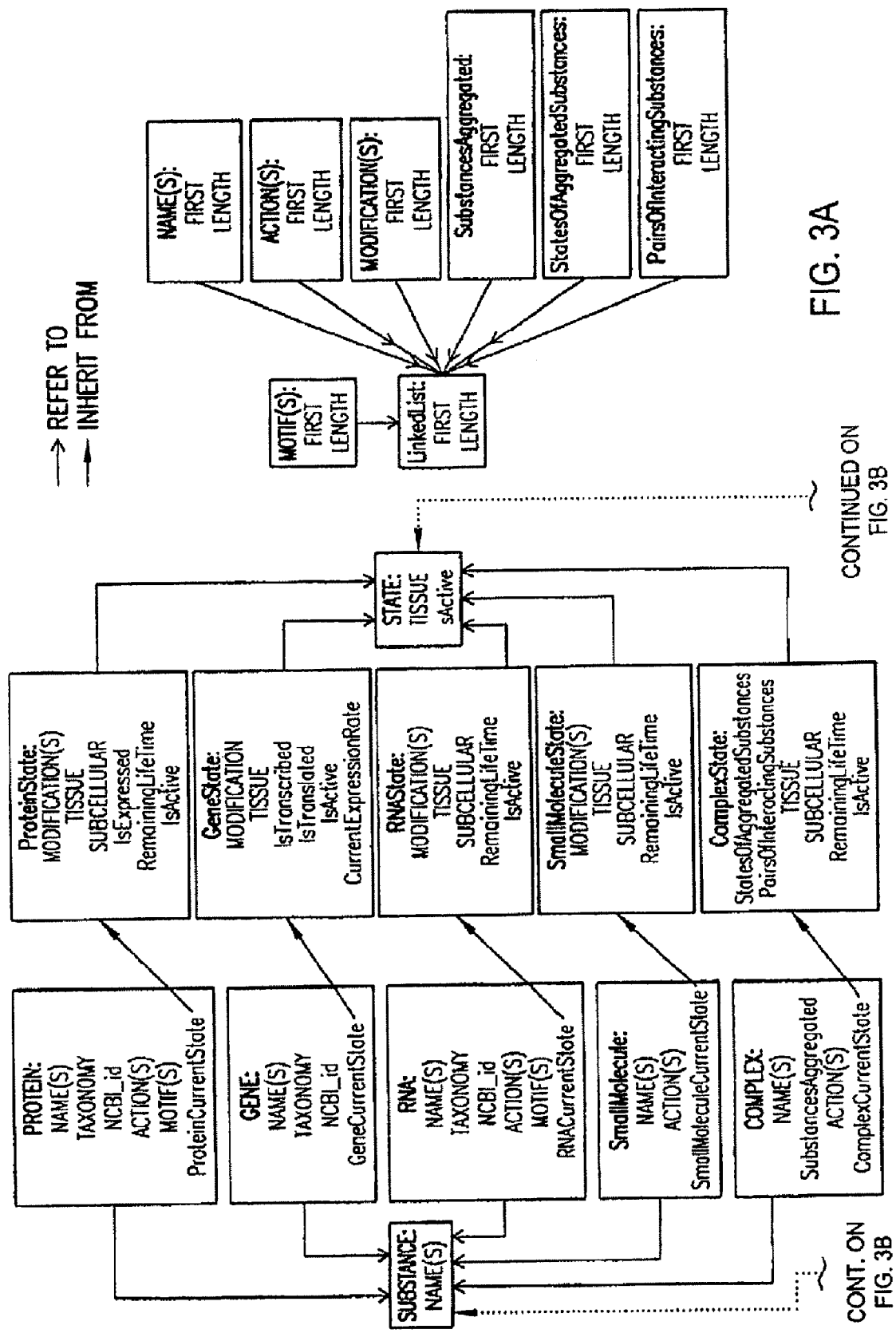
FIGS. 3A and 3B are diagrams illustrating the object representation of molecules and relations between them.
Figure 3B:
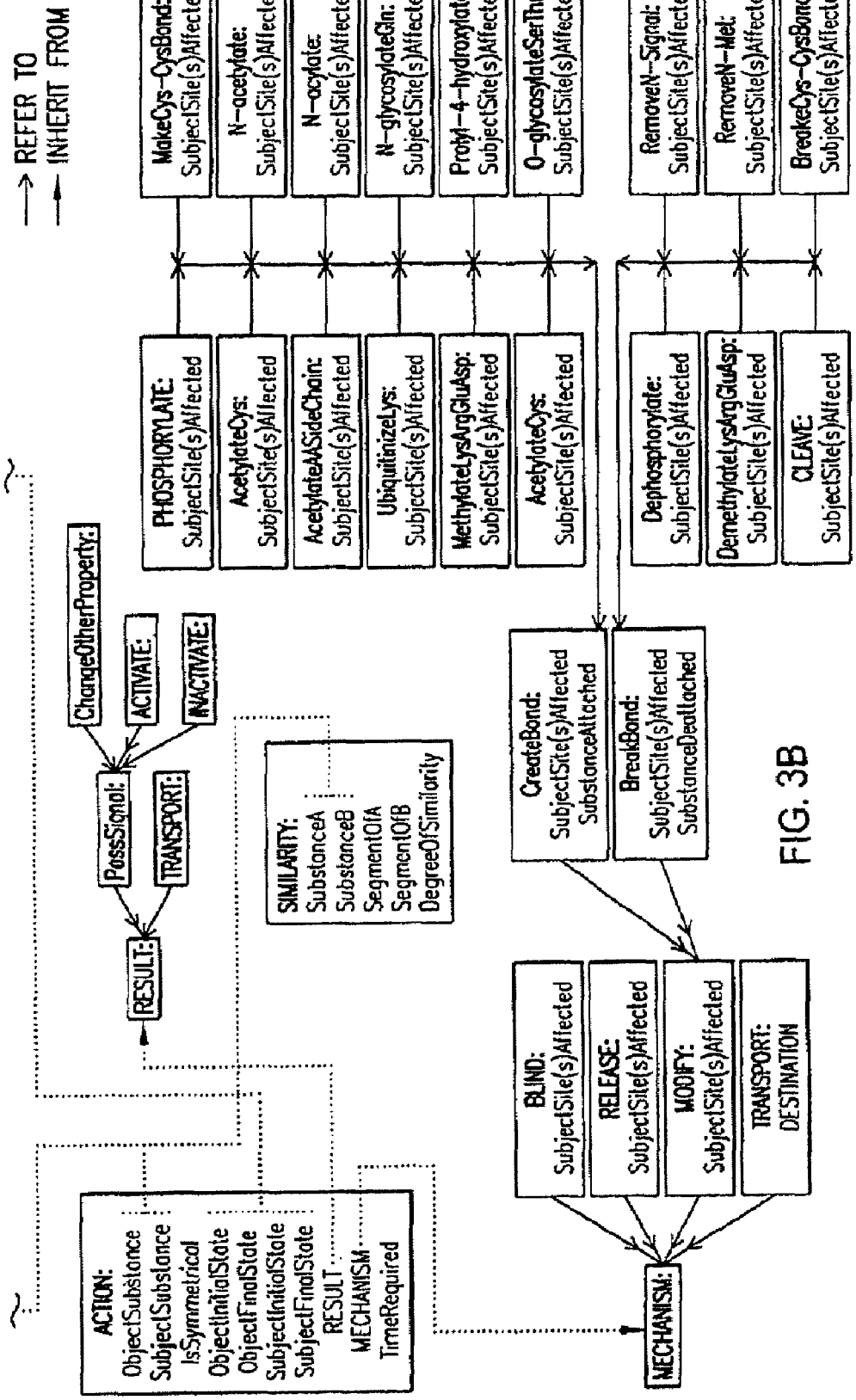

In addition, in yet another embodiment of the invention, a specialized database may be designed to contain a semantic model of proteins and of the possible interactions between them. Such databases are particularly useful for computation and analysis of regulatory networks between proteins. The semantic model is designed for representing substances, such as proteins and actions between them, and is based on widely accepted principles of object-oriented programming languages such as Java. FIGS. 3A and 3B are diagrams illustrating the object representation of molecules and relations between them. As indicated in FIGS. 3A and 3B there are six major classes, corresponding to the top-level classification of objects and actions: (i) a substance; (ii) a state of a substance; (iii) a similarity between substances; (iv) an action between substances; (v) a result of the action; and (vi) a mechanism that enables an action.

FIGS. 3A and 3B present the class design graphically, listing the variables that represent the properties of each class or class object in the implementation. Classes can be made nested via the mechanism of "inheritance", i.e., classes are defined starting with the most general ones and moving towards more specific classes. Definition of more specific classes is simplified because the properties of the general classes are "inherited" by the specific classes and need not be redefined each time (see, Flanagan 1997, Java in a Nutshell, Second Edition. O'Reilley & Associates, Inc. Sebastopol, Calif.).

As shown in FIGS. 3A and 3B, the two key object types in this scheme are substances (nodes of the graph representing regulatory networks) and actions (oriented edges connecting pairs of nodes), while result and mechanism objects are auxiliary to object action. Each substance object is characterized with a state. In this scheme, action is the most complicated object; each action object is characterized by a specific pair of substances participating in the action, one of which can be active and is referred to as Subject Substance and the second of which can serve as a substrate for the former and is referred to as Object Substance. Furthermore, for each action the initial and final states corresponding to interacting substances are defined. The property Time Required of each Action Object allows the setting of different durations for different actions (time is measured in relative units; see Rene Thomas and Richard D'Ari, 1990, "Biological Feedback," CRC Press Boca Raton, Ann Arbor, Boston).

Once developed, the specialized databases can be used to identify novel genes based on computation and analysis of phylogenetic trees for multigene families and analysis of homologous regulatory networks.

In a specific embodiment of the invention, a specialized database was generated using a set of keywords defining proteins involved in apoptosis (see, FIG. 4). The specialized sequence database was referred to as Apoptosis 3. As a first step in generating the specialized database, a comprehensive set of articles describing the system of apoptosis or programed cell death was compiled. The articles were analyzed and information on regulatory pathways characterizing apoptosis from a variety of different organisms was extracted. Such pathways included those involved in MHC-T cell receptor interactions, inflammatory cytokine signal transduction, induction by light, γ-radiation, hyperosmolarity or heat shock, pathways involving immunoregulatory receptors or receptors having cytoplasmic domains, integrin-related pathways and perforin/granzymeβ related pathways. The collected information was stored using Powerpoint (Microsoft) as a collection of graph/plots depicting the regulatory pathway. In addition, a list of proteins relevant to regulation of apoptosis was compiled.

Using the program Psi Retriever, sequences encoding the proteins relevant to regulation of apoptosis were retrieved from the non-redundant (NCBI) database of protein sequences and stored as a FASTA file. The FASTA file was then converted to a binary blast database using the program FORMATDB from the BLAST suit of programs. The BLAST suit of programs provides a set of programs for very fast comparisons of a single sequence to a large database. Both the database and the search or query sequence can be any combination of nucleotide and/or amino acid sequences.

In a working example described herein, the Apoptosis 3 database was used to compare genomic and cDNA sequences derived from the 13 q region of human chromosome 13. This region of the chromosome is associated with Chronic Lymphocytic Leukemia (CLL). Using this method of analysis a human gene with significant homology to the mouse Rpt1 gene was identified. When the activity of Rpt1 is knocked out in mice, the regulatory effect is manifested as a block in T-lymphocyte apoptosis. This result indicates that the identified human Rpt1 homology may represent the gene in which genetic defects lead to CLL.

The amino acid sequence of the human Rpt1 gene is presented in FIG. 15. The present invention relates to nucleic acid molecules encoding the human Rpt1 protein shown in FIG. 15. The invention also relates to nucleic acid molecules capable of hybridizing to a nucleic acid molecule encoding the human Rpt1 protein presented in FIG. 15 under conditions of high stringency. By way of example and not limitation, procedures using such conditions of high stringency are as follows: Prehybridization of filters containing DNA is carried out for 8 hours to overnight at 65° C. in buffer composed of 6×SSC, 50 mM Tris-HCl (pH7.5), 1mM EDTA, 0.02% PVP, 0.02% Ficoll, 0.02% BSA and 500 mg/ml denatured salmon sperm DNA. Filters are hybridized for 48 h at 65° C. in prehybridization mixture containing 100 mg/ml denatured salmon sperm DNA and 5-20×10$^6$ CpM of $^{32}$P-labeled probe. Washing of filters is done at 37° C. for 1 h in a solution containing 2×SSC, 0.01% PVP, 0.01% Ficoll and 0.01% BSA. This is followed by a wash in 0.1×SSC at 50° C. for 45 minutes before autoradiography. Other conditions of high stringency which may be used are well known in the art.

5.4. Gene Discovery Through Phylogenetic Analysis of Gene Families

The present invention provides a method for identifying novel genes comprising the following steps: (i) comparing a single sequence with a database; (ii) processing the output into a sequence alignment; (iii) computing gene trees; and (iv) analyzing the trees to predict the existence of undiscovered genes.

FIG. 5 shows a "species tree," a "gene tree" and a "reconciled tree". A "species tree", as defined herein, is a graph depicting the correct order of speciation events leading to a set of present day species as defined by taxonomy. A "gene tree" is a graphical representation of the evolution of a gene from a single ancestral sequence in a common progenitor to a set of present-day sequences in different species. Where gene duplication has occurred, a branch is bifurcated. The branch lengths of a gene tree are most frequently measured either in terms of the number of amino acid or nucleotide replacements per site or in terms of millions of years (absolute geological time). In the former case, the average replacement rate in the majority of the published trees varies among tree branches, and the root-to-tip distances are different for different present day sequences. In the latter case, all root-to-tip distances are equal and the height of each interior node of the tree corresponds to the absolute geological time passed since the gene duplication corresponding to the interior node took place.

If a gene is unique, i.e., represented with a single copy per genome rather than being a member of a family of similar genes, the correct gene tree depicting the origin of this gene in a few different species is identical to the species tree. In many instances, a single ancestral gene has been duplicated repeatedly during evolution to form a multigene family. A gene tree is constructed from a gene as it occurs in several species and reflects both speciation events and gene duplications within the same genome. Two homologous genes taken from different species that originated from the nearest common ancestor by speciation are referred to as orthologs, while any two genes that originated from the common ancestor via a series of events involving intragenomic duplications, or conversions, are called paralogs. The terms "ortholog" and "paralog" are applied to both nucleic acid and proteins herein.

If gene deletions are forbidden and all genes for all species represented in the tree are known, the gene tree can be reconfigured to recapitulate the species tree, such that each subtree contains only orthologous genes. This tree is referred to as a reconciled tree and is shown in FIG. 5. Imperfect gene trees which contain incorrect or partial species subtrees can be used to build reconciled trees that indicate events of speciation, gene loss, and gene duplication.

Orthologs from different species in gene trees are usually clustered together, so that if all the existing homologous genes from different species were known, the same relationship of species would be recapitulated in each cluster of orthologous genes. Since in reality a considerable number of genes are not yet identified, the real gene trees contain incomplete clusters of orthologs that can be used for identification of the missing genes.

By applying phylogenetic analysis, i.e., reconstruction of gene trees of gene/protein sequences, one can predict the existence of undiscovered genes in humans and other species in addition to identifying the function of a gene. Such a technique is a significantly more powerful tool for identification of new genes than mere sequence comparisons.

Methods of computing gene trees from a set of aligned sequences include the: (i) heuristic method based on an optimization principle which is not directly motivated by a probability model (Fitch, 1974 J. Mol. Evol. 3:263-268)), (ii) the maximum likelihood method (Goldman, 1990, Syst. Zool. 30:345-361; Yang et al., 1995, Syst. Biol. 44:384-399; Felsenstein, J., 1996, Methods Enzymol. 266-418-427); and (iii) the distance matrix tree making method (Saito, N. and Nei, M., 1987, Mol. Biol. Evol. 4:406-425). Since the data analyses of orthologs and paralogs often involve very distantly related sequences, the maximum likelihood method is preferably used for small data sets and the distance-matrix method in other instances.

To construct a reconciled tree according to the invention, the first step comprises a search for homologs in a publicly or privately available database such as, for example, GEN-BANK, Incyte, binary BLAST databases, SWISS-PROT and NCBI databases. Following the identification of homologous sequences a global alignment is performed using, for example, the CLUSTALW program. From the sequence alignment a gene tree is constructed using, for example, the computer program CLUSTLAW which utilizes the neighbor-joining method of Saito and Nei (1997, Mol. Biol. Evol. 4:406-425). Construction of a species tree is then retrieved from, for example, the following database 3.NCBI.NLM.NIH.GOV//taxomy.tax.html.

The species tree and gene tree are given as input into the algorithm described below, which integrates both trees into a reconciled tree. Agreement between the gene tree and the corresponding species tree for any given set of sequences indicates the identification of orthologs. In contrast, disagreement between the species and gene tree suggest a gene duplication that resulted in the formation of a paralog. Thus, through generation of a reconciled tree one can identify orthologs present in one species but missing in another. These can be deduced by forming subtrees of orthologs in a gene tree, and then comparing the subtree in the gene tree with a species tree. A missing gene appears as a branch present in the species tree but absent in the gene tree. The algorithm for defining an orthologous gene subtree and predicting the undiscovered, or lost in evolution, genes is as follows:

Let $T_g$ be the most likely gene tree identified with one of consistent tree-making methods from a set of properly aligned homologous genes $\{1, 2, \ldots, s\}$, such that one or more homologous genes from every species corresponds to pending vertices of $T_g$. Each gene is labeled with the species it comes from $(1, \ldots, s)$ adding subscripts to distinguish homologous genes from the same species whenever it is necessary. Let $T_s$ be the true species tree (tree correctly reflecting speciation events which we assume to be known) for species $\{1, 2, \ldots, s\}$. Due to the biological meaning of $T_s$ each species in this tree is represented only once. It is assumed that both $T_s$ and $T_g$ are binary, although it is straightforward to extend the algorithm described here to the case of multifurcated trees.

Algorithm

A1. For each pair of interior nodes from trees $T_g$ and $T_s$, compute similarity $\sigma(S_{gi}, S_{sj})$.
A2. Find the maximum $\sigma(S_{gi}, S_{sj})$
A3. Save $S_{gi}$ as a new subtree of orthologs, save $\{S_{gi}\}-\{S_{sj}\}$ as a set of species that are likely to have gene of this kind (or lost it in evolution).
A4. Eliminate $S_{gi}$ from $T_g$; $T_g := T_g \backslash S_{gi}$.
A5. Continue A2-A4 until $T_g$ is non-empty.

The following definitions apply:
Let $S_{gi}$ be an ith subtree of $T_g$ (corresponding to the ith interior node), correspondingly, let $S_{sj}$ be jth subtree of tree $T_s$.

Let $\{S_{gi}\}$ stand for an unordered set of species represented in $S_{gi}$ such that each species is represented exactly once, and let $|\{S_{gi}\}|$ and $\{|S_{gi}|\}$ be the number of entries in $\{S_{gi}\}$ and the number of pending vertices in $S_{gi}$, respectively. Define by $S_{sj}(S_{gi})$ the unique subtree of $S_{sj}$ that has leaves labeled exclusively with species from $|\{S_{gi}\}|$, so that each element of $|\{S_{gi}\}|$ is used i.e., that is, the unique subtree obtained by eliminating from $S_{sj}$ all species that are not present in $|\{S_{gi}\}|$. Then define similarity measure, $\sigma$, between $S_{gi}$ and $S_{sj}$ in the following way:

$$\sigma(S_{gi}, S_{sj}) = 0 \text{ if } |S_{gi}| \neq |\{S_{gi}\}|, \text{ or } S_{sj}(S_{gi}) \neq S_{gi}, \text{ and}$$

$$\sigma(S_{gi}, S_{gi}) = |S_{gi}|$$

The support of tree clusters by data can be measured using the bootstrap technique described in Felsenstein (1985, Evolution 39:783-791).

In an embodiment of the invention, the human antiquitin gene was identified using phylogenetic analysis. The aldehyde dehydrogenase gene family in humans can be subdivided into at least ten ancient subtrees characterized by different functions of corresponding proteins. These genes probably arose from a series of gene duplications of an ancestral gene which took place before the divergence of a common ancestor of Eukaryotes and Eubacteria.

The aldehyde dehydrogenase gene cluster is highlighted in FIGS. 6A and 6B which show the original tree of ALDH sequences, the circled area indicating a sequence cluster where bacterial (*Bacillus subtilis*), plant (*Brassica napus*), and nematode (*Caenorhabditis elegans*) ortholog is present, but a human ortholog is not known. A random screening of cDNA libraries showed that a human ortholog, referred to as antiquitin, does exist. FIGS. 7A and 7B show the same gene tree as in FIG. 6 with an additional human protein referred to as antiquitin present in the tree.

In yet another embodiment of the invention, a human ortholog of the murine Max-interacting transcriptional repressor Mad3 was identified through phylogenetic analysis of a gene family. The gene tree was constructed as follows. The protein sequences of known members of the Mad gene family were extracted from GENBANK database. The extracted sequences were aligned using multiple alignment program CLUSTALW running on Sun SPARC station. Redundant and non-homologous sequences as well as distant homologs from *S. cerevisiae, C. elegans, D. melanogaster* etc. were removed from the alignment. The refined set of sequences were realigned with CLUSTALW and a gene tree as presented in FIG. 18A was computed. To identify a human ortholog of the Mad3 protein, a human dbEST at NCBI was searched with program TBLASTN using mouse Mad3 protein sequences as a query. Two highly homologous ESTs were identified and are presented in FIG. 17A. To obtain a complete coding sequence a search was conducted to obtain overlapping sequences in dbEST. The search for overlapping sequences was performed using the program Iterate with EST Zs77e55.r1 (gb/AA278224) as the search query. The search identified a single overlapping sequence. The search for overlapping sequences was performed using program Iterate with EST zs77e55.r1 (gb/AA278224) serving as a query. The search returned a single overlapping sequence, namely HUMGS0012279 (dbj/C02407), thus showing that the two EST sequences found during the initial TBLASTIN search belong to the same gene. The complete sequence of the gene was assembled from the two ESTs using commercially available sequence assembly program SeqMan11 (DNASTAR Inc., WI). The nucleotide sequence of the human Mad3 gene is presented in FIG. 17B. The deduced amino acid sequence of which is presented in FIG. 17C. The complete DNA sequence is also shown.

The present invention relates to nucleic acid molecules encoding the human Mad3 protein shown in FIG. 17C. The invention also relates to nucleic acid molecules that hybridize to the nucleic acid molecule of FIG. 17B under conditions of high stringency and encode a Mad3 protein. By way of example and not limitation, procedures using such conditions of high stringency are as follows: Prehybridization of filters containing DNA is carried out for 8 hours to overnight at 65° C. in buffer composed of 6×SSC, 50 mM Tris-HCl (pH7.5), 1mM EDTA, 0.02% PVP, 0.02% Ficoll, 0.02% BSA and 500 mg/ml denatured salmon sperm DNA. Filters are hybridized for 48 hours at 65° C. in prehybridization mixture containing 100 mg/ml denatured salmon sperm DNA and 5-20×10$^6$ CpM of $^{32}$P-labeled probe. Washing of filters is done at 37° C. for 1 hour in a solution containing 2×SSC, 0.01% PVP, 0.01% Ficoll and 0.01% BSA. This is followed by a wash in 0.1× SSC at 50° C. for 45 minutes before autoradiography. Other conditions of high stringency which may be used are well known in the art.

5.5. Simulation and Hypothesis Testing

The simulation and hypothesis testing methods of the invention, described in the subsections below, utilize specialized databases of gene/protein structures and interactions for identifying potentially undiscovered members of multigene families through comparisons of regulatory networks for different species, searching expressed sequence tag (EST) databases, and simulation of regulatory cascades.

5.5.1. Gene Discovery Through Analysis of Regulatory Networks

The present invention provides a method for identifying undiscovered genes through comparisons of regulatory networks for different species where functionally similar regulatory systems are conserved. The amount of information available concerning regulatory genes and/or proteins in different organisms and their functional relationships allows one to reconstruct and compare regulatory networks. Since in most cases, the knowledge of all genes involved in almost any particular regulatory system is incomplete, a comparison of homologous networks within the same organism and between different species permits the identification of genes absent in a system under comparison.

The identified genes, being part of a regulatory network, are implicated as potentially contributing to a phenotype of a disease associated with the system under analysis. Using the methods of the present invention these putative disease genes can be cloned, mapped and analyzed for mutations directly, thereby omitting the expensive and time-consuming steps of positional cloning and sequencing of genomic regions. Gene discovery by analysis of regulatory networks is outlined in FIG. 8. The analysis is initiated starting with a biological system (e.g., signaling pathway of genes involved in Bc1-2-regulated apoptosis in lymphocytes), a single gene (e.g., Bc1-2) or a gene family (e.g., caspases).

Initially, a specialized database is generated for comparison of regulatory networks between different species. For example, starting with a single candidate gene in a single species, a typical iteration in this process begins with identification of all known proteins and genes that are upstream and downstream with respect to it in regulatory hierarchies and the reconstruction of a network of interacting genes and proteins. Next, for each protein, a set of key domains and motifs is identified and this information is used to search for related proteins in humans and other species. The identified sequences are compared and for each pair of sequences showing similarity above a certain threshold, a similarity object is generated. A similarity object is generated if two sequences, nucleotide or amino acid, show significant similarity in database searches (p value <0.001). The object retains the following information: (i) reference to similar substances i.e., genes or proteins; (ii) significance of the similarity, similarity score and percent of identity; and (iii) coordinates of the similarity region within two compared sequences. "Orthology objects" constitute a subset of "similarity objects" which satisfies one additional requirement, i.e., that two similar sequences should be identified as orthologs by the tree-based algorithm described above. In identifying orthologs, if gene A is orthologous to gene B, and gene B is orthologous to gene C, gene A is necessarily orthologous to gene C.

In a specific embodiment of the invention, for each species under analysis, orthologous proteins or genes are identified. In a further embodiment of the invention, small orthologous molecules participating in a regulatory network for two or more species may also be identified. Where proteins, genes, or molecules are orthologs, the action of the protein, gene or molecule between species may be interchangeable. If more than two species are involved in the analysis, subtrees of orthologous substances and subtrees of orthologous actions are identified.

Once orthologous genes, proteins or molecules are identified in two or more species, by forming a reconciled tree, for example, a set of orthologous or paralogous regulatory networks can be analyzed and visualized using graph theory where arcs represent actions and vertices represent substances. Thus, the method of the invention may further comprise the following steps: (i) superimposing the orthologous regulatory networks from two or more species and searching for the actions (arcs) and substances (vertices) in the homologous networks that are represented in some taxa but absent in others; (ii) superimposing paralogous regulatory networks from the same taxa and searching for paralogous genes that are missing in some taxa; and (iii) computing a general regulatory network that summarizes common regulatory sequence relationships known for more than one species.

In a specific embodiment of the invention a set of regulatory networks from different species, relating to the same biological system, apoptosis, for example, can be analyzed and visualized utilizing the following methods: (i) for each species functional information is collected relating to apoptosis; (ii) using the functional information, regulatory networks for each species comprised of interacting proteins and/or the genes involved in apoptosis are generated; (iii) the sequences of the interacting proteins and genes of each of the regulatory network are compared and for sequences showing similarity above a predetermined threshold range; and (iv) distinguishing between orthologs and paralogs using the methods set forth above.

An analysis similar to that performed using subtrees of sequences may be applied to classify protein functions as orthologous or paralogous actions. A "generalized" regulatory network maybe represented as a network wherein a substance as it occurs in a particular species is substituted with a cluster (i.e., subtree) of orthologous substances among species. In the final step of the analysis the clusters within each species are compared to one another, to identify missing genes.

FIG. 11 depicts the regulatory relationships among hypothetical proteins (denoted with Arabic numerals) of hypothetical species A and B. As indicated in FIG. 11A, an overlay of regulatory data for two species overlaps, but not completely. As indicated, protein 5 is known only for species B while protein 3 is known only for species A. The proteins in different species denoted with the same numeral are considered orthologous. As indicated, the regulatory relationships between a pair of proteins can be of three different kinds. FIG. 9B, 9C, and 9D represent Boolean operations, OR, AND, and XOR, as arcs of the two regulatory relationships depicted in FIG. 9A, the same operations being applicable to the set of vertices of the two regulatory relationships. In some instances, orthologous networks in two distantly related taxa may have the same domains but arrangement of the domains between the related taxa may be different. In such a case, a one-to-one correspondence between orthologous proteins in closely related species has to be substituted with a one-to-many relationship among domains comprised within the proteins. For this purpose, a similarity object may be defined operating on pairs of motifs/domains in two proteins, and substitute pairs of orthologous proteins with pairs of orthologous domains. After this correction, homologous networks are compared as described above.

FIG. 10 is a diagram representing a hypothetical example of defining homologous protein networks in two different species using protein motifs, the diagram showing only two hypothetical proteins (lane 2) for species A and three hypothetical proteins (lanes 1, 3, and 4) for species B. Protein 1 in both species has motifs α and β, protein 2 has motifs δ, ε, and ζ, and proteins 3 and 4 have motifs δ and ζ, and ε, respectively. The motif analysis indicates that proteins 3 and 4 in species B may collectively perform the same function as protein 2 in species A.

5.5.2 Gene Discovery Based on Protein Motif/Domain Searches

The present invention provides yet another method for identifying genes that are homologous and perform the same or an αvακλογovσ function in different species. The method of the invention comprises the following steps: (i) creating a database of sequences which comprise a motif or domain composition of a gene of interest using, for example, HMMER software; and (ii) searching additional databases for expressed sequence tags (ESTs) containing the domains and motifs characteristic for the gene of interest with HMMs of domains and motifs identified in step (i). In yet another embodiment of the invention, sequences may be searched which correspond to nucleotide sequences in an EST database or other cDNA databases using a program such as BLAST and retrieving the identified sequences. In an optional step, for each EST identified, sequence databases can be searched for overlapping sequences for the purpose of assembling longer overlapping stretches of DNA. Once identified, the ESTs can be used to isolate fall length nucleotide sequences comprising the gene of interest using methods such as those described in Section 5.4, infra.

The general flowchart scheme for gene discovery analysis based on motif/domain search is shown in FIG. 11. In a specific embodiment of the invention, the method referred to as the "phylogenetic reflection technique" comprises, first, defining the motif or domain composition of a gene of interest involved in a biological system of interest. Second, protein-coding genes from other species, including for example yeast and/or nematode genes, that bear a significant similarity to the gene of interest or a specified domain of the corresponding protein are collected. Third, the identified genes are in turn subjected to a "domain analysis" to establish protein motifs which might suggest a function of these genes using, for example, HMMER software. Fourth, the selected genes are in turn used for database searches in EST databases (dbEST) and/or a non-redundant (nr) database to identify unknown genes that are potentially orthologous to the selected yeast and nematode genes. Once identified ESTs having different tumor suppressor domains may be linked using multiple PCR primers. Using routine cloning techniques, well known to those of skill in the art, a full length cDNA representing the gene of interest can be obtained.

Once new genes are identified by domain/motif analysis experimental searches may be carried out to isolate complete coding sequences and evaluate their tissue- and disease-specific expression patterns. In parallel their position with respect to regulatory networks can be identified as described below.

In a specific embodiment of the invention, an apoptosis related human gene was identified using the method described above. As a first step C. elegans genes containing either POZ or Kelch domains were identified. A Hidden Markov Model was developed using POZ and Kelch sequences from the *Drosophila* Kelch protein and any identified homologs. The resulting Hidden Marker Model was used to search through the collection of C. elegans protein sequences. One of the identified C. elegans genes contained a POZ domain, death domain, kinase domain and heat repeat. The presence of both a death domain and a kinase domain suggested that the protein functions as a regulatory protein.

A human EST database was searched using the protein sequence of the identified C. elegans gene and two sequences were identified (FIG. 14A). A gene tree was computed to determine whether the identified human sequences were orthologs of the C. elegans gene. As depicted in FIG. 14B, the human EST AA481214 appears to be a true ortholog of the C. elegans gene. FIG. 14C presents the nucleotide sequence of the identified death domain gene. FIG. 14D presents the amino acid sequence of the death domain protein.

The present invention encompasses the nucleic acid molecule of FIG. 14C, comprising the sequence of EST AA481214 and proteins encoded by said nucleic acid molecule. The invention also relates to nucleic acid molecules capable of hybridizing to such a nucleic acid molecule under conditions of high stringency. By way of example and not limitation, procedures using such conditions of high stringency are as follows: Prehybridization of filters containing DNA is carried out for 8 hours to overnight at 65° C. in buffer composed of 6×SSC, 50 mM Tris-HCl (pH7.5), hmM EDTA, 0.02% PVP, 0.02% Ficoll, 0.02% BSA and 500 mg/ml denatured salmon sperm DNA. Filters are hybridized for 48 hours at 65° C. in prehybridization mixture containing 100 mg/ml denatured salmon sperm DNA and 5-20×10$^6$ CpM of $^{32}$P-labeled probe. Washing of filters is done at 37° C. for 1 hour in a solution containing 2×SSC, 0.01% PVP, 0.01% Ficoll and 0.01% BSA. This is followed by a wash in 0.1×SSC at 50° C. for 45 minutes before autoradiography. Other conditions of high stringency which may be used are well known in the art.

5.5.3. Simulation of Regulatory Cascades

In an embodiment of the invention, an interactive graphical program is utilized for visualizing the scheme of regulatory relationships, "current" states of the substances, and active and inactive actions between pairs of substances. Such a program can be utilized for identification of genes which are associated with a specific disease. Currently, disease associated genes are discovered through positional cloning methods which combine methods of genetics and physical mapping with mutational analysis. The present invention provides a novel method for discovering disease associated genes.

For simulating regulatory cascades, it is assumed that the time in a simulated regulatory system advances in discrete "quanta," or periods of time. The "state of substances" of the system for each discrete period of time is computed by: creating a set of substance objects, where a set of interactions between each created substance object is known, an initial state is specified. The time is initially set to zero. All defined actions are observed to confirm that the substances corresponding to the actions (i) exist, and (ii) are in the right initial states. Action is defined by a pair of substances that are in suitable states. The "subject" substance is in the inactive state, while the "object" substance can be in either active, or inactive, state depending on the action type. For example, the action "dephosphorylation" requires an active phosphatase ("subject" substance) and a phosphorylated substitute protein ("object" substance) in phosphorylated form. If both conditions are satisfied, the action is recorded as in progress. At termination, the substances must change their states as specified by the action. On each following "quantum" of time, the simulation proceeds in the same way while maintaining the "bookkeeping" of the remaining time for each action and the remaining lifespan of each substance. The simulation stops when there are no more active actions available. The program allows editing of the properties of the objects, changing the scale and focus of the visualized simulation, and experimenting with the systems output.

In a specific embodiment of the invention a "knock out" of a gene can be simulated to model the regulatory system that normally includes hypothetical gene A. One of the typical questions related to the gene knock out is how does the knock out affect a biological pathway of interest. A hypothetical example of evaluating the impact of a knock out of hypothetical gene A on the expression of a hypothetical gene B is shown in FIG. 12. The answer to such a question could be "gene B will be inhibited" or "gene B will be induced" or "no effect".

In the practice of the present invention, a simple algorithm involving multiplication of gene interaction "signs" along the shortest pathway between the genes can be used to determine the outcome. The algorithm involves the following steps: (i) identification of the shortest non-oriented pathway connecting genes A and B involved in a pathway of interest; (ii) assigning sign "–" to gene A since it is knocked out and taking this sign as the initial sign value; (iii) moving along the shortest pathway between genes A and B, multiplying the current value of the sign with the sign of the next arc, where "–" stands for inhibition, "+" stands for induction or activation, and "0" stands for the lack of interaction between two proteins in the specified direction; (iv) determining if the final result of multiplication is "0", if so eliminating the zero arc and trying to find the shortest oriented bypass pathway between A and B in the remaining network; otherwise stop. The final value of the sign at the moment of arriving at vertex B would indicate the most likely effect of the knock out of gene A which can be any one of the following: inhibition of gene B, induction/activation of gene B, or none. In addition to the "electronic knock out", an "electronic knock in" of a particular gene can be simulated. In such a computer simulation, the artificial addition of a gene and its effect on a regulatory system may be analyzed.

5.6. Identification and Isolation of Novel Genes

The present invention relates to identification of novel genes, i.e., missing orthologs or paralogs, and the isolation of nucleic acid molecules encoding novel genes. In a specific embodiment, a nucleic acid molecule encoding a missing ortholog or paralog can be isolated using procedures well known to those skilled in the art (See, for example, Sambrook et al., 1989, Molecular Cloning, A Laboratory Manual, 2d Ed., Cold Spring Harbor Laboratory Press, Cold Spring Harbor, N.Y. Glover, D. M. (ed.), 1985, DNA Cloning: A Practical Approach MRL Press, Ltd., Oxford, U.K. Vol. I, II.).

For example, genomic and/or cDNA libraries may be screened with labeled DNA fragments derived from a known ortholog or paralog from a specific species and hybridized to the genomic or cDNA libraries generated from a different species. For cross species hybridization, low stringency conditions are preferred. For same species hybridization, moderately stringent conditions are preferred. Any eukaryotic cell potentially can serve as the nucleic acid source for the molecular cloning of the gene of interest. The DNA may be obtained by standard procedures known in the art from cloned DNA (e.g., a DNA "library"), by cDNA cloning, or by the cloning of genomic DNA, or fragments thereof, purified from the desired cell.

By way of example and not limitation, procedures using conditions of low stringency are as follows (see also Shilo and Weinberg, 1981, Proc. Natl. Acad. Sci. USA 78:6789-6792; and Sambrook et al. 1989, Molecular Cloning, A Laboratory Manual, 2d Ed., Cold Spring Harbor Laboratory Press, Cold Spring Harbor, N.Y.): Filters containing DNA are pretreated for 6 h at 40 EC in a solution containing 35% formamide, 5×SSC, 50 mM Tris-HCl (pH 7.5), 5 mM EDTA, 0.1% PVP, 0.1% Ficoll, 1% BSA, and 500 mg/ml denatured salmon sperm DNA. Hybridizations are carried out in the same solution with the following modifications: 0.02% PVP, 0.02% Ficoll, 0.2% BSA, 100 mg/ml salmon sperm DNA, 10% (wt/vol) dextran sulfate, and 5-20×10$^6$ cpm $^{32}$P-labeled probe is used. Filters are incubated in hybridization mixture for 18-20 h at 40 EC, and then washed for 1.5 h at 55 EC in a solution containing 2×SSC, 25 mM Tris-HCl (pH 7.4), 5 mM EDTA, and 0.1% SDS. The wash solution is replaced with fresh solution and incubated an additional 1.5 h at 60 EC. Filters are blotted dry and exposed for autoradiography. If necessary, filters are washed for a third time at 65-68 EC and reexposed to film. Other conditions of low stringency which may be used are well known in the art (e.g., as employed for cross species hybridizations).

In another specific embodiment, a nucleic acid which is hybridizable to a nucleic acid under conditions of moderate stringency is provided. For example, but not by way of limitation, procedures using such conditions of moderate stringency are as follows: filters containing DNA are pretreated for 6 h at 55 EC in a solution containing 6×SSC, 5×Denhart's solution, 0.5% SDS and 100 mg/ml denatured salmon sperm DNA. Hybridizations are carried out in the same solution and 5-20×10$^6$ CpM $^{32}$P-labeled probe is used. Filters are incubated in the hybridization mixture for 18-20 h at 55 EC, and then washed twice for 30 minutes at 60 EC in a solution containing 1×SSC and 0.1% SDS. Filters are blotted dry and exposed for autoradiography. Other conditions of moderate stringency which may be used are well-known in the art. Washing of filters is done at 37 EC for 1 h in a solution containing 2×SSC, 0.1% SDS.

For expression cloning (a technique commonly used in the art), an expression library is constructed. For example, mRNA is isolated from the cell type of interest, cDNA is made and ligated into an expression vector (e.g., a bacteriophage derivative) such that it is capable of being expressed by a host cell (e.g., a bacterium) into which it is then introduced. Various screening assays can then be used to select for the expressed gene product of interest based on the physical, chemical, or immunological properties of its expressed product. Such properties can be deduced from the properties of the corresponding orthologs from other species.

In another embodiment, polymerase chain reaction (PCR) can be used to amplify the desired sequence from a genomic or cDNA library. To isolate orthologous or paralogous genes from other species, one synthesizes several different degenerate primers, for use in PCR reactions. In a preferred aspect, the oligonucleotide primers represent at least part of the gene comprising known ortholog or paralog sequences of different species. It is also possible to vary the stringency of hybridization conditions used in priming the PCR reactions, to allow for greater or lesser degrees of nucleotide sequence similarity between the known nucleotide sequences and the nucleic acid homolog being isolated.

Synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and a thermostable polymerase, e.g., Amplitaq (Perkin-Elmer). The nucleic acids being amplified can include mRNA or cDNA or genomic DNA from any eukaryotic species. After successful amplification of a segment of a the gene of interest, that segment may be molecularly cloned and sequenced, and utilized as a probe to isolate a complete cDNA or genomic clone.

Once identified and isolated the gene of interest can then be inserted into an appropriate cloning vector for amplification and/or expression in a host. A large number of vector-host systems known in the art may be used. Possible vectors include, but are not limited to, plasmids and modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini.

6. EXAMPLE

Use of Specialized Databases for Identification of Novel Genes

To test the method of using databases for gene discovery, protein sequence and domain/motif databases specific to two overlapping functional groupings of proteins: (i) proteins known to be tumor suppressors, and (ii) proteins implicated in apoptosis in animals were developed.

6.1 Apoptosis Gene Discovery Method

Identification of a putative apoptosis-related human gene began with an identification of all genes in *C. elegans* that contained either a POZ or kelch domain. A subset of these genes is shown in FIGS. 13A-13C. Hidden Markov Models (HMM) for the POZ and Kelch domains were built as follows. Starting with POZ and kelch sequences from the *Drosophilia* kelch protein (gi|577275) homologs were identified in other protein sequences using the BLASTP program. The resulting sequences showing significant similarity (e-value less than 0.001) were aligned using CLUSTALW program and the alignments were used to build Hidden Markov Models with HMMER-2 package (Krogh et al., 1995). A computer printout listing of HMM models of tumor suppressors appears as Appendix H to the present specification.

The resulting models were used to search through a database collection of *C. elegans* protein sequences. The domain structures of proteins having either a POZ or keich domain were identified using existing collections of protein domains. One of the unannotated protein-coding genes of *C. elegans* (corresponding protein accession number gi|1132541, see FIGS. 11A-11B) appeared to include a POZ domain, death domain, kinase domain, and heat repeat. A death domain is characteristic for the apoptosis system and a kinase domain indicates that the protein is likely to participate in phosphorylation of other proteins. The presence of these particular domains suggests that this protein is serving as a regulatory protein.

Using the protein sequence of gi|1132541, the database of human EST sequences was searched and a number of partial human cDNA sequences representing potential human orthologs or paralogs of the *C elegans* gi|1132541 were identified. The two closest human sequences, AA481214 and W51957, are depicted in FIG. 14A. To determine whether the identified human sequences were orthologs or paralogs to the gi|1132541 gene of *C. elegans*, a gene tree (Saito and Nei, 1997, Molecular Biol. Evol. 4:406-425) was computed. The gene tree was generated using homologous genes identified with a BLASTP search against NCBI non-redundant database, using the human EST AA481214 sequence as a query. The resulting tree indicates that the identified human EST AA481214 represents a true ortholog of the *C. elegans* gene gi|1132541 (FIG. 14B). The nucleotide sequence of the death domain protein is shown in FIG. 14C, as well as the deduced amino acid sequence presented in FIG. 14D.

6.1.2 Apoptosis Gene Discovery Method

As a first step in identifying a novel gene involved in apoptosis, a comprehensive set of articles describing the system of apoptosis/programmed cell death in different species was compiled using the keyword "apoptosis". By analyzing the articles, information on regulatory pathways characterizing this system in different species, i.e., *C. elegans*, mouse, fruit fly, chicken, and human, was extracted. The regulatory information was stored as a collection of schemes produced in PowerPoint (Microsoft). FIG. 4 shows a set of keywords defining proteins involved in apoptosis pathways. The keywords were used to generate a specialized sequence database, referred to as Apoptosis3, utilizing the PsiRetriever program for extraction of proteins from the all-inclusive non-redundant GENBANK database (NCBI). Using program PsiRetriever, sequences from the non-redundant (NCBI) database of protein sequences, were retrieved and stored as a FASTA file. The FASTA file was then converted into binary blast database using program FORMATDB from the BLAST suit of programs.

Genomic and cDNA sequences located in the region of human chromosome 13q were compared with the Apoptosis3 database using BLASTALL program from BLAST program complex. This region of the human genome is associated with Chronic Lymphocytic Leukemia (CLL). The comparison revealed significant similarity between a CLL region open reading frame and the mouse RPT1 protein (sp|P15533|RPT1) (FIGS. 13A-C). Analysis of regulatory functions of RPT1 in the mouse reveals that this gene functions as a repressor of the interleukin 2 receptor (IL-2R) gene. When the RPT1 gene is knocked out, the regulatory effect is manifested as a block of the apoptotic pathway in T lymphocytes resulting in an accumulation of T lymphocytes in blood. This result is consistent with aberrations observed in CLL, namely abnormal accumulation of B-cells in the blood (Trentin L. et al., 1997, Leuk. Lymphoma 27:35-42) and mutations in the human RPT1 gene play a role in development of CLL.

6.1.3. Example

A Discovery of a Human Ortholog of the Murine Max-Interacting Transcriptional Repressor The family of Myc proto-oncogenes encodes a set of transcription factors implicated in regulation of cell proliferation, differentiation, transformation and apoptosis. C-Myc null mutations result in retarded growth and development of mouse embryos and are lethal by 9-10 day of gestation. In contrast, overexpression of Myc genes inhibits cell differentiation and leads to neoplastic transformation. Moreover, deregulation of Myc expression by retroviral transduction, chromosomal translocation or gene amplification is linked to a broad range of naturally occurring tumors in humans and other species.

Another protein, called Max, is an obligatory heterodimeric partner for Myc proteins in mediating their function as activators of transcription during cell cycle progression, neoplastic transformation and programmed cell death (apoptosis). In order to make an active transcription factor the Myc proteins must form heterodimers with Max protein. This interaction with Max protein is necessary for specific binding of Myc with CACGTG box (or related E-boxes) on DNA and for activation of promoters located proximal to the binding sites.

Besides the Myc family of transcription factors, the Max protein forms complexes with another family of so-called MAD proteins: Mxi1, MAD1, MAD3 and MAD4. Whereas Myc:Max complexes activate transcription, MAD:Max complexes work in an opposite way repressing the transcription through the same E-box binding sites and apparently antagonize Myc-mediated activation of the same set of target genes.

During tissue development a shift from Myc:Max to MAD:Max complexes occurs coincidentally with the switch from cell proliferation to differentiation. The switch in heterocomplexes is thought to reflect a switch from activation to repression of common genes leading to cessation of proliferation, exiting the cell cycle and the beginning of cell differentiation. In differentiating neurons, primary keratinocytes, myeloid cell lines and probably other tissues the expression of different MAD:Max complexes appear in sequential order during the transition from cell proliferation to differentiation. The MAD3 expression appears first and it is restricted to proliferating cells prior to differentiation where it is co-expressed with two different member of Myc family, c-Myc or N-Myc. Mxi1 transcripts are detected in proliferating and differentiating cells whereas MAD1 and MAD4 were confined to post-mitotic cells. Because Myc expression is not always down-regulated in post-mitotic cells, co-expression of Myc and MAD genes may result in competition for Max heterodimers thus providing promoting or inhibitory effect on cell proliferation.

The gene expression patterns, along with ability of Mad proteins to suppress Myc-dependent transformation, are consistent with a potential function of Mad genes as tumor suppressors. This view is supported by the fact that allelic loss and mutations were detected at the Mxi1 locus in prostate cancers (Eagle et al., 1995 Nat Genet 9:249-55). Cloning of the murine proteins Mad3 and Mad4 as well as their relation to Max signaling network was described by Hurlin (Hurlin P J, et al., 1995, EMBO J. 14:5646-59) and Queva (Queva et al. 1998 Oncogene 16:967-977). Human orthologs of Mad4, Mad1 and Mxi1 are known.

In this example, the discovery of an unknown human ortholog of Mad3 protein found "in silico," by means of phylogenetic analysis of known mouse and human members of the Mad gene family and database searches is described. Since the function of murine Mad3 as a Max-interacting transcriptional repressor of Myc-induced neoplastic transformation is well described, we can assign the same function to its human ortholog. The gene tree shown in the FIG. 20 was constructed in the following way. The protein sequences of known members of Mad gene family were extracted from GENBANK database using NCBI Entrez keyword searches. The extracted sequences were aligned using multiple alignment program CLUSTALW running on Sun SPARC station. The quality of the multiple alignment was checked using program HitViewer Iterate (A. Rzhetsky, available upon request) and the redundant, non-homologous sequences as well as distant homologs from S. cerevisiae, C. elegans, D. melanogaster etc. were removed from the alignment. The refined set of sequences was realigned with CLUSTALW and a gene tree as presented in FIG. 15A was computed from the alignment.

The tree presented in FIG. 19A clearly shows the relationships between three known mouse genes and their two human homologs. Attempts to find a missing human ortholog of the mouse Mad3 gene in protein non-redundant database at NCBI using BLAST search did not identify any human homologs other than sequences that were already present on the tree, confirming the absence of a known human ortholog for Mad3 protein in the database.

In order to identify a human ortholog of the Mad3 protein, a human dbEST at NCBI was searched with program TBLASTN using Mad3 protein sequence as a query. Two EST were identified and are shown in FIG. 17A.

Due to the nature of dbEST database this search produced only partial sequences of potential candidate genes. To obtain complete coding sequences (complete cds) of the genes, a search was conducted to obtain overlapping sequences in dbEST. The search for overlapping sequences was performed using the program Iterate with EST zs77e55.r1 (gb|AA278224) serving as a query. The search returned a single overlapping sequence, namely HUMGS0012279 (dbj|C02407), thus indicating that the two EST sequences found during the initial TBLASTN search belong to the same gene.

The complete sequence of the gene was assembled from the two ESTs using commercially available sequence assembly program SeqManII (DNASTAR Inc., WI). The nucleotide sequence of the human Mad3 gene is presented in FIG. 17B. The deduced amino acid sequence of the gene is presented in FIG. 17C. The translated sequence consists of 206 amino acid residues 81% of which are identical to mouse Mad3 protein. The alignment of human and mouse Mad3 proteins shown below was made using BLAST server at NCBI and is presented in FIG. 17C.

Multiple alignment of the new sequence with sequences of known Mad proteins was made using CLUSTALW and viewed with the HitViewer. A gene tree was computed from this alignment using NJBOOT. Multiple alignment of the new sequence with sequences of known Mad proteins (FIG. 17C) along with its position on gene tree (FIG. 18B) shows that this new human gene found by the approach described above belongs to the family of Mad proteins and is the ortholog of mouse Mad3.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various publications are cited herein, the contents of which are hereby incorporated by reference in their entireties.

We claim:

1. A system for extracting information on biological entities from natural-language text data, comprising:
   (i) a computer processing apparatus configured to parse the natural-language text data;
   (ii) a computer processing apparatus configured to regularize the parsed text data to form structured word terms; and
   (iii) a computer processing apparatus configured to extract interactions between the biological entities from the natural-language text data, wherein the biological entities include genes and/or proteins.

2. The system according to claim 1, further comprising a computer processing apparatus configured to preprocess the data prior to parsing comprising identifying biological entities.

3. The system according to claim 1, further comprising a computer processing apparatus configured to referring to an additional parameter which is indicative of the degree to which subphrase parsing is to be carried out.

4. The system according to claim 1, wherein said parsing further comprises segmenting the text data by sentences.

5. The system according to claim 1, wherein said parsing further comprises:
   segmenting the text data by sentences;
   and segmenting each of the sentences at identified words or phrases.

6. The system according to claim 1, wherein said parsing further comprises:
   segmenting the text data by sentences; and
   segmenting each of the sentences at a prefix.

7. The system according to claim 1, wherein said parsing further comprises skipping undefined words.

8. The system according to claim 1, wherein said parsing further comprises:

identifying one or more binary actions and their relationships; and identifying one or more arguments associated with the actions.

9. The system according to claim 1, further comprising a computer processing apparatus configured to perform error recovery when parsing of the text data is unsuccessful.

10. The system according to claim 1, wherein said error recovery comprises:

segmenting the text data; and analyzing the segmented text data to achieve at least a partial parsing of the unsuccessfully parsed text data.

11. The system according to claim 1, wherein said tagging comprises for providing the structured data component in a Standard Generalized Markup Language (SGML) compatible format.

* * * * *

UNITED STATES PATENT AND TRADEMARK OFFICE
CERTIFICATE OF CORRECTION

PATENT NO. : 7,974,788 B2
APPLICATION NO. : 12/492992
DATED : July 5, 2011
INVENTOR(S) : Andrey Rzhetsky et al.

Page 1 of 1

It is certified that error appears in the above-identified patent and that said Letters Patent is hereby corrected as shown below:

In the Specifications:

On page 1, Column 1, lines 9-14:
STATEMENT REGARDING FEDERALLY FUNDED RESEARCH
This invention was made with government support under grant numbers LM06274 and LM05627 awarded by the National Library of Medicine. The government has certain rights in the invention.

should read

--STATEMENT REGARDING FEDERALLY SPONSORED RESEARCH OR DEVELOPMENT
This invention was made with government support under grant numbers LM06274 and LM05627 awarded by the National Institutes of Health. The government has certain rights in the invention.--

Signed and Sealed this
Fourteenth Day of May, 2013

Teresa Stanek Rea
*Acting Director of the United States Patent and Trademark Office*

SEQUENCE LISTING

<160> NUMBER OF SEQ ID NOS: 22

<210> SEQ ID NO 1
<211> LENGTH: 39
<212> TYPE: DNA
<213> ORGANISM: Artificial Sequence
<220> FEATURE:
<223> OTHER INFORMATION: Synthetic Nucleotide

<400> SEQUENCE: 1
agcaactaaa cacccatcca agcaaacaca cacacaaac         39

<210> SEQ ID NO 2
<211> LENGTH: 40
<212> TYPE: DNA
<213> ORGANISM: Artificial Sequence
<220> FEATURE:
<223> OTHER INFORMATION: Synthetic Nucleotide

<400> SEQUENCE: 2
aagcaactaa acacccatcc aagcaaacac acacacaaac        40

<210> SEQ ID NO 3
<211> LENGTH: 292
<212> TYPE: DNA
<213> ORGANISM: Artificial Sequence
<220> FEATURE:
<223> OTHER INFORMATION: Synthetic Nucleotide

<400> SEQUENCE: 3
aagtacagat ccacggaagg aacgatccaa acaaagacgc aacgacagaa ataacgatcc        60
acataactat ccaaatacat acgcacggaa gtacacacgt aattaaacac ggaagtacat       120
acagatccat ccacggatcc aaataacgaa ttaattacgc atccaaacaa atacggaagt       180
actcaaacac ggaacgaacc atccacggaa ggacctatac gtaagcaa ggatccacgg         240 aaggaacgaa gtacctatcc aaacacagac ggaagtaagc aacgacagat cc               292

<210> SEQ ID NO 4
<211> LENGTH: 10
<212> TYPE: DNA
<213> ORGANISM: Artificial Sequence
<220> FEATURE:
<223> OTHER INFORMATION: Synthetic Nucleotide

<400> SEQUENCE: 4
atctgtcacg         10

<210> SEQ ID NO 5
<211> LENGTH: 405
<212> TYPE: DNA
<213> ORGANISM: Homo sapiens

<400> SEQUENCE: 5
catggcttcc tggacaccaa ccctgccatc cgggagcaga cggtcaagtc catgctgctc        60
ctggccccaa agctgaacga ggccaacctc aatgtggagc tgatgaagca ctttgcacgg       120
ctacaggcca aggatgaaca gggcccatc cgctgcaaca ccacagtctg cctgggcaaa        180
atcggctcct acctcagtgc tagcaccaga cacagggtcc ttacctctgc cttcagccga       240
gccactaggg accgtttgc accgtcccgg gttgcgggtg tcctgggctt tgctgccacc        300
cacaacctct actcaatgaa cgactgtgcc cagaagatcc tgcctgtgct ctgcggtctc       360

```
actgtagatc ctgagaaatc cgtgcgagac caggccttca aggca            405
```

<210> SEQ ID NO 6
<211> LENGTH: 453
<212> TYPE: DNA
<213> ORGANISM: Homo sapiens
<220> FEATURE:
<221> NAME/KEY: variation
<222> LOCATION: (146)...(146)
<223> OTHER INFORMATION: n = A, C, G, or T

<400> SEQUENCE: 6

```
ccttcgagtt cggcaatgct ggggccgttg tcctcacgcc cctcttcaag gtgggcaagt    60
tcctgagcgc tgaggagtat cagcagaaga tcatccctgt ggtggtcaag atgttctcat   120
ccactgaccg ggccatgcgc atccgnctcc tgcagcagat ggagcagttc atccagtacc   180
ttgacgagcc aacagtcaac acccagatct cccccacgt cgtacatggc ttcctggaca   240
ccaaccctgc catccgggag cagacggtca agtccatgct gctcctggcc ccaaagctga   300
acgaggccaa cctcaatgtg gagctgatga agcactttgc acggctacag gccaaggatg   360
aacagggccc catccgctgc aacaccacag tctgcctggg caaaatcggc tcctacctca   420
gtgctagcac cagacacagg gtccttacct ctg                              453
```

<210> SEQ ID NO 7
<211> LENGTH: 1727
<212> TYPE: DNA
<213> ORGANISM: Homo sapiens

<400> SEQUENCE: 7

```
cagccgaagc amgcaaaaat tcttccagga gctgagcaag agcctggacg cattccctga    60
ggayttctgt cggcacaagg tgctgcccca gctgctgacc gccttcgagt tcggcaatgc   120
tgggccgtt gtcctcacgc ccctcttcaa ggtgggcaag ttcctgagcg ctgaggagta   180
tcagcagaag atcatccctg tggtggtcaa gatgttctca ccactgacc gggccatgcg   240
catccgcctc ctgcagcaga tggagcagtt catccagtac cttgacgagc caacagtcaa   300
cacccagatc ttccccacg tcgtacatgg cttcctggac accaaccctg ccatccggga   360
gcagacggtc aagtccatgc tgctcctggc cccaaagctg aacgaggcca acctcaatgt   420
ggagctgatg aagcactttg cacggctaca ggccaaggat gaacagggcc catccgctg   480
caacaccaca gtctgcctgg gcaaaatcgg ctcctacctc agtgctagca ccagacacag   540
ggtccttacc tctgccttca gccgagccac tagggacccg tttgcaccgt cccgggttgc   600
gggtgtcctg ggctttgctg ccacccacaa cctctactca atgaacgact gtgcccagaa   660
gatcctgcct gtgctctgcg gtctcactgt agatcctgag aaatccgtgc gagaccaggc   720
cttcaaggcm wttcggagct tcctgtccaa attggagtct gtgtcggagg acccgaccca   780
gctggaggaa gtggagaagg atgtccatgc agcctccagc cctggcatgg aggagccgc   840
agctagctgg gcaggctggg cgtgaccggg gtctcctcac tcacctccaa gctgatccgt   900
tcgcacccaa ccactgcccc aacagaaacc aacattcccc aaagaccac gcctgaagga   960
gttcctgccc cagccccac ccctgttcct gccaccccta caacctcagg ccactgggag  1020
acgcaggagg aggacaagga cacagcagag gacagcagca ctgctgacag atgggacgac  1080
gaagactggg gcagcctgga gcaggaggcc gagtctgtgc tggcccagca ggacgactgg  1140
agcaccgggg gccaagtgag ccgtgctagt caggtcagca actccgacca caaatcctcc  1200
aaatccccag agtccgactg gagcagctgg gaarctgagg gctcctggga acagggctgg  1260
```

-continued

```
caggagccaa gctcccagga gccacctyct gacggtacac ggctggccag cgagtataac    1320
tggggtggcc cagagtccag cgacaagggc gaccccttcg ctaccctgtc tgcacgtccc    1380
agcacccagc cgaggccaga ctcttggggt gaggacaact gggagggcct cgagactgac    1440
agtcgacagg tcaaggctga gctggcccgg aagaagcgcg aggagcggcg gcgggagatg    1500
gaggccaaac gcgccgagag gaaggtgcca agggcccat gaagctggga gcccggaagc     1560
tggactgaac cgtggcggtg gcccttcccg gctgcggaga gcccgcccca cagatgtatt    1620
tattgtacaa accatgtgag cccggccgcc cagccaggcc atctcacgtg tacataatca    1680
gagccacaat aaattctatt tcacaaaaaa aaaaaaaaaa aaaaaaa                  1727
```

<210> SEQ ID NO 8
<211> LENGTH: 287
<212> TYPE: PRT
<213> ORGANISM: Homo sapiens
<220> FEATURE:
<221> NAME/KEY: VARIANT
<222> LOCATION: (4)...(4)
<223> OTHER INFORMATION: Xaa = Any amino acid
<220> FEATURE:
<221> NAME/KEY: VARIANT
<222> LOCATION: (244)...(244)
<223> OTHER INFORMATION: Xaa = Any amino acid

<400> SEQUENCE: 8

```
Ser Arg Ser Xaa Gln Lys Phe Phe Gln Glu Leu Ser Lys Ser Leu Asp
  1               5                  10                  15

Ala Phe Pro Glu Asp Phe Cys Arg His Lys Val Leu Pro Gln Leu Leu
             20                  25                  30

Thr Ala Phe Glu Phe Gly Asn Ala Gly Ala Val Val Leu Thr Pro Leu
         35                  40                  45

Phe Lys Val Gly Lys Phe Leu Ser Ala Glu Glu Tyr Gln Gln Lys Ile
 50                  55                  60

Ile Pro Val Val Val Lys Met Phe Ser Ser Thr Asp Arg Ala Met Arg
 65                  70                  75                  80

Ile Arg Leu Leu Gln Gln Met Glu Gln Phe Ile Gln Tyr Leu Asp Glu
                 85                  90                  95

Pro Thr Val Asn Thr Gln Ile Phe Pro His Val Val His Gly Phe Leu
            100                 105                 110

Asp Thr Asn Pro Ala Ile Arg Glu Gln Thr Val Lys Ser Met Leu Leu
        115                 120                 125

Leu Ala Pro Lys Leu Asn Glu Ala Asn Leu Asn Val Glu Leu Met Lys
130                 135                 140

His Phe Ala Arg Leu Gln Ala Lys Asp Glu Gln Gly Pro Ile Arg Cys
145                 150                 155                 160

Asn Thr Thr Val Cys Leu Gly Lys Ile Gly Ser Tyr Leu Ser Ala Ser
                165                 170                 175

Thr Arg His Arg Val Leu Thr Ser Ala Phe Ser Arg Ala Thr Arg Asp
            180                 185                 190

Pro Phe Ala Pro Ser Arg Val Ala Gly Val Leu Gly Phe Ala Ala Thr
        195                 200                 205

His Asn Leu Tyr Ser Met Asn Asp Cys Ala Gln Lys Ile Leu Pro Val
    210                 215                 220

Leu Cys Gly Leu Thr Val Asp Pro Glu Lys Ser Val Arg Asp Gln Ala
225                 230                 235                 240

Phe Lys Ala Xaa Arg Ser Phe Leu Ser Lys Leu Glu Val Ser Glu
                245                 250                 255
```

```
Asp Pro Thr Gln Leu Glu Glu Val Glu Lys Asp Val His Ala Ala Ser
            260                 265                 270
Ser Pro Gly Met Gly Gly Ala Ala Ser Trp Ala Gly Trp Ala
            275                 280                 285
```

<210> SEQ ID NO 9
<211> LENGTH: 223
<212> TYPE: PRT
<213> ORGANISM: Homo sapiens

<400> SEQUENCE: 9

```
Val Met Glu Leu Leu Glu Glu Asp Leu Thr Cys Pro Ile Cys Cys Ser
  1               5                  10                  15
Leu Phe Asp Asp Pro Arg Val Leu Pro Cys Ser His Asn Phe Cys Lys
                 20                  25                  30
Lys Cys Leu Glu Gly Ile Leu Glu Gly Ser Val Arg Asn Ser Met Trp
             35                  40                  45
Arg Pro Ala Pro Phe Lys Cys Pro Thr Cys Arg Lys Glu Thr Ser Ala
         50                  55                  60
Thr Gly Ile Asn Ser Leu Gln Val Asn Tyr Ser Leu Lys Gly Ile Val
 65                  70                  75                  80
Glu Lys Tyr Asn Lys Ile Lys Ile Ser Pro Lys Met Pro Val Cys Lys
                 85                  90                  95
Gly His Met Gly Gln Pro Leu Asn Ile Phe Cys Leu Thr Asp Met Gln
            100                 105                 110
Leu Ile Cys Gly Ile Cys Ala Thr Arg Gly Glu His Thr Lys His Val
            115                 120                 125
Phe Cys Ser Ile Glu Asp Ala Tyr Ala Gln Glu Arg Asp Ala Phe Glu
        130                 135                 140
Ser Leu Phe Gln Ser Phe Glu Thr Trp Arg Arg Gly Asp Ala Leu Ser
145                 150                 155                 160
Arg Leu Asp Thr Met Glu Thr Ser Lys Arg Lys Ser Leu Gln Leu Met
                165                 170                 175
Thr Lys Asp Ser Asp Lys Val Lys Glu Phe Phe Glu Lys Leu Gln His
            180                 185                 190
Thr Leu Asp Gln Lys Lys Asn Glu Ile Leu Ser Asp Phe Glu Thr Met
        195                 200                 205
Lys Leu Ala Val Met Gln Ala Tyr Asp Pro Glu Ile Asn Lys Leu
    210                 215                 220
```

<210> SEQ ID NO 10
<211> LENGTH: 218
<212> TYPE: PRT
<213> ORGANISM: Mus musculus

<400> SEQUENCE: 10

```
Val Leu Glu Met Ile Lys Glu Val Thr Cys Pro Ile Cys Leu Glu
  1               5                  10                  15
Leu Leu Lys Glu Pro Val Ser Ala Asp Cys Asn His Ser Phe Cys Arg
                 20                  25                  30
Ala Cys Ile Thr Leu Asn Tyr Glu Ser Asn Arg Asn Thr Asp Gly Lys
             35                  40                  45
Gly Asn Cys Pro Val Cys Arg Val Pro Tyr Pro Phe Gly Asn Leu Arg
         50                  55                  60
Pro Asn Leu His Val Ala Asn Ile Val Glu Arg Leu Lys Gly Phe Lys
 65                  70                  75                  80
Ser Ile Pro Glu Glu Glu Gln Lys Val Asn Ile Cys Ala Gln His Gly
```

```
                    85                  90                  95
Glu Lys Leu Arg Leu Phe Cys Arg Lys Asp Met Met Val Ile Cys Trp
                100                 105                 110

Leu Cys Glu Arg Ser Gln Glu His Arg Gly His Gln Thr Ala Leu Ile
            115                 120                 125

Glu Glu Val Asp Gln Glu Tyr Lys Glu Lys Leu Gln Gly Ala Leu Trp
        130                 135                 140

Lys Leu Met Lys Lys Ala Lys Ile Cys Asp Glu Trp Gln Asp Asp Leu
145                 150                 155                 160

Gln Leu Gln Arg Val Asp Trp Glu Asn Gln Ile Gln Ile Asn Val Glu
                165                 170                 175

Asn Val Gln Arg Gln Phe Lys Gly Leu Arg Asp Leu Leu Asp Ser Lys
                180                 185                 190

Glu Asn Glu Glu Leu Gln Lys Leu Lys Glu Lys Lys Glu Val Met
        195                 200                 205

Glu Lys Leu Glu Glu Ser Glu Asn Glu Leu
        210                 215

<210> SEQ ID NO 11
<211> LENGTH: 124
<212> TYPE: PRT
<213> ORGANISM: Mus musculus

<400> SEQUENCE: 11

Met Glu Pro Val Ala Ser Asn Ile Gln Val Leu Leu Gln Ala Ala Glu
1               5                   10                  15

Phe Leu Glu Arg Arg Glu Arg Glu Ala Glu His Gly Tyr Ala Ser Leu
                20                  25                  30

Cys Pro His His Ser Pro Gly Thr Val Cys Arg Arg Lys Pro Pro
            35                  40                  45

Leu Gln Ala Pro Gly Ala Leu Asn Ser Gly Arg Ser Val His Asn Glu
        50                  55                  60

Leu Glu Lys Arg Arg Arg Ala Gln Leu Lys Arg Cys Leu Glu Gln Leu
65                  70                  75                  80

Arg Gln Gln Met Pro Leu Gly Val Asp Cys Thr Arg Tyr Thr Thr Leu
                85                  90                  95

Ser Leu Leu Arg Ala Arg Val His Ile Gln Lys Leu Glu Glu Gln Glu
                100                 105                 110

Gln Gln Ala Arg Arg Leu Lys Glu Lys Leu Arg Ser
        115                 120

<210> SEQ ID NO 12
<211> LENGTH: 125
<212> TYPE: PRT
<213> ORGANISM: Homo sapiens

<400> SEQUENCE: 12

Met Glu Pro Leu Ala Ser Asn Ile Gln Val Leu Leu Gln Ala Ala Glu
1               5                   10                  15

Phe Leu Glu Arg Arg Glu Arg Glu Ala Glu His Gly Tyr Ala Ser Leu
                20                  25                  30

Cys Pro His Arg Ser Pro Gly Pro Ile His Arg Arg Lys Lys Arg Pro
            35                  40                  45

Pro Gln Ala Pro Gly Ala Gln Asp Ser Gly Arg Ser Val His Asn Glu
        50                  55                  60

Leu Glu Lys Arg Arg Arg Ala Gln Leu Lys Arg Cys Leu Glu Arg Leu
65                  70                  75                  80
```

```
Lys Gln Gln Met Pro Leu Gly Gly Asp Cys Ala Arg Tyr Thr Thr Leu
                85                  90                  95

Ser Leu Leu Arg Arg Ala Arg Met His Ile Gln Lys Leu Glu Asp Gln
            100                 105                 110

Glu Gln Arg Ala Arg Gln Leu Lys Glu Arg Leu Arg Thr
        115                 120                 125

<210> SEQ ID NO 13
<211> LENGTH: 63
<212> TYPE: PRT
<213> ORGANISM: Mus musculus

<400> SEQUENCE: 13

Lys Gln Gln Ser Leu Gln Gln Gln Leu Glu Gln Leu Gln Gly Leu Pro
 1               5                  10                  15

Gly Ala Arg Glu Arg Glu Arg Leu Arg Ala Asp Ser Leu Asp Ser Ser
            20                  25                  30

Gly Leu Ser Ser Glu Arg Ser Asp Ser Asp Gln Glu Asp Leu Glu Val
        35                  40                  45

Asp Val Glu Asn Leu Val Phe Gly Thr Glu Thr Glu Leu Leu Gln
     50                  55                  60

<210> SEQ ID NO 14
<211> LENGTH: 63
<212> TYPE: PRT
<213> ORGANISM: Homo sapiens
<220> FEATURE:
<221> NAME/KEY: VARIANT
<222> LOCATION: (8)...(8)
<223> OTHER INFORMATION: Xaa = Any amino acid

<400> SEQUENCE: 14

Lys Gln Gln Ser Leu Gln Arg Xaa Trp Met Gln Leu Arg Gly Leu Ala
 1               5                  10                  15

Gly Ala Ala Glu Arg Glu Arg Leu Arg Ala Asp Ser Leu Asp Ser Ser
            20                  25                  30

Gly Leu Ser Ser Glu Arg Ser Asp Ser Asp Gln Glu Glu Leu Glu Val
        35                  40                  45

Asp Val Glu Ser Leu Val Phe Gly Gly Glu Ala Glu Leu Leu Arg
     50                  55                  60

<210> SEQ ID NO 15
<211> LENGTH: 733
<212> TYPE: DNA
<213> ORGANISM: Homo sapiens
<220> FEATURE:
<221> NAME/KEY: variation
<222> LOCATION: (454)...(454)
<223> OTHER INFORMATION: n = A, C, G, or T
<220> FEATURE:
<221> NAME/KEY: variation
<222> LOCATION: (481)...(481)
<223> OTHER INFORMATION: n = A, C, G, or T
<220> FEATURE:
<221> NAME/KEY: variation
<222> LOCATION: (499)...(499)
<223> OTHER INFORMATION: n = A, C, G, or T
<220> FEATURE:
<221> NAME/KEY: variation
<222> LOCATION: (690)...(690)
<223> OTHER INFORMATION: n = A, C, G, or T
<220> FEATURE:
<221> NAME/KEY: variation
<222> LOCATION: (732)...(732)
<223> OTHER INFORMATION: n = A, C, G, or T
```

```
<400> SEQUENCE: 15
cagccgcttg ctccggccgg caccctaggc cgcagtccgc caggctgtcg ccgacatgga    60
acccttggcc agcaacatcc aggtcctgct gcaggcggcc gagttcctgg agcgccgtga   120
gagagaggcc gagcatggtt atgcgtccct gtgcccgcat cgcagtccag cccccatcca   180
caggaggaag aagcgacccc cccaggctcc tggcgcgcag acagcgggc ggtcagtgca    240 caatgaactg gagaagcgca ggagggccca gttgaagcgg tgcctggagc ggctgaagca   300
gcagatgccc ctgggcggcg actgtgcccg gtacaccacg ctgagcctgc tgcgccgtgc   360
caggatgcac atccagaagc tggaggatca ggagcagcgg gcccgacagc tcaaggagag   420
gctgcgcaca aagcagcaga gcctgcagcg gcantggatg cagctccggg ggctggcagg   480
ngcggccgag cgggagcgnc tgcgggcgga cagtctggac tcctcaggcc tctcctctga   540
gcgctcagac tcagaccaag aggagctgga ggtggatgtg gagagcctgg tgtttggggg   600
tgaggccgag ctgctgcggg gcttcgtcgc cggccaggag cacagctact cgcacgtcgg   660
cggcgcctgg ctatgatgtt cctcacccan ggcgggcctc tgccctctta ctcgttgccc   720
aagcccactt tnc                                                     733

<210> SEQ ID NO 16
<211> LENGTH: 206
<212> TYPE: PRT
<213> ORGANISM: Homo sapiens
<220> FEATURE:
<221> NAME/KEY: VARIANT
<222> LOCATION: (133)...(133)
<223> OTHER INFORMATION: Xaa = Any amino acid

<400> SEQUENCE: 16

Met Glu Pro Leu Ala Ser Asn Ile Gln Val Leu Leu Gln Ala Ala Glu
 1               5                  10                  15

Phe Leu Glu Arg Arg Glu Arg Glu Ala Glu His Gly Tyr Ala Ser Leu
            20                  25                  30

Cys Pro His Arg Ser Pro Gly Pro Ile His Arg Arg Lys Lys Arg Pro
        35                  40                  45

Pro Gln Ala Pro Gly Ala Gln Asp Ser Gly Arg Ser Val His Asn Glu
    50                  55                  60

Leu Glu Lys Arg Arg Ala Gln Leu Lys Arg Cys Leu Glu Arg Leu
65                  70                  75                  80

Lys Gln Gln Met Pro Leu Gly Gly Asp Cys Ala Arg Tyr Thr Thr Leu
                85                  90                  95

Ser Leu Leu Arg Arg Ala Arg Met His Ile Gln Lys Leu Glu Asp Gln
            100                 105                 110

Glu Gln Arg Ala Arg Gln Leu Lys Glu Arg Leu Arg Thr Lys Gln Gln
        115                 120                 125

Ser Leu Gln Arg Xaa Trp Met Gln Leu Arg Gly Leu Ala Gly Ala Ala
    130                 135                 140

Glu Arg Glu Arg Leu Arg Ala Asp Ser Leu Asp Ser Ser Gly Leu Ser
145                 150                 155                 160

Ser Glu Arg Ser Asp Ser Asp Gln Glu Glu Leu Glu Val Asp Val Glu
                165                 170                 175

Ser Leu Val Phe Gly Gly Glu Ala Glu Leu Leu Arg Gly Phe Val Ala
            180                 185                 190

Gly Gln Glu His Ser Tyr Ser His Val Gly Gly Ala Trp Leu
        195                 200                 205
```

```
<210> SEQ ID NO 17
<211> LENGTH: 227
<212> TYPE: PRT
<213> ORGANISM: Mus musculus

<400> SEQUENCE: 17

Met Ala Thr Ala Val Gly Met Asn Ile Gln Leu Leu Glu Ala Ala
 1               5                  10                  15

Asp Tyr Leu Glu Arg Arg Glu Arg Glu Ala Glu His Gly Tyr Ala Ser
             20                  25                  30

Met Leu Pro Tyr Ser Lys Asp Arg Asp Ala Phe Lys Arg Arg Asn Lys
         35                  40                  45

Pro Lys Lys Asn Ser Thr Ser Ser Arg Ser Thr His Asn Glu Met Glu
     50                  55                  60

Lys Asn Arg Arg Ala His Leu Arg Leu Cys Leu Glu Lys Leu Lys Gly
 65                  70                  75                  80

Leu Val Pro Leu Gly Pro Glu Ser Ser Arg His Thr Thr Leu Ser Leu
                 85                  90                  95

Leu Thr Lys Ala Lys Leu His Ile Lys Lys Leu Glu Asp Cys Asp Arg
            100                 105                 110

Lys Ala Val His Gln Ile Asp Gln Leu Gln Arg Glu Gln Arg His Leu
        115                 120                 125

Lys Arg Arg Leu Glu Lys Leu Gly Ala Glu Arg Thr Arg Met Asp Ser
130                 135                 140

Val Gly Ser Val Val Ser Ser Glu Arg Ser Asp Ser Asp Arg Glu Glu
145                 150                 155                 160

Leu Asp Val Asp Val Asp Val Asp Val Asp Val Glu Gly Thr
                165                 170                 175

Asp Tyr Leu Asn Gly Asp Leu Gly Trp Ser Ser Ser Val Ser Asp Ser
            180                 185                 190

Asp Glu Arg Gly Ser Met Gln Ser Leu Gly Ser Asp Glu Gly Tyr Ser
        195                 200                 205

Ser Ala Thr Val Lys Arg Ala Lys Leu Gln Asp Gly His Lys Ala Gly
    210                 215                 220

Leu Gly Leu
225

<210> SEQ ID NO 18
<211> LENGTH: 221
<212> TYPE: PRT
<213> ORGANISM: Homo sapiens

<400> SEQUENCE: 18

Met Ala Ala Ala Val Arg Met Asn Ile Gln Met Leu Leu Glu Ala Ala
 1               5                  10                  15

Asp Tyr Leu Glu Arg Arg Glu Arg Glu Ala Glu His Gly Tyr Ala Ser
             20                  25                  30

Met Leu Pro Tyr Asn Asn Lys Asp Arg Asp Ala Leu Lys Arg Arg Asn
         35                  40                  45

Lys Ser Lys Lys Asn Asn Ser Ser Ser Arg Ser Thr His Asn Glu Met
     50                  55                  60

Glu Lys Asn Arg Arg Ala His Leu Arg Leu Cys Leu Glu Lys Leu Lys
 65                  70                  75                  80

Gly Leu Val Pro Leu Gly Pro Glu Ser Ser Arg His Thr Thr Leu Ser
                 85                  90                  95

Leu Leu Thr Lys Ala Lys Leu His Ile Lys Lys Leu Glu Asp Cys Asp
            100                 105                 110
```

Arg Lys Ala Val His Gln Ile Asp Gln Leu Gln Arg Glu Gln Arg His
         115                 120                 125

Leu Lys Arg Gln Leu Glu Lys Leu Gly Ile Glu Arg Ile Arg Met Asp
    130                 135                 140

Ser Ile Gly Ser Thr Val Ser Ser Glu Arg Asp Ser Asp Arg Glu
145                 150                 155                 160

Glu Ile Asp Val Asp Val Glu Ser Thr Asp Tyr Leu Thr Gly Asp Leu
                    165                 170                 175

Asp Trp Ser Ser Ser Val Ser Asp Ser Asp Glu Arg Gly Ser Met
                180                 185                 190

Gln Ser Leu Gly Ser Asp Glu Gly Tyr Ser Ser Thr Ser Ile Lys Arg
        195                 200                 205

Ile Lys Leu Gln Asp Ser His Lys Ala Cys Leu Gly Leu
    210                 215                 220

<210> SEQ ID NO 19
<211> LENGTH: 221
<212> TYPE: PRT
<213> ORGANISM: Homo sapiens

<400> SEQUENCE: 19

Met Ala Ala Val Arg Met Asn Ile Gln Met Leu Leu Glu Ala Ala
 1               5                  10                  15

Asp Tyr Leu Glu Arg Arg Glu Arg Glu Ala Glu His Gly Tyr Ala Ser
                20                  25                  30

Met Leu Pro Tyr Asn Asn Lys Asp Arg Asp Ala Leu Lys Arg Arg Asn
            35                  40                  45

Lys Ser Lys Lys Asn Asn Ser Ser Arg Ser Thr His Asn Glu Met
50                  55                  60

Glu Lys Asn Arg Arg Ala His Leu Arg Leu Cys Leu Glu Lys Leu Lys
65                  70                  75                  80

Gly Leu Val Pro Leu Gly Pro Glu Ser Ser Arg His Thr Thr Leu Ser
                85                  90                  95

Leu Leu Thr Lys Ala Lys Leu His Ile Lys Lys Leu Glu Asp Cys Asp
            100                 105                 110

Arg Lys Ala Val His Gln Ile Asp Gln Leu Gln Arg Glu Gln Arg His
        115                 120                 125

Leu Lys Arg Gln Leu Glu Lys Leu Gly Ile Glu Arg Ile Arg Met Asp
    130                 135                 140

Ser Ile Gly Ser Thr Val Ser Ser Glu Arg Asp Ser Asp Arg Glu
145                 150                 155                 160

Glu Ile Asp Val Asp Val Glu Ser Thr Asp Tyr Leu Thr Gly Asp Leu
                165                 170                 175

Asp Trp Ser Ser Ser Val Ser Asp Ser Asp Glu Arg Gly Ser Met
                180                 185                 190

Gln Ser Leu Gly Ser Asp Glu Gly Tyr Ser Ser Thr Ser Ile Lys Arg
        195                 200                 205

Ile Lys Leu Gln Asp Ser His Lys Ala Cys Leu Gly Leu
    210                 215                 220

<210> SEQ ID NO 20
<211> LENGTH: 207
<212> TYPE: PRT
<213> ORGANISM: Mus musculus

<400> SEQUENCE: 20

```
Met Glu Leu Asn Ser Leu Leu Leu Leu Glu Ala Ala Glu Tyr Leu
1               5                   10                  15

Glu Arg Arg Asp Arg Glu Ala Glu His Gly Tyr Ala Ser Met Leu Pro
            20                  25                  30

Phe Asp Gly Asp Phe Ala Arg Lys Lys Thr Lys Thr Ala Gly Leu Val
            35                  40                  45

Arg Lys Gly Pro Asn Asn Arg Ser Ser His Asn Glu Leu Glu Lys His
        50                  55                  60

Arg Arg Ala Lys Leu Arg Leu Tyr Leu Glu Gln Leu Lys Gln Leu Gly
65                  70                  75                  80

Pro Leu Gly Pro Asp Ser Thr Arg His Thr Thr Leu Ser Leu Leu Lys
            85                  90                  95

Ala Lys Met His Ile Lys Lys Leu Glu Glu Gln Asp Arg Arg Ala Leu
            100                 105                 110

Ser Ile Lys Glu Gln Leu Gln Arg Glu His Arg Phe Leu Lys Arg Arg
        115                 120                 125

Leu Glu Gln Leu Ser Val Gln Ser Val Arg Val Arg Thr Asp Ser Thr
        130                 135                 140

Gly Ser Ala Val Ser Thr Asp Ser Glu Gln Glu Val Asp Ile Glu
145                 150                 155                 160

Gly Met Glu Phe Gly Pro Gly Glu Leu Asp Ser Ala Gly Ser Ser Ser
            165                 170                 175

Asp Ala Asp Asp His Tyr Ser Leu Gln Ser Ser Gly Cys Ser Asp Ser
            180                 185                 190

Ser Tyr Gly His Pro Cys Arg Arg Pro Gly Cys Pro Gly Leu Ser
        195                 200                 205

<210> SEQ ID NO 21
<211> LENGTH: 205
<212> TYPE: PRT
<213> ORGANISM: Mus musculus

<400> SEQUENCE: 21

Met Glu Pro Val Ala Ser Asn Ile Gln Val Leu Leu Gln Ala Ala Glu
1               5                   10                  15

Phe Leu Glu Arg Arg Glu Arg Glu Ala Glu His Gly Tyr Ala Ser Leu
            20                  25                  30

Cys Pro His His Ser Pro Gly Thr Val Cys Arg Arg Lys Pro Pro
        35                  40                  45

Leu Gln Ala Pro Gly Ala Leu Asn Ser Gly Arg Ser Val His Asn Glu
        50                  55                  60

Leu Glu Lys Arg Arg Arg Ala Gln Leu Lys Arg Cys Leu Glu Gln Leu
65                  70                  75                  80

Arg Gln Gln Met Pro Leu Gly Val Asp Cys Thr Arg Tyr Thr Thr Leu
            85                  90                  95

Ser Leu Leu Arg Ala Arg Val His Ile Gln Lys Leu Glu Glu Gln Glu
            100                 105                 110

Gln Gln Ala Arg Arg Leu Lys Glu Lys Leu Arg Ser Lys Gln Gln Ser
        115                 120                 125

Leu Gln Gln Gln Leu Glu Gln Leu Gln Gly Leu Pro Gly Ala Arg Glu
        130                 135                 140

Arg Glu Arg Leu Arg Ala Asp Ser Leu Asp Ser Ser Gly Leu Ser Ser
145                 150                 155                 160

Glu Arg Ser Asp Ser Asp Gln Glu Asp Leu Glu Val Asp Val Glu Asn
            165                 170                 175
```

-continued

```
Leu Val Phe Gly Thr Glu Thr Glu Leu Leu Gln Ser Phe Ser Ala Gly
            180                 185                 190

Arg Glu His Ser Tyr Ser His Ser Thr Cys Ala Trp Leu
            195                 200                 205

<210> SEQ ID NO 22
<211> LENGTH: 206
<212> TYPE: PRT
<213> ORGANISM: Homo sapiens
<220> FEATURE:
<221> NAME/KEY: misc_feature
<222> LOCATION: (133)..(133)
<223> OTHER INFORMATION: Xaa can be any naturally occurring amino acid

<400> SEQUENCE: 22

Met Glu Pro Leu Ala Ser Asn Ile Gln Val Leu Leu Gln Ala Ala Glu
 1               5                  10                  15

Phe Leu Phe Arg Arg Glu Arg Glu Ala Glu His Gly Tyr Ala Ser Leu
            20                  25                  30

Cys Pro His Arg Ser Pro Gly Pro Ile His Arg Arg Lys Lys Arg Pro
            35                  40                  45

Pro Gln Ala Pro Gly Ala Gln Asp Ser Gly Arg Ser Val His Asn Glu
        50                  55                  60

Leu Glu Lys Arg Arg Arg Ala Gln Leu Lys Arg Cys Leu Glu Arg Leu
65                  70                  75                  80

Lys Gln Gln Met Pro Leu Gly Gly Asp Cys Ala Arg Tyr Thr Thr Leu
                85                  90                  95

Ser Leu Leu Arg Arg Ala Arg Met His Ile Gln Lys Leu Glu Asp Gln
            100                 105                 110

Glu Gln Arg Ala Arg Gln Leu Lys Glu Arg Leu Arg Thr Lys Gln Gln
            115                 120                 125

Ser Leu Gln Arg Xaa Trp Met Gln Leu Arg Gly Leu Ala Gly Ala Ala
            130                 135                 140

Glu Arg Glu Arg Leu Arg Ala Asp Ser Leu Asp Ser Ser Gly Leu Ser
145                 150                 155                 160

Ser Glu Arg Ser Asp Ser Asp Gln Glu Glu Leu Glu Val Asp Val Glu
                165                 170                 175

Ser Leu Val Phe Gly Gly Glu Ala Glu Leu Leu Arg Gly Phe Val Ala
            180                 185                 190

Gly Gln Glu His Ser Tyr Ser His Val Gly Gly Ala Trp Leu
            195                 200                 205
```